US010603375B2

(12) United States Patent
Diamond et al.

(10) Patent No.: US 10,603,375 B2
(45) Date of Patent: *Mar. 31, 2020

(54) GENETICALLY STABLE RECOMBINANT MODIFIED VACCINIA ANKARA (RMVA) VACCINES AND METHODS OF PREPARATION THEREOF

(71) Applicant: CITY OF HOPE, Duarte, CA (US)

(72) Inventors: Don Diamond, Glendora, CA (US); Zhongde Wang, Mount Pleasant, SC (US)

(73) Assignee: CITY OF HOPE, Duarte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/589,857

(22) Filed: May 8, 2017

(65) Prior Publication Data

US 2017/0246292 A1 Aug. 31, 2017

Related U.S. Application Data

(60) Continuation of application No. 14/075,975, filed on Nov. 8, 2013, now Pat. No. 9,675,689, which is a division of application No. 12/795,621, filed on Jun. 7, 2010, now Pat. No. 8,580,276.

(60) Provisional application No. 61/184,767, filed on Jun. 5, 2009.

(51) Int. Cl.
| *A61K 39/285* | (2006.01) |
| *A61K 39/12* | (2006.01) |
| *A61K 39/245* | (2006.01) |
| *C07K 14/005* | (2006.01) |
| *C12N 7/00* | (2006.01) |
| *C12N 15/86* | (2006.01) |
| *A61K 39/00* | (2006.01) |

(52) U.S. Cl.
CPC ............ *A61K 39/285* (2013.01); *A61K 39/12* (2013.01); *A61K 39/245* (2013.01); *C07K 14/005* (2013.01); *C12N 7/00* (2013.01); *C12N 15/86* (2013.01); *A61K 2039/5256* (2013.01); *C07K 2319/40* (2013.01); *C12N 2710/16134* (2013.01); *C12N 2710/16151* (2013.01); *C12N 2710/24143* (2013.01); *C12N 2830/60* (2013.01)

(58) Field of Classification Search
None
See application file for complete search history.

(56) References Cited

U.S. PATENT DOCUMENTS

| 8,173,362 B2 | 5/2012 | Shenk et al. |
| 8,580,276 B2 | 11/2013 | Diamond et al. |
| 2003/0064077 A1 | 4/2003 | Paoletti et al. |
| 2004/0265325 A1 | 12/2004 | Diamond et al. |
| 2008/0187545 A1 | 8/2008 | Shenk et al. |
| 2009/0081230 A1 | 11/2009 | Lanzavecchia et al. |
| 2010/0143402 A1 | 6/2010 | Moss et al. |
| 2010/0285059 A1 | 11/2010 | Shenk et al. |
| 2010/0316667 A1 | 12/2010 | Diamond et al. |
| 2014/0065181 A1 | 3/2014 | Diamond et al. |

FOREIGN PATENT DOCUMENTS

| WO | 2009/049138 | 4/2009 |
| WO | 2012034025 | 3/2012 |

OTHER PUBLICATIONS

Wang et al., Blood, 2007, 110:165. (Year: 2007).*
Loh et al., J. Vet. Malaysia, 2007, 19(1):21-32. (Year: 2007).*
European Patent Office, Communication pursuant to Article 94(3) EPO dated Jul. 17, 2017 for European Application No. 13822266.6.
Wussow, F., et al., "Human Cytomegalovirus Vaccine Based on the Envelope gH/gL Pentamer Complex," PLoS Pathog. 10(11):e1004524 (2014).
Abel, et al., Vaccine-induced control of viral shedding following rhesus cytomegalovirus challenge in rhesus macaques. J.Virol. (85):2878-2890 (2011).
Abel, et al., A heterologous DNA prime/protein boost immunization strategy for rhesus cytomegalovirus. Vaccine (26):6013-6025 (2008).
Acres, "Cancer immunotherapy: phase II clinical studies with TG4010 (MVA-MUC1-IL2)," J Buon 12 Suppl 1:S71-5 (2007).
Adler, et al., Recent advances in the prevention and treatment of congenital cytomegalovirus infections. Semin Perinatol. (31):10-18 (2007).
Adler, et al., Interrupting intrauterine transmission of cytomegalovirus. Rev Med Virol. (16):69-71 (2006).
Adler, et al., Role of human cytomegalovirus UL131A in cell type-specific virus entry and release. J.Gen.Virol. (87):2451-2460 (2006).
Adler, et al., Immunity induced by primary human cytomegalovirus infection protects against secondary infection among women of childbearing age. J.Infect.Dis. (171):26-32 (1995).
Adler, et al., Safety and immunogenicity of the Towne strain cytomegalovirus vaccine. Pediatr.Infect.Dis.J. (17):200-206 (1998).
Antoine et al, "The complete genomic sequence of the modified vaccinia Ankara strain: comparison with other orthopoxviruses," Virology 244:365-396 (1998).
Arvin, et al., Vaccine development to prevent cytomegalovirus disease: report from the National Vaccine Advisory Committee. Clin.Infect.Dis. (39):233-239 (2004).
Assaf, et. al., Patterns of Acute Rhesus Cytomegalovirus (RhCMV) Infection Predict Long-Term RhCMV Infection. J.Virol. (86):6354-6357 (2012).

(Continued)

*Primary Examiner* — Nicole Kinsey White
(74) *Attorney, Agent, or Firm* — Perkins Coie LLP; Lara Dueppen; Yang Tang

(57) ABSTRACT

A method of preventing, controlling or treating CMV infections with a vaccine comprising an immunologically effective amount of a fusion cytomegalovirus (CMV) protein antigen comprising a nucleotide sequence encoding two or more antigenic portions of Immediate-Early Gene-1 or Immediate-Early Gene-2 (IEfusion), wherein the antigenic portions elicit an immune response when expressed by a vaccine.

13 Claims, 40 Drawing Sheets

Specification includes a Sequence Listing.

(56) References Cited

OTHER PUBLICATIONS

Avetisyan et al, "Evaluation of intervention strategy based on CMV-specific immune responses after allogeneic SCT," Bone Marrow Transplant 40:865-869 (2007).
Azuma et al, "2_-C-cyano-2_-deoxy-1-beta-Darabino-pentofuranosylcytosine: a novel anticancer nucleoside analog that causes both DNA strand breaks and G(2) arrest," Mol Pharmacol; 59(4):725-31 (2001).
Barouch et al, "Plasmid chemokines and colonystimulating factors enhance the immunogenicity of DNApriming-viral vector boosting human immunodeficiency virus type 1 vaccines," J. Virol. 77:8729-8735 (2003).
Barry, et al., Primate Betaherpesviruses. 1051-1075 (2007).
Barry, et al., Development of Breeding Populations of Rhesus Macaques That Are Specific Pathogen Free for Rhesus Cytomegalovirus. Comparative Medicine. (58):43-46 (2012).
Barry, et al., Nonhuman primate models of intrauterine cytomegalovirus infection. ILAR.J. (47):49-64 (2006).
Berencsi et al, "A canarypox vector-expressing cytomegalovirus (cmv) phosphoprotein 65 induces long-lasting cytotoxic t cell responses in human cmv-seronegative subjects," J. Infect. Dis. 183:1171-1179 (2001).
Bernstein, et al., Randomized, double-blind, Phase 1 trial of an alphavirus replicon vaccine for cytomegalovirus in CMV seronegative adult volunteers. Vaccine (28):484-493 (2009).
Blanchard et al, "Modified vaccinia virus Ankara undergoes limited replication in human cells and lacks several immunomodulatory proteins: implications for use as a human vaccine," J. Gen.Virol. 79(Pt 5):1159-1167 (1998).
Blut, et al., Orthopox Viruses: Infections in Humans. Transfusion Med Hemother (37): 351-364 (2010).
Boeckh et al, "Immune monitoring with iTAg(TM) MHC tetramers for prediction of recurrent or persistent cytomegalovirus multicenter clinical trial," Biol. Blood Marrow Transplant. 12:79 (2006).
Boppana, et al., Antiviral antibody responses and intrauterine transmission after primary maternal cytomegalovirus infection. J Infect Dis. (171):1115-1121 (1995).
Boppana, et al., Intrauterine transmission of cytomegalovirus to infants of women with preconceptional immunity. N. Engl. J. Med. (344):1366-1371. (2001).
Borst, E., et al., "Development of a Cytomegalovirus Vector for Somatic Gene Therapy," Bone Marrow Transplantation 25(Suppl. 2):S80-S82 (2000).
Britt et al, "Identification of a 65 000 dalton virion envelope protein of human cytomegalovirus," Virus Res 4:31-6 (1985).
Britt et al, "Structural and immunological characterization of the intracellular forms of an abundant 68,000 Mr human cytomegalovirus protein," J. Gen Virol; 68(Pt 7):1897-907) (1987).
Britt, W. J., et al., "Human Cytomegalovirus Virion Proteins," Hum. Immunol. 65:395-402 (2004).
Britt, et al., Manifestations of human cytomegalovirus infection: proposed mechanisms of acute and chronic disease. Curr Top Microbiol Immunol. (325):417-470 (2008).
Britt, et al., Induction of complement-dependent and -independent neutralizing antibodies by recombinant-derived human cytomegalovirus gp55-116 (gB) J. Virol. (62):3309-3318 (1988).
Britt, et al., Cell surface expression of human cytomegalovirus (HCMV) gp55-116 (gB): use of HCMV-recombinant vaccinia virus-infected cells in analysis of the human neutralizing antibody response. J.Virol. 64:1079-1085 (1990).
Britt, et al., Neutralizing antibodies detect a disulfide-linked glycoprotein complex within the envelope of human cytomegalovirus. Virology. (135):369-378. (1984).
Butrapet et al, "Determining genetic stabilities of chimeric dengue vaccine candidates based on dengue 2 PDK-53 virus by sequencing and quantitative TaqMAMA," J Virol Methods; 131(1); 1-9 (2006).
Carroll et al, "Highly attenuated modified vaccinia virus Ankara (MVA) as an effective recombinant vector: a murine tumor model," Vaccine 15:387-394 (1997).

Carroll et al, "Host range and cytopathogenicity of the highly attenuated MVA strain of vaccinia virus: propagation and generation of recombinant viruses in a nonhuman mammalian cell line," Virology 238:198-211 (1997).
Cha, et al., Human cytomegalovirus clinical isolates carry at least 19 genes not found in laboratory strains. J Virol. (70):78-83 (1996).
Chakrabarti et al, "Compact, synthetic, vaccinia virus early/late promoter for protein expression," Biotechniques 23:1094-7 (1997).
Cobbold et al, "Adoptive transfer of cytomegalovirus-specific CTL to stem cell transplant patients after selection byHLA-peptide tetramers," J. Exp. Med. 202:379-386 (2005).
Cosma et al, "Therapeutic vaccination with MVA-HIV-1 Nef elicits Nef-specific T-helper cell responses in chronically HIV-1 infected individuals," Vaccine 22:21-9 (2003).
Cottingham, et al., Rapid generation of markerless recombinant MVA vaccines by en passant recombineering of a self-excising bacterial artificial chromosome. J Virol Methods. (168):233-236 (2010).
Cottingham, et al., Recombination-mediated genetic engineering of a bacterial artificial chromosome clone of modified vaccinia virus Ankara (MVA). PLoS.One. 3:e1638 (2008).
Cui, et al., Cytomegalovirus vaccines fail to induce epithelial entry neutralizing antibodies comparable to natural infection. Vaccine (26):5760-5766 (2008).
Cwynarski et al, "Direct visualization of cytomegalovirusspecific T-cell reconstitution after allogeneic stem cell transplantation," Blood 97:1232-1240 (2001).
Daftarian et al, "Novel conjugates of epitope fusion peptides with CpG-ODN display enhanced immunogenicity and HIV recognition," Vaccine 23:3453-3468 (2005).
Dawson et al, "Data for biochemical research," Oxford University Press; p. 260-1 (1986).
De Haan et al, "Coronaviruses as vectors: stability of foreign gene expression," J Virol 79:12742-51 (2005).
Dewaal et al, "Vaccination of infant macaques with a recombinant MVA expressing the RSV F and G genes does not predispose for immunopathology," Vaccine 22:923-926 (2004).
Diamond et al, "Development of a candidate HLAA*0201 restricted peptide-based vaccine against human cytomegalovirus infection," Blood 90:1751-67 (1997).
Domi, et al., Cloning the vaccinia virus genome as a bacterial artificial chromosome in *Escherichia coli* and recovery of infectious virus in mammalian cells. Proc.Natl.Acad.Sci.U.S.A (99):12415-12420 (2002).
Drexler et al, "Modified vaccinia virus Ankara as antigen delivery system: how can we best use its potential?" Curr Opin Biotechnol 15:506-12 (2004).
Dunn, et al., Functional profiling of a human cytomegalovirus genome. Proc Natl Acad Sci U S A. (100):14223-14228 (2003).
Earl et al, "Design and evaluation of multi-gene, multi-clade HIV-1MVAvaccines." Vaccine; 27(42):5885-95 (2009).
Earl et al, "Recombinant modified vaccinia virus Ankara provides durable protection against disease caused by an immunodeficiency virus as well as long-term immunity to an orthopoxvirus in a non-human primate," Virology 366:84-97 (2007).
Earl, et al., Generation of recombinant vaccinia viruses. Curr.Protoc. Mol.Biol. Chapter 16:Unit16 (2001).
Einsele et al, "Infusion of cytomegalovirus (CMV)-specific T cells for the treatment of CMVinfection not responding to antiviral chemotherapy," Blood 99:3916-3922 (2002).
Endresz, et al., Optimization of DNA immunization against human cytomegalovirus. Vaccine (19):3972-3980 (2001).
Erfle et al, "Vaccines based on Nef and on Nef/DeltaV2," Env. Microbes Infect; 7(14):1400-4 (2005).
Espenschied et al, "CTLA-4 blockage enhances the therapeutic effect of an attenuated poxvirus vaccine targeting p53 in an established murine tumor model," J Immunol 170:3401-7 (2003).
Fayzulin et al, "Evaluation of replicative capacity and genetic stability of West Nile virus replicons using highly efficient packaging cell lines," Virology; 351(1)196-209 (2006).
Firat et al, "Comparative analysis of the CD8(+) T cell repertoires of H-2 class I wild-type/HLA-A2.1 and H-2 class I knockout/HLA-A2.1 transgenic mice," Int. Immunol. 14:925-934 (2002).

(56) References Cited

OTHER PUBLICATIONS

Fouts, et al., Antibodies against the gH/gL/UL128/UL130/UL131 complex comprise the majority of the anti-CMV neutralizing antibody response in CMV-HIG. J.Virol. (86):7444-7447 (2012).
Gallez-Hawkins et al, "Ctyomegalovirusimmune reconstitution occurs in recipients of allogeneic hematopoietic celltransplants irrespective of detectable cytomegalovirus infection," Biol. Blood MarrowTransplant. 11:890-902 (2005).
Genini, et al., Serum antibody response to the gH/gL/pUL128-131 five-protein complex of human cytomegalovirus (HCMV) in primary and reactivated HCMV infections. J.Clin.Virol. (52):113-118 (2011).
Gerna, et al., Human cytomegalovirus serum neutralizing antibodies block virus infection of endothelial/epithelial cells, but not fibroblasts, early during primary infection. J.Gen.Virol. (89):853-865 (2008).
Ghanekar et al, "Gamma interferon expression in CD8(+) T cells is a marker for circulating cytotoxic T lymphocytes that recognize an HLA A2-restricted epitope of human cytomegalovirus phosphoprotein pp65," Clin. Diagn. Lab. Immunol. 8:628-631 (2001).
Gherardi et al, "Recombinant poxviruses as mucosal vaccine vectors," J Gen Virol 86:2925-36 (2005).
Gilbert et al, "Cytomegalovirus selectively blocks antigen processing and presentation of its immediate-early gene product," Nature 383:720-722 (1996).
Gilbert et al, "Selective interference with class I major histocompatibility complex presentation of the major immediate-early protein infection with human cytomegalovirus," J. Virol. 67:3461-3469 (1993).
Gilbert et al, "Synergistic DNA-MVA prime-boost vaccination regimes for malaria and tuberculosis," Vaccine 24:4554-61 (2006).
Gomez et al, "Head-to-head comparison on the immunogenicity of two HIV/AIDS vaccine candidates based on the attenuated poxvirus strains MVA and NYVAC co-expressing in a single locus the HIV-1BX08 gp120 and HIV-1(IIIB) Gag-Pol-Nef proteins of Clade B," Vaccine 25:2863-2885 (2007).
Gonczol, et al., Isolated gA/gB glycoprotein complex of human cytomegalovirus envelope induces humoral and cellular immuneresponses in human volunteers. Vaccine. (8):130-136 (1990).
Gonczol, et al., Development of a cytomegalovirus vaccine: lessons from recent clinical trials. Expert Opin Biot Ther. (1):401-412 (2001).
Goonetilleke et al, "Induction of multifunctional human immunodeficiency virus type 1 (HIV-1)-specific T cells capable of proliferation in healthy subjects by using a prime-boost regimen of DNA and modified vaccinia virus Ankara-vectored vaccines expressing HIV-1 gag coupled to CD8+ T-cell epitopes," J. Virol. 80:4717-4728 (2006).
Gratama et al, "Tetramer-based quantification of cytomegalovirus (CMV)-specific CD8+ T lymphocytes in T-cell-depleted stem cell grafts and after transplantation may identify patients at risk for progressive CMV infection," Blood 98:1358-1364 (2001).
Grazia, et al., In vitro selection of human cytomegalovirus variants unable to transfer virus and virus products from infected cells to polymorphonuclear leukocytes and to grow in endothelial cells. J Gen Virol. (82):1429-1438 (2001).
Griffiths, et al., Cytomegalovirus glycoprotein-B vaccine with MF59 adjuvant in transplant recipients: a phase 2 randomised placebocontrolled trial. Lancet (377):1256-1263 (2011).
Gyulai et al, "Cytotoxic T lymphocyte (CTL) responses to human cytomegalovirus pp65, IE1-Exon4, gB, pp150, and pp28 in healthy individuals: reevaluation of prevalence of IE1-Specific CTLs," J. Infect. Dis. 181:1537-1514 (2000).
Hahn, et al., Human cytomegalovirus UL131-128 genes are indispensable for virus growth in endothelial cells and virus transfer to leukocytes. J.Virol. (78):10023-10033 (2004).
Hanke et al, "Biodistribution and persistence of an MVA-vectored candidate HIV vaccine in SIV-infected rhesus macaques and SCID mice," Vaccine 23:1507-1514 (2005).
Hansen, et al., Evasion of CD8+ T cells is critical for superinfection by cytomegalovirus. Science. (328):102-106 (2010).
Hansen, et al., Complete sequence and genomic analysis of rhesus cytomegalovirus. J.Virol. (77):6620-6636 (2003).
Heineman, et al., A phase 1 study of 4 live, recombinant human cytomegalovirus Towne/Toledo chimeric vaccines. J Infect Dis. (193):1350-1360 (2006).
Huff, et al., Differential detection of B virus and rhesus cytomegalovirus in rhesus macaques. J.Gen.Virol. (84):83-92 (2003).
Isaacson, et al., Human cytomegalovirus glycoprotein B is required for virus entry and cell-to-cell spread but not for virion attachment, assembly, or egress. J.Virol. (83):3891-3903 (2009).
Jarvis, et al., Molecular basis of persistence and latency. Human Herpesviruses: Biology, Therapy, and Immunoprophylaxis. Cambridge University Press; (2007).
Johnson et al, "Domain mapping of the human cytomegalovirus IE1-72 and cellular p107 protein-protein interactionand the possible functional consequences," J. Gen. Virol. 80(5):1293-1303 (1999).
Johnson, et al., O-linked oligosaccharides are acquired by herpes simplex virus glycoproteins in the Golgi apparatus. Cell (32):987-997 (1983).
Kern et al, "Target structures of the CD8(+)-T-cell response to human cytomegalovirus: the 72 kilodalton major immediate-early protein revisited," J. Virol. 73:8179-8184 (1999).
Khan et al, "Comparative analysis of CD8+ T cell responses against human cytomegalovirus proteins pp65 and immediate early 1 shows similarities in precursor frequency, oligoclonality, and phenotype," J Infect Dis 185:1025-34 (2002).
Khan et al, "Identification of cytomegalovirus-specific cytotoxic T lymphocytes in vitro is greatly enhanced by the use of recombinant virus lacking the US2 to US11 region or modified vaccinia virus Ankara expressing individual viral genes," J. Virol. 79:2869-2879 (2005).
Khan et al, "T cell recognition patterns of immunodominant cytomegalovirus antigens in primary and persistent infection," J. Immunol. 178:4455-4465 (2007).
Khanna et al, "Human cytomegalovirus vaccine: time to look for alternative options," Trends Mol. Med. 12:26-33 (2006).
Kharfan-Dabaja, et al., A novel therapeutic cytomegalovirus DNA vaccine in allogeneic haemopoietic stem-cell transplantation: a randomised, double-blind, placebo-controlled, phase 2 trial. Lancet Infect. Dis. (12):290-299 (2012).
Kidokoro et al, "Genetically stable and fully effective smallpox vaccine strain constructed from highly attenuated vaccinia LC16m8," Proc Natl Acad Sci USA; 102(11):4152-7 (2005).
Kinzler, et al., Characterization of human cytomegalovirus glycoproteininduced cell-cell fusion. J Virol. (79):7827-7837 (2005).
Krishnan et al, "A novel approach to evaluate the immunogenicity of viral antigens of clinical importance in HLA transgenic murine models," Immunol Lett; 120(1-2):108-16 (2008).
La Rosa et al, "Enhanced immune activity of cytotoxic T-lymphocyte epitope analogs derived from positional scanning synthetic combinatorial libraries," Blood 97:1776-86 (2001).
La Rosa et al, "In vitro expansion of polyclonal T-cell subsets for adoptive immunotherapy by recombinant modified vaccinia Ankara," Exp Hematol 34:497-507 (2006).
La Rosa et al, "Longitudinal assessment of cytomegalovirus (CMV)-specific immune responses in liver transplant recipients at high risk for late CMV disease," J. Infect. Dis. 195:633-644 (2007).
La Rosa et al, "Preclinical development of an adjuvant-free peptide vaccine with activity against CMV pp65 in HLA transgenic mice," Blood; 100(10):3681-9 (2002).
La Torre, et al., Placental enlargement in women with primary maternal cytomegalovirus infection is associated with fetal and neonatal disease. Clin Infect Dis. (43):994-1000 (2006).
Lacey et al, "Functional comparison of T cells recognizing cytomegalovirus pp65 and intermediate-early antigen polypeptides in hematopoietic stem-cell transplant and solid organ transplant recipients," J. Infect. Dis. 194:1410-1421 (2006).
Lai et al, "A rapid method for screening vaccinia virus recombinants," Biotechniques 10:564-5 (1991).
Lemonnier, "The utility of H-2 class I knockout mice," Virus Res. 82:87-90 (2002).

(56) References Cited

OTHER PUBLICATIONS

Lilja, et al., Efficient replication of rhesus cytomegalovirus variants in multiple rhesus and human cell types. Proc.Natl.Acad.Sci.U.S.A (105):19950-19955 (2008).
Lilleri, et al., Development of Human Cytomegalovirus-Specific T Cell Immunity during Primary Infection of Pregnant Women and Its Correlation with Virus Transmission to the Fetus. J Infect Dis. (195):1062-1070 (2007).
Limaye et al, "Impact of cytomegalovirus in organ transplant recipients in the era of antiviral prophylaxis," Transplantation 81(12):1645-1652 (2006).
Liu, et al., The N-terminal 513 amino acids of the envelope glycoprotein gB of human cytomegalovirus stimulates both B- and T-cell immune responses in humans. J Virol. (65):1644-1648 (1991).
Ljungman et al, "Risk factors for development of cytomegalovirus disease after allogeneic stem cell transplantation," Haematolgica 91:78-83 (2006).
Longmate et al, "Population coverage by HLA class-I restricted cytotoxic T-lymphocyte epitopes," Immunogenetics 52:165-173 (2001).
Lubaki, et al., A novel method for detection and ex vivo expansion of HIV type 1-specific cytolytic T lymphocytes. AIDS Res Hum Retroviruses. (10):1427-1431 (1994).
Macagno, et al., Isolation of human monoclonal antibodies that potently neutralize human cytomegalovirus infection by targeting different epitopes on the gH/gL/UL128-131A complex. J.Virol. (84):1005-1013 (2010).
Maecker et al, "Impact of cryopreservation on tetramer, cytokine flow cytometry, and ELISPOT," BMC Immunol. 6:17 (2005).
Maidji, et al., Maternal antibodies enhance or prevent cytomegalovirus infection in the placenta by neonatal Fc receptormediated transcytosis. Am J Pathol. (168):1210-1226 (2006).
Maidji, et al.,Transmission of human cytomegalovirus from infected uterine microvascular endothelial cells to differentiating/invasive placental cytotrophoblasts. Virology. (304):53-69 (2002).
Manley et al, "Immune evasion proteins of human cytomegalovirus do not prevent a diverse CD8+ cytotoxic T-cell response in natural infection," Blood 104:1075-1082 (2004).
Mansat, et al., Cytomegalovirus detection in cryopreserved semen samples collected for therapeutic donor insemination. Hum Reprod. (12):1663-1666 (1997).
Manuel, et al., Intergenic region 3 of modified vaccinia ankara is a functional site for insert gene expression and allows for potent antigen-specific immune responses. Virology. (403):155-162 (2010).
Marshall, et al., Ontogeny of glycoprotein gB-specific antibody and neutralizing activity during natural cytomegalovirus infection. J.Med.Virol. (43):77-83 (1994).
Mayr et al, "Vaccination against pox diseases under immunosuppressive conditions." Dev. Biol. Stand, 41:225-34, 225-234 (1978).
Mayr, et al., Attenuation of virulent fowl pox virus in tissue culture and characteristics of the attenuated virus. Zentralbl.Veterinarmed.B (13):1-13 (1966).
Meyer et al, "Mapping of deletions in the genome of the highly attenuated vaccinia virusMVA and their influence on virulence," J.Gen.Virol. 72(5):1031-1038 (1991).
Mohr, C. A., et al., "Engineering of Cytomegalovirus Genomes for Recombinant Live Herpesvirus Vaccines," Int. J. Med. Microbiol. 298:115-125 (2008).
Moorthy et al, "Safety and immunogenicity of DNA/modified vaccinia virus Ankara malaria vaccination in African adults," J. Infect. Dis. 188:1239-1244 (2003).
Morello et al, "Suppression of murine cytomegalovirus (MCMV) replication with a DNA vaccine encoding MCMV M84 (a homolog of human cytomegalovirus pp65)," J. Virol. 74:3696-3708 (2000).
Moss, "Genetically engineered poxviruses for recombinant gene expression, vaccination, and safety," Proc Natl Acad Sci USA; 93(21):11341-8 (1996).
Moss et al, "Host range restricted, non-replicating vaccinia virus vectors as vaccine candidates," Adv Exp Med Biol 397:7-13 (1996).
Murphy, et al., Coding potential of laboratory and clinical strains of human cytomegalovirus. Proc.Natl.Acad.Sci.U.S.A (100):14976-14981 (2003).
Navarro, et al., Glycoprotein B of human cytomegalovirus promotes virion penetration into cells, transmission of infection from cell to cell, and fusion of infected cells. Virology. (197):143-158 (1993).
Nigro, et al., Regression of fetal cerebral abnormalities by primary cytomegalovirus infection following hyperimmunoglobulin therapy. Prenat Diagn. (28):512-517 (2008).
Nigro, et al., Passive immunization during pregnancy for congenital cytomegalovirus infection. N. Engl.J.Med. (353):1350-1362 (2005).
Oxford, et al., Open reading frames carried on Ul/b' are implicated in shedding and horizontal transmission of rhesus cytomegalovirus in rhesus monkeys. J.Virol. (85):5105-5114 (2011).
Oxford, et al., Protein coding content of the UL)b' region of wild-type rhesus cytomegalovirus. Virology (373):181-188 (2008).
Pascolo et al, "HLAA2.1-restricted education and cytolytic activity of CD8(+) T lymphocytes from beta2 microglobulin (beta2m) HLA-A2.1 monochain transgenic H-2Db beta2m double knockout mice," J. Exp. Med. 185:2043-2051 (1997).
Pass et al, "Congenital cytomegalovirus infection following first trimester maternal infection: symptoms at birth and outcome," J. Clin.Virol. 35:216-220 (2006).
Pass, et al., A subunit cytomegalovirus vaccine based on recombinant envelope glycoprotein B and a new adjuvant. J.Infect.Dis. (180):970-975 (1999).
Pass, et al., Vaccine prevention of maternal cytomegalovirus infection. N.Engl.J.Med. (360):1191-1199 (2009).
Patrone, et al., Human cytomegalovirus UL130 protein promotes endothelial cell infection through a producer cell modification of the virion. J Virol. (79):8361-8373 (2005).
Peters, "Integrating epitope data into the emerging web of biomedical knowledge resources," Nat. Rev. Immunol. 7:485-490 (2007).
Peters et al, "Studies of a prophylactic HIV-1 vaccine candidate based on modified vaccinia virus Ankara (MVA) with and without DNA priming: effects of dosage and route on safety and immunogenicity," Vaccine 25:2120-7 (2007).
Plachter et al, "Analysis of proteins encoded by IE regions 1 and 2 of human cytomegalovirus using monoclonal antibodies generated against recombinant antigens," Virology 193:642-52 (1993).
Platcher, et al., Cell types involved in replication and distribution of human cytomegalovirus. Adv Virus Res. (46):195-261 (1996).
Plotkin, et al., Candidate cytomegalovirus strain for human vaccination. Infect Immun. (12):521-527 (1975).
Plotkin, et al., Effect of Towne live virus vaccine on cytomegalovirus disease after renal transplant. Ann Intern Med. (114):525-531 (1991).
Plotkin, et al., Protective effects of Towne cytomegalovirus vaccine against low-passage cytomegalovirus administered as a challenge. J Infect Dis. (159):860-865 (1989).
Ramirez et al, "Biology of attenuated modified vaccinia virus Ankara recombinant vector in mice: Virus fate and activation of B- and T-cell immune responses in comparison with the Western Reserve strain and advantages as a vaccine," J Virol 74:923-33 (2000).
Rasmussen, et al., Antibody response to human cytomegalovirus glycoproteins gB and gH after natural infection in humans. J.Infect. Dis. (164):835-842 (1991).
Reap et al, "Cellular and humoral immune responses to alphavirus replicon vaccines expressing cytomegalovirus pp65, IE1, and gB proteins," Clinical Vaccine Immunology 14(6):748-755 (2007).
Reddehase et al, "CD8-positive T lymphoctyes specific for murine cytomegalovirus immediate-early antigens mediate protective immunity," J. Virol. 61:3102-3108 (1987).
Revello, et al., Human cytomegalovirus tropism for endothelial/epithelial cells: scientific background and clinical implications. Rev.Med.Virol. (20):136-155 (2010).
Rivailler, et al., Genomic sequence of rhesus cytomegalovirus 180.92: insights into the coding potential of rhesus cytomegalovirus. J.Virol. (80):4179-4182 (2006).
Rochlitz et al, "Phase I immunotherapy with a modified vaccinia virus (MVA) expressing human MUC1 as antigen-specific immunotherapy in patients with MUC1-positive advanced cancer," J Gene Med 5:690-9 (2003).

(56) References Cited

OTHER PUBLICATIONS

Rohrlich et al, "HLA-BL0702 transgenic, H-2KbDb double-knockout mice: phenotypical and functional characterization in response to influenza virus," Int. Immunol. 15:765-772 (2003).
Ryckman, et al., Human cytomegalovirus entry into epithelial and endothelial cells depends on genes UL128 to UL150 and occurs by endocytosis and low-pH fusion. J Virol. (80):710-722 (2006).
Ryckman, et al., Characterization of the human cytomegalovirus gH/gL/UL128-131 complex that mediates entry into epithelial and endothelial cells. J.Virol. (82):60-70 (2008).
Ryckman, et al., HCMV gH/gL/UL128-131interferes with virus entry into epithelial cells: evidence for cell type-specific receptors. Proc.Natl.Acad.Sci.U.S.A (105):14118-14123 (2008).
Ryckman, et al., Human cytomegalovirus TR strain glycoprotein O acts as a chaperone promoting gH/gL incorporation into virions but is not present in virions. J.Virol. (84):2597-2609 (2010).
Saccoccio, et al., Peptides from cytomegalovirus UL130 and UL131 proteins induce high titer antibodies that block viral entry into mucosal epithelial cells. Vaccine. (29):2705-2711 (2011).
Sandstrom et al, "Broad immunogenicity of a multigene. Multiclade HIV-1 DNA vaccine boosted with heterologous HIV-1 recombinant modified vaccinia virus Ankara," J Infect Dis; 198(10):1482-90 (2008).
Schleiss et al, "Preconceptual administration of an alphavirus replicon UL83 (pp65 homolog) vaccine induces humoral and cellular immunity and improves pregnancy outcome in the guinea pig model of congenital cytomegalovirus infection," J. Infect. Dis. 195:789-798 (2007).
Schleiss, et al., Role of breast milk in acquisition of cytomegalovirus infection: recent advances. Curr Opin Pediatr. (18):48-52 (2006).
Schleiss, et al., Nonprimate models of congenital cytomegalovirus (CMV) infection: gaining insight into pathogenesis and prevention of disease in newborns. ILAR.J. (47):65-72 (2006).
Schleiss, et al., Cytomegalovirus vaccines and methods of production (WO20009049138): the emerging recognition of the importance of virus neutralization at the epithelial/endothelial interface. Expert.Opin.Ther.Pat (20):597-602 (2010).
Schleiss, et al., Analysis of the nucleotide sequence of the guinea pig cytomegalovirus (GPCMV) genome. Virol.J. (5):139 (2008).
Schmelz et al, "Assembly of vaccinia virus: the second wrapping cisterna is derived from the trans Golgi network," J Virol 1994; 68(1):130-47 (1994).
Sequar, et al., Experimental coinfection of rhesus macaques with rhesus cytomegalovirus and simian immunodeficiency virus: pathogenesis. J.Virol. (76):7661-7671 (2002).
Shimamura, et al., Human cytomegalovirus infection elicits a glycoprotein M (gM)/gN-specific virus-neutralizing antibody response. J.Virol. (80):4591-4600 (2006).
Sinclair et al, "CMV antigen-specific CD4+ and CD8+ T Cell IFNgamma expression and proliferation responses in healthy CMV-seropositive individuals," Viral Immunol. 17:445-454 (2004).
Sinclair et al, "Protective immunity to cytomegalovirus (CMV) retinitis in AIDS is associated with CMV-specific T cells that express interferon-gamma and interleukin-2 and have a CD8+ cell early maturational phenotype," J. Infect. Dis. 194:1537-1546 (2006).
Sinzger, et al., Cytomegalovirus cell tropism. Curr.Top.Microbiol. Immunol. (325):63-83 (2008).
Song et al, "An MVA vaccine overcomes tolerance to human p53 in mice and humans," Canc. Immunol. Immunother. 56(8):1193-205 (2007).
Stagno, et al., Cervical cytomegalovirus excretion in pregnant and nonpregnant women: suppression in early gestation. J Infect Dis. (131):522-527 (1975).
Stickl et al, "MVA vaccination against smallpox: clinical tests with an attenuated live vaccinia virus strain (MVA) (author's translation)," Dtsch. Med. Wochenschr 99:2386-2392 (1974).
Stittelaar et al, "Protective immunity in macaques vaccinated with a modified vaccinia virus Ankara-based measles virus vaccine in the presence of passively acquired antibodies." J Virol; 74(9):4236-43 (2000).
Stittelaar et al, "Safety of modified vaccinia virus Ankara (MVA) in immune-suppressed macaques," Vaccine 19:3700-9 (2001).
Stratton, et al., Vaccines for the 21st Century: A tool for Decisionmaking. Bethesda: National Academy Press. (2001).
Sung, H., et al., "Update on the Current Status of Cytomegalovirus Vaccines," Expert Rev. Vaccines 9(11):1303-1314 (2010).
Sutter, "Vaccinia vectors as candidate vaccines: the development of modified vaccinia virus Ankara for antigen delivery," Curr Drug Targets Infect Disord.; 3(3):263-71 (2003).
Sylwester et al, "Broadly targeted human cytomegalovirus-specific CD4+ and CD8+ T cells dominate the memorycompartments of exposed subjects," J. Exp. Med. 202:673-685 (2005).
Timm et al, "Genetic stability of recombinant MVA-BN," Vaccine 24:4618-21 (2006).
Tischer, et al., Two-step red-mediated recombination for versatile high-efficiency markerless DNA manipulation in *Escherichia coli*. Biotechniques (40):191-197 (2006).
Tischer, et al., En passant mutagenesis: a two step markerless red recombination system. Methods Mol.Biol. (634):421-430 (2010).
Tobery et al, "Targeting of HIV-1 antigens for rapid intracellular degradation enhances cytotoxic T lymphocyte (CTL) recognition and the induction of de novo CTL responses in vivo after immunization," J Exp Med; 185(5):909-20 (1997).
Uhde-Holzem et al, "Genetic stability of recombinant potato virusXvirus vectors presenting foreign epitopes," Arch Virol; 152(4):805-11 (2007).
Urban, et al., Glycoprotein H of human cytomegalovirus is a major antigen for the neutralizing humoral immune response. J.Gen.Virol. 77 ( Pt 7):1537-1547 (1996).
Van Kooten, et al., CD40-CD40 ligand. J.Leukoc.Biol. (67):2-17 (2000).
Vanarsdall, et al., Human cytomegalovirus entry into cells. Curr. Opin.Virol. (2):37-42 (2012).
Vanarsdall, et al., Human cytomegalovirus glycoproteins gB and gH/gL mediate epithelial cell-cell fusion when expressed either in cis or in trans. J.Virol. (82):11837-11850 (2008).
Walter et al, "Reconstitution of cellular immunity against cytomegalovirus in recipients of allogeneic bone marrow by transfer of T-cell clones from the donor," N. Engl. J. Med. 333:1038-1044 (1995).
Wang, Z., et al., "A Fusion Protein of HCMV IE1 exon4 and IE2 exon5 Stimulates Potent Cellular Immunity in an MVA Vaccine Vector," Virology 377(2):379-390 (2008).
Wang et al, "A fusion protein of HCMV IE1 exon4 and IE2 exon5 stimulates potent cellular immunity in an MVA vaccine vector," Virology 377:379-390 (2008).
Wang et al, "Attenuated poxvirus expressing three immunodominant CMV antigens as a vaccine strategy for CMV infection," J Clin Virol 35:324-31 (2006).
Wang et al, "Attenuated Poxviruses Generate Clinically Relevant Frequencies of CMV-Specific T cells," Blood 104:847-856 (2004).
Wang et al, "Modified H5 promoter improves stability of insert genes while maintaining immunogeneticity during extended passage of genetically engineered MVA vaccines." Vaccine 28:1547-1557 (2010).
Wang et al, "Recombinant modified vaccinia virus Ankara expressing a soluble form of glycoprotein B causes durable immunity and neutralizing antibodies against multiple strains of human cytomegalovirus," J Virol 78:3965-76 (2004).
Wang et al, "Vaccine properties of a novel marker gene-free recombinant modified vaccinia Ankara expressing immunodominant CMV antigens pp65 and IE1," Vaccine 25:1132-41 (2007).
Wang, et al., Quantitative analysis of neutralizing antibody response to human cytomegalovirus in natural infection. Vaccine. (29):9075-9080 (2011).
Wang, et al., Human cytomegalovirus UL131 open reading frame is required for epithelial cell tropism. J.Virol. (79):10330-10330 (2005).
Wang, et al., Human cytomegalovirus virion protein complex required for epithelial and endothelial cell tropism. Proc.Natl.Acad.Sci.U. S.A (102):18153-18158 (2005).
Weil, S. C., et al., "Avipoxviruses: Infection Biology and Their Use as Vaccine Vectors," Virology Journal 8:49 (2011).

(56) References Cited

OTHER PUBLICATIONS

Werner et al, "Studies on poxvirus infection in irradiated animals," Arch Virol 64:247-56 (1980).

White et al, "The IE2 60-kilodalton and 40-kilodalton proteins are dispensable for human cytomegalovirus replication but are required for efficient delayed early and late gene expression and production of infectious virus," J. Virol. 81:2573-2583 (2007).

Wilck, et al., Interim Analysis of a Phase 2 Trial of TransVax™, aTherapeutic DNA Vaccine for Control of Cytomegalovirus in Transplant Recipients [abstract]. ICAAC (2010).

Wille, et al., A human cytomegalovirus gO-null mutant fails to incorporate gH/gL into the virion envelope and is unable to enter fibroblasts and epithelial and endothelial cells. J.Virol. (84):2585-2596 (2010).

Wills et al, "The human CTL response to cytomegalovirus is dominated by structural protein pp65: frequency, specificity, and T cell receptor usage of pp65-specific CTL," J. Virol. 70:7560-7579 (1996).

Wloch, et al., Safety and immunogenicity of a bivalent cytomegalovirus DNA vaccine in healthy adult subjects. J Infect Dis.(197):1634-1642 (2008).

Wussow, et al., A vaccine based on the rhesus cytomegalovirus UL128 complex induces broadly neutralizing antibodies in rhesus macaques. J Virol. 87(3):1322-1332 (2013).

Wyatt et al, "Correlation of immunogenicities and in vitro expression levels of recombinant modified vaccinia virus Ankara HIV vaccines," Vaccine 26:486-93 (2008).

Wyatt et al, "Development of a replication-deficient recombinant vaccinia virus vaccine effective against parainfluenza virus 3 infection in an animal model," Vaccine 14:!451-58 (1996).

Wyatt et al, "Elucidating and minimizing the loss by recombinant vaccinia virus of human immunodeficiency virus gene expression resulting from spontaneous mutation and positive selection," J Virol; 83(14):7176-84 (2009).

Wyatt et al, "Enhanced cell surface expression, immunogenicity and genetic stability resulting from a spontaneous truncation of HIV Env expressed by a recombinant MVA," Virology 372(2):260-72 (Epub Nov. 28, 2007) (2007).

Wyatt et al, "Multiprotein HIV type 1 clade B DNA and MVA vaccines: construction, expression, and immunogenicity in rodents of the MVA component," AIDS Res. Hum. Retrovi. 20:645-653 (2004).

Yamada, et al., Characterization of the guinea pig cytomegalovirus genome locus that encodes homologs of human cytomegalovirus major immediate-early genes, UL128, and UL130. Virology (391):99-106 (2009).

Yu, et al., Functional map of human cytomegalovirus AD169 defined by global mutational analysis. Proc Natl Acad Sci U S A. (100):12396-12401 (2003).

Yue, et al., Rhesus cytomegalovirus a nonhuman primate model for the study of human cytomegalovirus. Adv.Virus Res. (72):207-226 (2008).

Yue, et al., Antibody responses to rhesus cytomegalovirus glycoprotein B in naturally infected rhesus macaques. J.Gen.Virol. (84):3371-3379 (2003).

Yue et al, "Evaluation of recombinant modified vaccinia Ankara virus-based rhesus cytomegalorvirus vaccines in rhesus macaques," Med. Microbiol. Immunol. 197:117-123 (2008).

Yue et al, "Immunogenicity and protective efficacy of DNA vaccines expressing rhesus cytomegalovirus glycoprotein B, phosphoprotein 65-2, and viral interleukin-10 in rhesus macaques," J. Virol. 81:1095-1109 (2007).

Zaia, "Status of cytomegalovirus prevention and treatment in 2000," Hematology 2000:339-355 (2001).

Zaia et al, "Prevention and management of CMV-related problems after hematopoietic stem cell transplantation," Bone Marrow Transplant. 29:633-638 (2002).

Zhang et al, "Direct comparison of antigen production and induction of apoptosis by canarypox virus- and modified vaccinia virus Ankara human immunodeficiency virus vaccine vectors," J. Virol. 81:7022-7033 (2007).

Zhang, et al., Detection of cytomegalovirus infection during clinical trials of glycoprotein B vaccine. Vaccine (23):507-510 (2004).

Zhang, et al., Detection of cytomegalovirus infection during a vaccine clinical trial in healthy young women: seroconversion and viral shedding. J.Clin.Virol. (35):338-342 (2006).

United States Patent and Trademark Office, International Search Report and Written Opinion dated Aug. 30, 2013 for PCT/US2013/032554.

\* cited by examiner mH5-IEfusion-pZWIIA (GUS) plasmid map:

mH5-pp65-pLW51(GUS) plasmid map:

Fig. 8A      H5-IEfusion-pZWIIA (GUS) plasmid DNA sequence

```
   1 CCTCCTGAAA AACTGGAATT TAATACACCA TTTGTGTTCA TCATCAGACA TGATATTACT
  61 GGATTTATAT TGTTTATGGG TAAGGTAGAA TCTCCTTAAT ATGGGTACGG TGTAAGGAAT
 121 CATTATTTTA TTTATATTGA TGGGTACGTG AAATCTGAAT TTTCTTAATA AATATTATTT
 181 TTATTAAATG TGTATATGTT GTTTTGCGAT AGCCATGTAT CTACTAATCA GATCTATTAG
 241 AGATATTATT AATTCTGGTG CAATATGACA AAAATTATAC ACTAATTAGC GTCTCGTTTC
 301 AGACATGGAT CTGTCACGAA TTAATACTTG GAAGTCTAAG CAGCTGAAAA GCTTTCTCTC
 361 TAGCAAAGAT GCATTTAAGG CGGATGTCCA TGGACATAGT GCCTTGTATT ATGCAATAGC
 421 TGATAATAAC GTGCGTCTAG TATGTACGTT GTTGAACGCT GGAGCATTGA AAAATCTTCT
 481 AGAGAATGAA TTTCCATTAC ATCAGGCAGC CACATTGGAA GATACCAAAA TAGTAAAGAT
 541 TTTGGCTATT CAGTGGACTG GATGATTCGA GGTACCGACT ATTGTTCTAT ATTATATATG
 601 GTTGTTGATG GATCTGTGAT GCATGCAATA GCTGATAATA GAACTTACGC AAATATTAGC
 661 AAAAATATAT TAGACAATAC TACAATTAAC GATGAGTGTA GATGCTGTTA TTTTGAACCA
 721 CAGATTAGGA TTCTTGATAG AGATGAGATG CTCAATGGAT CATCGTGTGA TATGAACAGA
 781 CATTGTATTA TGATGAATTT ACCTGATGTA GGCGAATTTG GATCTAGTAT GTTGGGGAAA
 841 TATGAACCTG ACATGATTAA GATTGCTCTT TCGGTGGCTG GGTACCAGGC GCGCATTTCA
 901 TTTTGTTTTT TTCTATGCTA TAAATGGTAC GTCCTGTAGA AACCCCAACC CGTGAAATCA
 961 AAAAACTCGA CGGCCTGTGG GCATTCAGTC TGGATCGCGA AAACTGTGGA ATTGATCAGC
1021 GTTGGTGGGA AAGCGCGTTA CAAGAAAGCC GGGCAATTGC TGTGCCAGGC AGTTTTAACG
1081 ATCAGTTCGC CGATGCAGAT ATTCGTAATT ATGCGGGCAA CGTCTGGTAT CAGCGCGAAG
1141 TCTTTATACC GAAAGGTTGG GCAGGCCAGC GTATCGTGCT GCGTTTCGAT GCGGTCACTC
1201 ATTACGGCAA AGTGTGGGTC AATAATCAGG AAGTGATGGA GCATCAGGGC GGCTATACGC
1261 CATTTGAAGC CGATGTCACG CCGTATGTTA TTGCCGGGAA AAGTGTACGT ATCACCGTTT
1321 GTGTGAACAA CGAACTGAAC TGGCAGACTA TCCCGCCGGG AATGGTGATT ACCGACGAAA
1381 ACGGCAAGAA AAAGCAGTCT TACTTCCATG ATTTCTTTAA CTATGCCGGA ATCCATCGCA
1441 GCGTAATGCT CTACACCACG CCGAACACCT GGGTGGACGA TATCACCGTG GTGACGCATG
1501 TCGCGCAAGA CTGTAACCAC GCGTCTGTTG ACTGGCAGGT GGTGGCCAAT GGTGATGTCA
1561 GCGTTGAACT GCGTGATGCG GATCAACAGG TGGTTGCAAC TGGACAAGGC ACTAGCGGGA
1621 CTTTGCAAGT GGTGAATCCG CACCTCTGGC AACCGGGTGA AGGTTATCTC TATGAACTGT
1681 GCGTCACAGC CAAAAGCCAG ACAGAGTGTG ATATCTACCC GCTTCGCGTC GGCATCCGGT
1741 CAGTGGCAGT GAAGGGCGAA CAGTTCCTGA TTAACCACAA ACCGTTCTAC TTTACTGGCT
1801 TTGGTCGTCA TGAAGATGCG GACTTGCGTG GCAAAGGATT CGATAACGTG CTGATGGTGC
1861 ACGACCACGC ATTAATGGAC TGGATTGGGG CCAACTCCTA CCGTACCTCG CATTACCCTT
1921 ACGCTGAAGA GATGCTCGAC TGGGCAGATG AACATGGCAT CGTGGTGATT GATGAAACTG
1981 CTGCTGTCGG CTTTAACCTC TCTTTAGGCA TTGGTTTCGA AGCGGGCAAC AAGCCGAAAG
2041 AACTGTACAG CGAAGAGGCA GTCAACGGGG AAACTCAGCA AGCGCACTTA CAGGCGATTA
2101 AAGAGCTGAT AGCGCGTGAC AAAAACCACC CAAGCGTGGT GATGTGGAGT ATTGCCAACG
2161 AACCGGATAC CCGTCCGCAA GGTGCACGGG AATATTTCGC GCCACTGGCG GAAGCAACGC
2221 GTAAACTCGA CCCGACGCGT CCGATCACCT GCGTCAATGT AATGTTCTGC GACGCTCACA
2281 CCGATACCAT CAGCGATCTC TTTGATGTGC TGTGCCTGAA CCGTTATTAC GGATGGTATG
2341 TCCAAAGCGG CGATTTGGAA ACGGCAGAGA AGGTACTGGA AAAGAACTT CTGGCCTGGC
2401 AGGAGAAACT GCATCAGCCG ATTATCATCA CCGAATACGG CGTGGATACG TTAGCCGGGC
2461 TGCACTCAAT GTACACCGAC ATGTGGAGTG AAGAGTATCA GTGTGCATGG CTGGATATGT
2521 ATCACCGCGT CTTTGATCGC GTCAGCGCCG TCGTCGGTGA ACAGGTATGG AATTTCGCCG
2581 ATTTTGCGAC CTCGCAAGGC ATATTGCGCG TTGGCGGTAA CAAGAAAGGG ATCTTCACTC
2641 GCGACCGCAA ACCGAAGTCG GCGGCTTTTC TGCTGCAAAA ACGCTGGACT GGCATGAACT
2701 TCGGTGAAAA ACCGCAGCAG GGAGGCAAAC AATGAGAGCT CGGTTGTTGA TGGATCTGTG
2761 ATGCATGCAA TAGCTGATAA TAGAACTTAC GCAAATATTA GCAAAAATAT ATTAGACAAT
2821 ACTACAATTA ACGATGAGTG TAGATGCTGT TATTTTGAAC CACAGATTAG GATTCTTGAT
2881 AGAGATGAGA TGCTCAATGG ATCATCGTGT GATATGAACA GACATTGTAT TATGATGAAT
2941 TTACCTGATG TAGGCGAATT TGGATCTAGT ATGTTGGGGA AATATGAACC TGACATGATT
3001 AAGATTGCTC TTTCGGTGGC TGGCGGCCCG CTCGAGAAAA ATTGAAAATA AATACAAAGG
3061 TTCTTGAGGG TTGTGTTAAA TTGAAAGCGA GAAATAATCA TAAATAAGCC ACCACCGTTT
3121 AAACGCCACC ACAATGGTCA AACAGATTAA GGTTCGAGTG ACATGGTGC GGCATAGAAT
3181 CAAGGAGCAC ATGCTGAAAA AATATACCCA GACGGAAGAG AAATTCACTG GCGCCTTTAA
3241 TATGATGGGA GGATGTTTGC AGAATGCCTT AGATATCTTA GATAAGGTTC ATGAGCCTTT
3301 CGAGGAGATG AAGTGTATTG GGCTAACTAT GCAGAGCATG TATGAGAACT ACATTGTACC
3361 TGAGGATAAG CGGGAGATGT GGATGGCTTG TATTAAGGAG CTGCATGATG TGAGCAAGGG
3421 CGCCGCTAAC AAGTTGGGGG GTGCACTGCA GGCTAAGGCC CGTGCTAAAA GGATGAACT
3481 TAGGAGAAAG ATGATGTATA TGTGCTACAG GAATATAGAG TTCTTTACCA GAACTCAGC
3541 CTTCCCTAAG ACCACCAATG GCTGCAGTCA GGCCATGGCG GCACTGCAGA ACTTGCCTCA
```

Fig. 8A (continued)

```
3601 GTGCTCCCCT GATGAGATTA TGGCTTATGC CCAGAAAATA TTTAAGATTT TGGATGAGGA
3661 GAGAGACAAG GTGCTCACGC ACATTGATCA CATATTTATG GATATCCTCA CTACATGTGT
3721 GGAAACAATG TGTAATGAGT ACAAGGTCAC TAGTGACGCT TGTATGATGA CCATGTACGG
3781 GGGCATCTCT CTCTTAAGTG AGTTCTGTCG GGTGCTGTGC TGCTATGTCT TAGAGGAGAC
3841 TAGTGTGATG CTGGCCAAGC GGCCTCTGAT AACCAAGCCT GAGGTTATCA GTGTAATGAA
3901 GCGCCGCATT GAGGAGATCT GCATGAAGGT CTTTGCCCAG TACATTCTGG GGGCCGATCC
3961 TCTGAGAGTC TGCTCTCCTA GTGTGGATGA CCTACGGGCC ATCGCCGAGG AGTCAGATGA
4021 GGAAGAGGCT ATTGTAGCCT ACACTTTGGC CACCGCTGGT GTCAGCTCCT CTGATTCTCT
4081 GGTGTCACCC CCAGAGTCCC CTGTACCCGC GACTATCCCT CTGTCCTCAG TAATTGTGGC
4141 TGAGAACAGT GATCAGGAAG AAAGTGAGCA GAGTGATGAG GAAGAGGAGG AGGGTGCTCA
4201 GGAGGAGCGG GAGGACACTG TGTCTGTCAA GTCTGAGCCA GTGTCTGAGA TAGAGGAAGT
4261 TGCCCCAGAG GAAGAGGAGG ATGGTGCTGA GGAACCCACC GCCTCTGGAG GCAAGAGCAC
4321 CCACCCTATG GTGACTAGAA GCAAGGCTGA CCAGGGTGAC ATCCTCGCCC AGGCTGTCAA
4381 TCATGCCGGT ATCGATTCCA GTAGCACCGG CCCCACGCTG ACAACCCACT CTTGCAGCGT
4441 TAGCAGCGCC CCTCTTAACA AGCCGACCCC CACCAGCGTC GCGGTTACTA ACACTCCTCT
4501 CCCCGGGGCA TCCGCTACTC CCGAGCTCAG CCCGCGTAAG AAACCGCGCA AAACCACGCG
4561 TCCTTTCAAG GTGATTATTA AACCGCCGT GCCTCCCGCG CCTATCATGC TGCCCCTCAT
4621 CAAACAGGAA GACATCAAGC CCGAGCCCGA CTTTACCATC CAGTACCGCA ACAAGATTAT
4681 CGATACCGCC GGCTGTATCG TGATCTCTGA TAGCGAGGAA GAACAGGGTG AAGAAGTCGA
4741 AACCCGCGGT GCTACCGCGT CTTCCCCTTC CACCGGCAGC GGCACGCCGC GAGTGACCTC
4801 TCCCACGCAC CCGCTCTCCC AGATGAACCA CCCTCCTCTT CCCGATCCCT TGGGCCGGCC
4861 CGATGAAGAT AGTTCCTCTT CGTCTTCCTC CTCCTGCAGT TCGGCTTCGG ACTCGGAGAG
4921 TGAGTCCGAG GAGATGAAAT GCAGCAGTGG CGGAGGAGCA TCCGTGACCT CGAGCCACCA
4981 TGGGCGCGGC GGTTTTGGTG GCGCGGCCTC CTCCTCTCTG CTGAGCTGCG GCCATCAGAG
5041 CAGCGGCGGG GCGAGCACCG GACCCCGCAA GAAGAAGAGC AAACGCATCT CCGAGTTGGA
5101 CAACGAGAAG GTGCGCAATA TCATGAAAGA TAAGAACACC CCCTTCTGCA CACCCAACGT
5161 GCAGACTCGG CGGGGTCGCG TCAAGATTGA CGAGGTGAGC CGCATGTTCC GCAACACCAA
5221 TCGCTCTCTT GAGTACAAGA ACCTGCCCTT CACGATTCCC AGTATGCACC AGGTGTTAGA
5281 TGAGGCCATC AAAGCCTGCA AAACCATGCA GGTGAACAAC AAGGGCATCC AGATTATCTA
5341 CACCCGCAAT CATGAGGTGA AGAGTGAGGT GGATGCGGTG CGGTGTCGCC TGGGCACCAT
5401 GTGCAACCTG GCCCTCTCCA CTCCCTTCCT CATGGACGAC ACCATGCCCG TGACACATCC
5461 ACCCGAAGTG GCGCAGCGCA CAGCCGATGC TTGTAACGAA GGCGTCAAGG CCGCGTGGAG
5521 CCTCAAAGAA TTGCACACCC ACCAATTATG CCCCCGTTCC TCCGATTACC GCAACATGAT
5581 CATCCACGCT GCCACCCCCG TGGACCTGTT GGGCGCTCTC AACCTGTGCC TGCCCCTGAT
5641 GCAAAAGTTT CCCAAACAGG TCATGGTGCG CATCTTCTCC ACCAACCAGG GTGGGTTCAT
5701 GCTGCCTATC TACGAGACGG CCGCGAAGGC CTACGCCGTG GGGCAGTTTG AGCAGCCCAC
5761 CGAGACCCCT CCCGAAGACC TGGACACCCT GAGCCTGGCC ATCGAGGCAG CCATCCAGGA
5821 CCTGAGGAAC AAGTCTCAGT AAAATAAAGG CGCGCCATAA AAATTTTTAT ACTAGTGTAC
5881 CGCGGTCGAA TCGATTTAAT TAACGATGCT AGCATTGTCG ACGGTGGTGG CGCGGCCGCC
5941 AGTGTGATGG ATATCTGCAG AATTCGGCTT GGGGGGCTGC AGGTGGATGC GATCATGACG
6001 TCCTCTGCAA TGGATAACAA TGAACCTAAA GTACTAGAAA TGGTATATGA TGCTACAATT
6061 TTACCCGAAG GTAGTAGCAT GGATTGTATA ACAGACACA TCAATATGTG TATACAACGC
6121 ACCTATAGTT CTAGTATAAT TGCCATATTG GATAGATTCC TAATGATGAA CAAGGATGAA
6181 CTAAATAATA CACAGTGTCA TATAATTAAA GAATTTATGA CATACGAACA AATGGCGATT
6241 GACCATTATG GAGAATATGT AAACGCTATT CTATATCAAA TTCGTAAAAG ACCTAATCAA
6301 CATCACACCA TTAATCTGTT TAAAAAAATA AAAAGAACCC GGTATGACAC TTTTAAAGTG
6361 GATCCCGTAG AATTCGTAAA AAAAGTTATC GGATTTGTAT CTATCTTGAA CAAATATAAA
6421 CCGGTTTATA GTTACGTCCT GTACGAGAAC GTCCTGTACG ATGAGTTCAA ATGTTTCATT
6481 GACTACGTGG AAACTAAGTA TTTCTAAAAT TAATGATGCA TTAATTTTTG TATTGATTCT
6541 CAATCCTAAA AACTAAAATA TGAATAAGTA TTAAACATAG CGGTGTACTA ATTGATTTAA
6601 CATAAAAAAT AGTTGTTAAC TAATCATGAG GACTCTACTT ATTAGATATA TTCTTTGGAG
6661 AAATGACAAC GATCAAACCG GGCATGCAAG CTTGTCTCCC TATAGTGAGT CGTATTAGAG
6721 CTTGGCGTAA TCATGGTCAT AGCTGTTTCC TGTGTGAAAT TGTTATCCGC TCACAATTCC
6781 ACACAACATA CGAGCCGGAA GCATAAAGTG TAAAGCCTGG GGTGCCTAAT GAGTGAGCTA
6841 ACTCACATTA ATTGCGTTGC GCTCACTGCC CGCTTTCGAG TCGGGAAACC TGTCGTGCCA
6901 GCTGCATTAA TGAATCGGCC AACGCGCGGG GAGAGGCGGT TTGCGTATTG GCGCTCTTC
6961 CGCTTCCTCG CTCACTGACT CGCTGCGCTC GGTCGTTCGG CTGCGGCGAG CGGTATCAGC
7021 TCACTCAAAG GCGGTAATAC GGTTATCCAC AGAATCAGGG GATAACGCAG GAAAGAACAT
7081 GTGAGCAAAA GGCCAGCAAA AGGCCAGGAA CCGTAAAAAG GCCGCGTTGC TGGCGTTTTT
7141 CGATAGGCTC CGCCCCCCTG ACGAGCATCA CAAAAATCGA CGCTCAAGTC AGAGGTGGCG
```

Fig. 8A (continued)

```
7201 AAACCCGACA GGACTATAAA GATACCAGGC GTTTCCCCCT GGAAGCTCCC TCGTGCGCTC
7261 TCCTGTTCCG ACCCTGCCGC TTACCGGATA CCTGTCCGCC TTTCTCCCTT CGGGAAGCGT
7321 GGCGCTTTCT CATAGCTCAC GCTGTAGGTA TCTCAGTTCG GTGTAGGTCG TTCGCTCCAA
7381 GCTGGGCTGT GTGCACGAAC CCCCCGTTCA GCCCGACCGC TGCGCCTTAT CCGGTAACTA
7441 TCGTCTTGAG TCCAACCCGG TAAGACACGA CTTATCGCCA CTGGCAGCAG CCACTGGTAA
7501 CAGGATTAGC AGAGCGAGGT ATGTAGGCGG TGCTACAGAG TTCTTGAAGT GGTGGCCTAA
7561 CTACGGCTAC ACTAGAAGGA CAGTATTTGG TATCTGCGCT CTGCTGAAGC CAGTTACCTT
7621 CGGAAAAAGA GTTGGTAGCT CTTGATCCGG CAAACAAACC ACCGCTGGTA GCGGTGGTTT
7681 TTTTGTTTGC AAGCAGCAGA TTACGCGCAG AAAAAAAGGA TCTCAAGAAG ATCCTTTGAT
7741 CTTTTCTACG GGGTCTGACG CTCAGTGGAA CGAAAACTCA CGTTAAGGGA TTTTGGTCAT
7801 GAGATTATCA AAAAGGATCT TCACCTAGAT CCTTTTAAAT TAAAAATGAA GTTTTAAATC
7861 AATCTAAAGT ATATATGAGT AAACTTGGTC TGACAGTTAC CAATGCTTAA TCAGTGAGGC
7921 ACCTATCTCA GCGATCTGTC TATTTCGTTC ATCCATAGTT GCCTGACTCC CCGTCGTGTA
7981 GATAACTACG ATACGGGAGG GCTTACCATC TGGCCCCAGT GCTGCAATGA TACCGCGAGA
8041 CCCACGCTCA CCGGCTCCAG ATTTATCAGC AATAAACCAG CCAGCCGGAA GGGCCGAGCG
8101 CAGAAGTGGT CCTGCAACTT TATCCGCCTC CATCCAGTCT ATTAATTGTT GCCGGGAAGC
8161 TAGAGTAAGT AGTTCGCCAG TTAATAGTTT GCGCAACGTT GTTGGCATTG CTACAGGCAT
8221 CGTGGTGTCA CGCTCGTCGT TTGGTATGGC TTCATTCAGC TCCGGTTCCC AACGATCAAG
8281 GCGAGTTACA TGATCCCCCA TGTTGTGCAA AAAAGCGGTT AGCTCCTTCG GTCCTCCGAT
8341 CGTTGTCAGA AGTAAGTTGG CCGCAGTGTT ATCACTCATG GTTATGGCAG CACTGCATAA
8401 TTCTCTTACT GTCATGCCAT CCGTAAGATG CTTTTCTGTG ACTGGTGAGT ACTCAACCAA
8461 GTCATTCTGA GAATAGTGTA TGCGGCGACC GAGTTGCTCT TGCCCGGCGT CAATACGGGA
8521 TAATACCGCG CCACATAGCA GAACTTTAAA AGTGCTCATC ATTGGAAAAC GTTCTTCGGG
8581 GCGAAAACTC TCAAGGATCT TACCGCTGTT GAGATCCAGT TCGATGTAAC CCACTCGTGC
8641 ACCCAACTGA TCTTCAGCAT CTTTTACTTT CACCAGCGTT TCTGGGTGAG CAAAAACAGG
8701 AAGGCAAAAT GCCGCAAAAA AGGGAATAAG GGCGACACGG AAATGTTGAA TACTCATACT
8761 CTTCCTTTTT CAATATTATT GAAGCATTTA TCAGGGTTAT TGTCTCATGA GCGGATACAT
8821 ATTTGAATGT ATTTAGAAAA ATAAACAAAT AGGGGTTCCG CGCACATTTC CCCGAAAAGT
8881 GCCACCTGAC GTCTAAGAAA CCATTATTAT CATGACATTA ACCTATAAAA ATAGGCGTAT
8941 CACGAGGCCC TTTCGTCTCG CGCGTTTCGG TGATGACGGT GAAAACCTCT GACACATGCA
9001 GCTCCCGGAG ACGGTCACAG CTTGTCTGTA AGCGGATGCC GGGAGCAGAC AAGCCCGTCA
9061 GGGCGCGTCA GCGGGTGTTG GCGGGTGTCG GGCTGGCTT AACTATGCGG CATCAGAGCA
9121 GATTGTACTG AGAGTGCACC ATATGCGGTG TGAAATACCG CACAGATGCG TAAGGAGAAA
9181 ATACCGCATC AGGCGCCATT CGCCATTCAG GCTGCGCAAC TGTTGGGAAG GGCGATCGGT
9241 GCGGGCCTCT TCGCTATTAC GCCAGCTGGC GAAAGGGGGA TGTGCTGCAA GGCGATTAAG
9301 TTGGGTAACG CCAGGGTTTT CCCAGTCACG ACGTTGTAAA ACGACGGCCA GTGAATTGGA
9361 TTTAGGTGAC ACTATAGAAT ACGAATTC
```

Fig. 8B    mH5-pp65-pLW51(GUS) plasmid DNA sequence

```
   1 GAATTCGTTG GTGGTCGCCA TGGATGGTGT TATTGTATAC TGTCTAAACG CGTTAGTAAA
  61 ACATGGCGAG GAAATAAATC ATATAAAAAA TGATTTCATG ATTAAACCAT GTTGTGAAAA
 121 AGTCAAGAAC GTTCACATTG GCGGACAATC TAAAACAAT ACAGTGATTG CAGATTTGCC
 181 ATATATGGAT AATGCGGTAT CCGATGTATG CAATTCACTG TATAAAAAGA ATGTATCAAG
 241 AATATCCAGA TTTGCTAATT TGATAAAGAT AGATGACGAT GACAAGACTC CTACTGGTGT
 301 ATATAATTAT TTTAAACCTA AAGATGCCAT TCCTGTTATT ATATCCATAG GAAAGGATAG
 361 AGATGTTTGT GAACTATTAA TCTCATCTGA TAAAGCGTGT GCGTGTATAG AGTTAAATTC
 421 ATATAAAGTA GCCATTCTTC CCATGGATGT TTCCTTTTTT ACCAAAGGAA ATGCATCATT
 481 GATTATTCTC CTGTTTGATT TCTCTATCGA TGCGGCACCT CTCTTAAGAA GTGTAACCGA
 541 TAATAATGTT ATTATATCTA GACACCAGCG TCTACATGAC GAGCTTCCGA GTTCCAATTG
 601 GTTCAAGTTT TACATAAGTA TAAAGTCCGA CTATTGTTCT ATATTATATA TGGTTGTTGA
 661 TGGATCTGTG ATGCATGCAA TAGCTGATAA TAGAACTTAC GCAAATATTA GCAAAAATAT
 721 ATTAGACAAT ACTACAATTA ACGATGAGTG TAGATGCTGT TATTTTGAAC CACAGATTAG
 781 GATTCTTGAT AGAGATGAGA TGCTCAATGG ATCATCGTGT GATATGAACA GACATTGTAT
 841 TATGATGAAT TTACCTGATG TAGGCGAATT TGGATCTAGT ATGTTGGGGA AATATGAACC
 901 TGACATGATT AAGATTGCTC TTTCGGTGGC TGGGTACCAG GCGCGCATTT CATTTTGTTT
 961 TTTTCTATGC TATAAATGGT ACGTCCTGTA GAAACCCCAA CCCGTGAAAT CAAAAAACTC
1021 GACGGCCTGT GGGCATTCAG TCTGGATCGC GAAAACTGTG GAATTGATCA GCGTTGGTGG
1081 GAAAGCGCGT TACAAGAAAG CCGGGCAATT GCTGTGCCAG GCAGTTTTAA CGATCAGTTC
1141 GCCGATGCAG ATATTCGTAA TTATGCGGGC AACGTCTGGT ATCAGCGCGA AGTCTTTATA
1201 CCGAAAGGTT GGGCAGGCCA GCGTATCGTG CTGCGTTTCG ATGCGGTCAC TCATTACGGC
1261 AAAGTGTGGG TCAATAATCA GGAAGTGATG GAGCATCAGG GCGGCTATAC GCCATTTGAA
1321 GCCGATGTCA CGCCGTATGT TATTGCCGGG AAAAGTGTAC GTATCACCGT TTGTGTGAAC
1381 AACGAACTGA ACTGGCAGAC TATCCCGCCG GGAATGGTGA TTACCGACGA AAACGGCAAG
1441 AAAAAGCAGT CTTACTTCCA TGATTTCTTT AACTATGCCG GAATCCATCG CAGCGTAATG
1501 CTCTACACCA CGCCGAACAC CTGGGTGGAC GATATCACCG TGGTGACGCA TGTCGCGCAA
1561 GACTGTAACC ACGCGTCTGT TGACTGGCAG GTGGTGGCCA ATGGTGATGT CAGCGTTGAA
1621 CTGCGTGATG CGGATCAACA GGTGGTTGCA ACTGGACAAG GCACTAGCGG ACTTTGCAA
1681 GTGGTGAATC CGCACCTCTG GCAACCGGGT GAAGGTTATC TCTATGAACT GTGCGTCACA
1741 GCCAAAAGCC AGACAGAGTG TGATATCTAC CCGCTTCGCG TCGGCATCCG GTCAGTGGCA
1801 GTGAAGGGCG AACAGTTCCT GATTAACCAC AAACCGTTCT ACTTTACTGG CTTTGGTCGT
1861 CATGAAGATG CGGACTTGCG TGGCAAAGGA TTCGATAACG TGCTGATGGT GCACGACCAC
1921 GCATTAATGG ACTGGATTGG GGCCAACTCC TACCGTACCT CGCATTACCC TTACGCTGAA
1981 GAGATGCTCG ACTGGGCAGA TGAACATGGC ATCGTGGTGA TTGATGAAAC TGCTGCTGTC
2041 GGCTTTAACC TCTCTTTAGG CATTGGTTTC GAAGCGGGCA ACAAGCCGAA AGAACTGTAC
2101 AGCGAAGAGG CAGTCAACGG GGAAACTCAG CAAGCGCACT TACAGGCGAT TAAAGAGCTG
2161 ATAGCGCGTG ACAAAAACCA CCCAAGCGTG GTGATGTGGA GTATTGCCAA CGAACCGGAT
2221 ACCCGTCCGC AAGGTGCACG GGAATATTTC GCGCCACTGG CGGAAGCAAC GCGTAAACTC
2281 GACCCGACGC GTCCGATCAC CTGCGTCAAT GTAATGTTCT GCGACGCTCA CACCGATACC
2341 ATCAGCGATC TCTTTGATGT GCTGTGCCTG AACCGTTATT ACGGATGGTA TGTCCAAAGC
2401 GGCGATTTGG AAACGGCAGA GAAGGTACTG GAAAAAGAAC TTCTGGCCTG GCAGGAGAAA
2461 CTGCATCAGC CGATTATCAT CACCGAATAC GGCGTGGATA CGTTAGCCGG GCTGCACTCA
2521 ATGTACACCG ACATGTGGAG TGAAGAGTAT CAGTGTGCAT GGCTGGATAT GTATCACCGC
2581 GTCTTTGATC GCGTCAGCGC CGTCGTCGGT GAACAGGTAT GGAATTTCGC CGATTTTGCG
2641 ACCTCGCAAG GCATATTGCG CGTTGGCGGT AACAAGAAAG GGATCTTCAC TCGCGACCGC
2701 AAACCGAAGT CGGCGGCTTT TCTGCTGCAA AAACGCTGGA CTGGCATGAA CTTCGGTGAA
2761 AAACCGCAGC AGGGAGGCAA ACAATGAGAG CTCGGTTGTT GATGGATCTG TGATGCATGC
2821 AATAGCTGAT AATAGAACTT ACGCAAATAT TAGCAAAAAT ATATTAGACA ATACTACAAT
2881 TAACGATGAG TGTAGATGCT GTTATTTTGA ACCACAGATT AGGATTCTTG ATAGAGATGA
2941 GATGCTCAAT GGATCATCGT GTGATATGAA CAGACATTGT ATTATGATGA ATTTACCTGA
3001 TGTAGGCGAA TTTGGATCTA GTATGTTGGG GAAATATGAA CCTGACATGA TTAAGATTGC
3061 TCTTTCGGTG GCTGGCGGCC CGCTCAGAA AAATTGAAAA TAAATACAAA GGTTCTTGAG
3121 GGTTGTGTTA AATTGAAAGC GAGAAATAAT CATAAATAAG CCACCACCGT TTAAACAGTC
3181 GACGGTATCG ATAAGCTTGA TATCGAATTC CTGCAGCCCG TACGCGCAGG CAGCATGGAG
3241 TCGCGCGGTC GCCGTTGTCC CGAAATGATA TCCGTACTGG GTCCATTTC GGGGCACGTG
3301 CTGAAAGCCG TGTTAGTCG CGGCGACACG CCGGTGCTGC CGCACGAGAC GCGACTCCTG
3361 CAGACGGGTA TCCACGTGCG CGTGAGCCAG CCCTCGCTGA TCCTGGTGTC GCAGTACACG
3421 CCCGACTCGA CGCCATGCCA CCGCGGCGAC AATCAGCTGC AGGTGCAGCA CACGTACTTT
3481 ACGGGCAGCG AGGTGGAGAA CGTGTCGGTC AACGTGCACA ACCCCACGGG CCGGAGCATC
3541 TGCCCCAGCC AAGAGCCCAT GTCGATCTAT GTGTACGCGC TGCCGCTCAA GATGCTGAAC
```

Fig. 8B (continued)

```
3601 ATCCCCAGCA TCAACGTGCA CCACTACCCG TCGGCGGCCG AGCGCAAACA CCGACACCTG
3661 CCCGTAGCTG ACGCTGTGAT TCACGCGTCG GGCAAGCAGA TGTGGCAGGC GCGTCTCACG
3721 GTCTCGGGAC TGGCCTGGAC GCGTCAGCAG AACCAGTGGA AAGAGCCCGA CGTCTACTAC
3781 ACGTCAGCGT TCGTGTTTCC CACCAAGGAC GTGGCACTGC GGCACGTGGT GTGCGCGCAC
3841 GAGCTGGTTT GCTCCATGGA GAACACGCGC GCAACCAAGA TGCAGGTGAT AGGTGACCAG
3901 TACGTCAAGG TGTACCTGGA GTCCTTCTGC GAGGACGTGC CCTCCGGCAA GCTCTTTATG
3961 CACGTCACGC TGGGCTCTGA CGTGGAAGAG GACCTGACGA TGACCCGCAA CCCGCAACCC
4021 TTCATGCGCC CCCACGAGCG CAACGGCTTT ACGGTGTTGT GTCCCAAAAA TATGATAATC
4081 AAACCGGGCA AGATCTCGCA CATCATGCTG GATGTGGCTT TTACCTCACA CGAGCATTTT
4141 GGGCTGCTGT GTCCCAAGAG CATCCCGGGC CTGAGCATCT CAGGTAACCT ATTGATGAAC
4201 GGGCAGCAGA TCTTCCTGGA GGTGCAAGCG ATACGCGAGA CCGTGGAACT GCGTCAGTAC
4261 GATCCCGTGG CTGCGCTCTT CTTTTTCGAT ATCGACTTGC TGCTGCAGCG CGGGCCTCAG
4321 TACAGCGAAC ACCCCACCTT CACCAGCCAG TATCGCATCC AGGGCAAGCT TGAGTACCGA
4381 CACACCTGGG ACCGGCACGA CGAGGGTGCC GCCCAGGGCG ACGACGACGT CTGGACCAGC
4441 GGATCGGACT CCGACGAGGA ACTCGTAACC ACCGAGCGCA AGACGCCCCG CGTTACCGGC
4501 GGCGGCGCCA TGGCGGGCGC CTCCACTTCC GCGGGCCGCA AACGCAAATC AGCATCCTCG
4561 GCGACGGCGT GCACGGCGGG CGTTATGACA CGCGGCCGCC TTAAGGCCGA GTCCACCGTC
4621 GCGCCCGAAG AGGACACCGA CGAGGATTCC GACAACGAAA TCCACAATCC GGCCGTGTTC
4681 ACCTGGCCGC CCTGGCAGGC CGGCATCCTG GCCCGCAACC TGGTGCCCAT GGTGGCTACG
4741 GTTCAGGGTC AGAATCTGAA GTACCAGGAG TTCTTCTGGG ACGCCAACGA CATCTACCGC
4801 ATCTTCGCCG AATTGGAAGG CGTATGGCAG CCCGCTGCGC AACCCAAACG TCGCCGCCAC
4861 CGGCAAGACG CCTTGCCCGG GCCATGCATC GCCTCGACGC CCAAAAAGCA CCGAGGTTGA
4921 TTTTTATGGC GCGCCCTGCA GGGAAAGTTT TATAGGTAGT TGATAGAACA AAATACATAA
4981 TTTTGTAAAA ATAAATCACT TTTTATACTA ATATGACACG ATTACCAATA CTTTTGTTAC
5041 TAATATCATT AGTATACGCT ACACCTTTTC CTCAGACATC TAAAAAAATA GGTGATGATG
5101 CAACTTTATC ATGTAATCGA AATAATACAA ATGACTACGT TGTTATGAGT GCTTGGTATA
5161 AGGAGCCCAA TTCCATTATT CTTTTAGCTG CTAAAAGCGA CGTCTTGTAT TTTGATAATT
5221 ATACCAAGGA TAAAATATCT TACGACTCTC CATACGATGA TCTAGTTACA ACTATCACAA
5281 TTAAATCATT GACTGCTAGA GATGCCGGTA CTTATGTATG TGCATTCTTT ATGACATCGC
5341 CTACAAATGA CACTGATAAA GTAGATTATG AAGAATACTC CACAGAGTTG ATTGTAAATA
5401 CAGATAGTGA ATCGACTATA GACATAATAC TATCTGGATC TACACATTCA CCAGAAACTA
5461 GTTAAGCTTG TCTCCCTATA GTGAGTCGTA TTAGAGCTTG GCGTAATCAT GGTCATAGCT
5521 GTTTCCTGTG TGAAATTGTT ATCCGCTCAC AATTCCACAC AACATACGAG CCGGAAGCAT
5581 AAAGTGTAAA GCCTGGGGTG CCTAATGAGT GAGCTAACTC ACATTAATTG CGTTGCGCTC
5641 ACTGCCCGCT TTCGAGTCGG GAAACCTGTC GTGCCAGCTG CATTAATGAA TCGGCCAACG
5701 CGCGGGGAGA GGCGGTTTGC GTATTGGGCG CTCTTCCGCT TCCTCGCTCA CTGACTCGCT
5761 GCGCTCGGTC GTTCGGCTGC GGCGAGCGGT ATCAGCTCAC TCAAAGGCGG TAATACGGTT
5821 ATCCACAGAA TCAGGGGATA ACGCAGGAAA GAACATGTGA GCAAAAGGCC AGCAAAAGGC
5881 CAGGAACCGT AAAAAGGCCG CGTTGCTGGC GTTTTTCGAT AGGCTCCGCC CCCCTGACGA
5941 GCATCACAAA AATCGACGCT CAAGTCAGAG GTGGCGAAAC CCGACAGGAC TATAAAGATA
6001 CCAGGCGTTT CCCCCTGGAA GCTCCCTCGT GCGCTCTCCT GTTCCGACCC TGCCGCTTAC
6061 CGGATACCTG TCCGCCTTTC TCCCTTCGGG AAGCGTGGCG CTTTCTCATA GCTCACGCTG
6121 TAGGTATCTC AGTTCGGTGT AGGTCGTTCG CTCCAAGCTG GGCTGTGTGC ACGAACCCCC
6181 CGTTCAGCCC GACCGCTGCG CCTTATCCGG TAACTATCGT CTTGAGTCCA ACCCGGTAAG
6241 ACACGACTTA TCGCCACTGG CAGCAGCCAC TGGTAACAGG ATTAGCAGAG CGAGGTATGT
6301 AGGCGGTGCT ACAGAGTTCT TGAAGTGGTG GCCTAACTAC GGCTACACTA GAAGGACAGT
6361 ATTTGGTATC TGCGCTCTGC TGAAGCCAGT TACCTTCGGA AAAAGAGTTG GTAGCTCTTG
6421 ATCCGGCAAA CAAACCACCG CTGGTAGCGG TGGTTTTTTT GTTTGCAAGC AGCAGATTAC
6481 GCGCAGAAAA AAAGGATCTC AAGAAGATCC TTTGATCTTT TCTACGGGGT CTGACGCTCA
6541 GTGGAACGAA AACTCACGTT AAGGGATTTT GGTCATGAGA TTATCAAAAA GGATCTTCAC
6601 CTAGATCCTT TTAAATTAAA AATGAAGTTT TAAATCAATC TAAAGTATAT ATGAGTAAAC
6661 TTGGTCTGAC AGTTACCAAT GCTTAATCAG TGAGGCACCT ATCTCAGCGA TCTGTCTATT
6721 TCGTTCATCC ATAGTTGCCT GACTCCCGT CGTGTAGATA ACTACGATAC GGGAGGGCTT
6781 ACCATCTGGC CCCAGTGCTG CAATGATACC GCGAGACCCA CGCTCACCGG CTCCAGATTT
6841 ATCAGCAATA AACCAGCCAG CCGGAAGGGC CGAGCGCAGA AGTGGTCCTG CAACTTTATC
6901 CGCCTCCATC CAGTCTATTA ATTGTTGCCG GGAAGCTAGA GTAAGTAGTT CGCCAGTTAA
6961 TAGTTTGCGC AACGTTGTTG GCATTGCTAC AGGCATCGTG GTGTCACGCT CGTCGTTTGG
7021 TATGGCTTCA TTCAGCTCCG GTTCCCAACG ATCAAGGCGA GTTACATGAT CCCCCATGTT
7081 GTGCAAAAAA GCGGTTAGCT CCTTCGGTCC TCCGATCGTT GTCAGAAGTA AGTTGGCCGC
7141 AGTGTTATCA CTCATGGTTA TGGCAGCACT GCATAATTCT CTTACTGTCA TGCCATCCGT
```

Fig. 8B (continued)

```
7201 AAGATGCTTT TCTGTGACTG GTGAGTACTC AACCAAGTCA TTCTGAGAAT AGTGTATGCG
7261 GCGACCGAGT TGCTCTTGCC CGGCGTCAAT ACGGGATAAT ACCGCGCCAC ATAGCAGAAC
7321 TTTAAAAGTG CTCATCATTG GAAAACGTTC TTCGGGGCGA AAACTCTCAA GGATCTTACC
7381 GCTGTTGAGA TCCAGTTCGA TGTAACCCAC TCGTGCACCC AACTGATCTT CAGCATCTTT
7441 TACTTTCACC AGCGTTTCTG GGTGAGCAAA AACAGGAAGG CAAAATGCCG CAAAAAAGGG
7501 AATAAGGGCG ACACGGAAAT GTTGAATACT CATACTCTTC CTTTTTCAAT ATTATTGAAG
7561 CATTTATCAG GGTTATTGTC TCATGAGCGG ATACATATTT GAATGTATTT AGAAAAATAA
7621 ACAAATAGGG GTTCCGCGCA CATTTCCCCG AAAAGTGCCA CCTGACGTCT AAGAAACCAT
7681 TATTATCATG ACATTAACCT ATAAAAATAG GCGTATCACG AGGCCCTTTC GTCTCGCGCG
7741 TTTCGGTGAT GACGGTGAAA ACCTCTGACA CATGCAGCTC CCGGAGACGG TCACAGCTTG
7801 TCTGTAAGCG GATGCCGGGA GCAGACAAGC CCGTCAGGGC GCGTCAGCGG GTGTTGGCGG
7861 GTGTCGGGGC TGGCTTAACT ATGCGGCATC AGAGCAGATT GTACTGAGAG TGCACCATAT
7921 GCGGTGTGAA ATACCGCACA GATGCGTAAG GAGAAAATAC CGCATCAGGC GCCATTCGCC
7981 ATTCAGGCTG CGCAACTGTT GGGAAGGGCG ATCGGTGCGG GCCTCTTCGC TATTACGCCA
8041 GCTGGCGAAA GGGGGATGTG CTGCAAGGCG ATTAAGTTGG GTAACGCCAG GGTTTTCCCA
8101 GTCACGACGT TGTAAAACGA CGGCCAGTGA ATTGGATTTA GGTGACACTA TA
``` mAb IE1

125kD IEfusion band non-specific cellular protein band mAb pp65

60kD pp65 band mAb IE mAb pp65 mAb IE

125kD IEfusion band

Non-specific cellular protein band mAb pp65

60kD pp65 band

Fig. 29

| Well | Sample Name | Detector | Reporter | Quencher | Task | Threshold | Ct | Baseline Start | Qty | Baseline End | Tm |
|---|---|---|---|---|---|---|---|---|---|---|---|
| | | | SYBR | (none) | | <0.065587> | | Auto | | Auto | |
| A2 | IEfusion STD | SYBR Green | | | Standard | | 6.28 | | 1.00e+008 | | 84.3 °C |
| A3 | IEfusion STD | SYBR Green | | | Standard | | 12.29 | | 1.00e+007 | | 84.3 °C |
| A4 | IEfusion STD | SYBR Green | | | Standard | | 19.44 | | 1000000.00 | | 84.3 °C |
| A5 | IEfusion STD | SYBR Green | | | Standard | | 22.26 | | 100000.00 | | 84.3 °C |
| A6 | IEfusion STD | SYBR Green | | | Standard | | 26.21 | | 10000.00 | | 84.3 °C |
| A7 | IEfusion STD | SYBR Green | | | Standard | | 29.78 | | 1000.00 | | 84.3 °C |
| A8 | IEfusion STD | SYBR Green | | | Standard | | 32.48 | | 100.00 | | 84.3 °C |
| A9 | IEfusion STD | SYBR Green | | | Standard | | Undet. | | | | 83.8 °C |
| A10 | IEfusion STD | SYBR Green | | | Standard | | Undet. | | | | 73.0 °C |
| A11 | no template control | SYBR Green | | | NTC | | | | | | 72.1 °C |
| A12 | positive control | SYBR Green | | | Unknown | | 8.14 | | 1.12e+008 | | 83.8 °C |
| B7 | SB1A1A1A | SYBR Green | | | Unknown | | 8.55 | | 9.00e+007 | | 84.3 °C |

GENETICALLY STABLE RECOMBINANT MODIFIED VACCINIA ANKARA (RMVA) VACCINES AND METHODS OF PREPARATION THEREOF

PRIORITY CLAIM

This application is a continuation of U.S. patent application Ser. No. 14/075,975, filed Nov. 8, 2013, issued as U.S. Pat. No. 9,675,689, issued Jun. 13, 2017, which is a divisional of U.S. patent application Ser. No. 12/795,621, filed Jun. 7, 2010, issued as U.S. Pat. No. 8,580,276, issued Nov. 12, 2013, which claims priority to U.S. Provisional Application No. 61/184,767, filed Jun. 5, 2009, both of which are incorporated herein by reference in their entireties, including drawings.

STATEMENT REGARDING FEDERALLY SPONSORED RESEARCH

The invention was made with Government support under Grant No. CA030206 awarded by the Public Health Service, Grant Nos. CA077544 and CA114889 awarded by the National Cancer Institute and Grant No. AI062496 awarded by the National Institute of Allergy and Infectious Disease. The Government has certain rights in the invention.

BACKGROUND OF THE INVENTION

Field of the Invention

The invention relates to genetically engineered modified vaccinia Ankara (MVA) or recombinant MVA (rMVA) vaccines with improved stability during extended passage. Specifically, the invention relates to genetically stable rMVA vaccines expressing cytomegalovirus (CMV) antigens such as an IEfusion protein. The invention also relates to methods for improving genetic stability and maintaining immunogenicity of rMVA vaccines after serial passage. The invention further relates to methods for the preparation of the rMVA vaccines.

Description of the Related Art

Modified vaccinia Ankara (MVA) is a genetically engineered, highly attenuated strain of vaccinia virus that does not propagate in most mammalian cells (Daftarian et al. 2005)). This property minimally impacts viral or foreign gene expression because the ability of MVA to replicate in mammalian cells is blocked at late stage viral assembly. MVA also has a large foreign gene capacity and multiple integration sites, two features that make it a desirable vector for expressing vaccine antigens. MVA has a well-established safety record and versatility for the production of heterologous proteins (Drexler et al. 2004; Ramirez et al. 2000; Stickl et al. 1974; Stittelaar et al. 2001; Werner et al. 1980). In fact, MVA-based vaccines for treatment of infectious disease and cancer have been developed and reached Phase I/II clinical trials (Acres 2007; Cosma et al. 2003; Gilbert et al. 2006; Peters et al. 2007; Rochlitz et al. 2003).

MVA has an extensive history of successful delivery into rodents, Rhesus macaques, and other non-human primates, and more recently as a clinical vaccine in cancer patients (Gilbert et al. 2006; Peters et al. 2007; Rochlitz et al. 2003). MVA is avirulent because of the loss of two important host-range genes among 25 mutations and deletions that occurred during its repeated serial passage in chicken cells (Antoine et al. 1998; Meyer et al. 1991). In contrast to NYVAC (attenuated Copenhagen strain) and ALVAC (host-range restricted Avipox), both early and late transcription are unimpaired making MVA a stronger vaccine candidate (Blanchard et al. 1998; Carroll et al. 1997a; Carroll et al. 1997b; Zhang et al. 2007). Studies in rodents and macaques affirm the safety of MVA, including protection against more virulent forms of pox viruses in challenge models and lack of persistence three months beyond initial dosing administration (deWaal et al. 2004; Earl et al. 2007; Hanke et al. 2005). Similarly, a therapeutic vaccination with MVA expressing HIV-nef demonstrated its safety in HIV-infected individuals (Cosma et al. 2003). Finally, MVA immunizations of malaria patients coinfected with HIV and/or TB confirm the safety of the vector and its ability to partially protect against a heterologous malaria strain (Gilbert et al. 2006; Moorthy et al. 2003).

These properties make MVA appealing as a vaccine vector for CMV antigens in individuals who are both severely immunosuppressed and experiencing additional complications such as malignancy or organ failure, thereby requiring a transplant. CMV infection is an important complication of transplantation procedures and affects a wide variety of individuals including newborns and HIV patients with advanced disease (Pass et al. 2006; Sinclair et al. 2006; Zaia 2002). Individuals who are previously CMV-infected or receiving a CMV-infected solid organ or stem cell allograft are candidates for a vaccine strategy that targets the cellular reservoir of the virus (Zaia et al. 2001).

Several antigens have been identified as being associated with protective immunity against CMV in transplant recipients. These include the tegument protein pp65 (UL83) and the immediate-early 1 (IE1 or UL123) global gene expression regulator (Boeckh et al. 2006; Cobbold et al. 2005; Cwynarski et al. 2001; Einsele et al. 2002; Gratama et al. 2001). In addition, a recent proteomic study of the whole CMV genome divided into overlapping peptides showed that pp65 stimulates substantial levels of both CD8+ and CD4+T cells, while IE1 mainly stimulates CD8+ T cells, and the related IE regulator referred to as IE2 (UL122) stimulates a vigorous CD8+ and a smaller CD4+ T cell memory response by a large percentage of asymptomatic CMV-positive adults (Sylwester et al. 2005). Other antigens are also recognized with robust cellular immune responses, but the evidence for these three antigens to be highly recognized in a majority of CMV-infected healthy subjects and transplant patients (Gallez-Hawkins et al. 2005) is compelling and justifies their inclusion into a vaccine to prevent viremia and control infection.

Because MVA only replicates in the cytoplasm of cells with its own vaccinia transcriptional system (which does not recognize other viral and cellular promoters), vaccinia viral promoters are used to direct foreign antigen gene expression efficiently in recombinant MVA (rMVA) systems. There are two types of vaccinia promoters widely used to direct foreign gene expression in recombinant MVA. One is pSyn, which contains both vaccinia early and late promoter sequences optimized for high level protein expression (Chakrabarti et al. 1997). The other is modified H5 promoter (mH5), which contains both native early and late vaccinia promoter regions. pSyn has stronger overall promoter activity than mH5, but the early activity of the mH5 promoter is three- to five-fold stronger than the pSyn series.

It has been reported that in vitro expression levels of foreign antigens by an rMVA vaccine are correlated with the rMVA vaccine's immunogenicity (Wyatt et al. 2008b). For example, mice immunized with the rMVAs expressing high level of human immunodeficiency virus (HIV) Env protein had about 15-fold higher titers of Env antibodies and several fold higher frequencies of Env-specific CD8+ and CD4+ T cells than mice immunized with rMVAs expressing low level of Env (84). However, after serial passage, the foreign antigen expression may be reduced and rendered unstable, which can result in diminished immunogenicity.

Thus, while MVA is an attractive viral vector for recombinant vaccine development, genetic instability and diminished immunogenicity are significant concerns after serial passage. The beneficial effect of high antigen expression levels and improved immunogenicity can be limited by the tendency of rMVA to delete genes unnecessary for its lifecycle. Previous reports suggest that instability of rMVA vaccines may be related to toxicity of foreign protein in the gene region in which it is inserted or the promoter that controls foreign protein expression (Timm et al. 2006; Wyatt et al. 2008a). For example, rMVA viruses expressing HIV Env protein and other rMVAs were found to have non-expressing mutant virus accumulation after serial passage (Wyatt et al. 2008a). rMVA expressing hemagglutinin-neuraminidase (HN) glycoproteins under control of pSyn was previously reported to replicate poorly (Wyatt et al. 1996). The non-expressing mutants and poor replications of rMVAs were reported to be likely due to toxicity of the expression of foreign proteins (Wyatt et al. 2008a; Wyatt et al. 1996). However, an rMVA expressing a mutated truncation of Env is found to have enhanced genetic stability and immunogenicity relative to rMVAs expressing a full-length Env (Wyatt et al. 2008a). Thus, a higher expression level of foreign antigens driven by a strong promoter in rMVA vaccines does not always result in higher immunogenicity after serial passage. Genetic instability and diminished immunogenicity after serial passage have not been fully understood.

It will be advantageous to develop an rMVA vaccine with stable expression of foreign protein antigens and immunogenicity after serial passage, which will enable the use of MVA as a clinical vector for a broader portfolio of infectious pathogens and cancer antigens.

SUMMARY

One embodiment is directed to a fusion cytomegalovirus (CMV) protein antigen comprising a nucleotide sequence encoding two or more antigenic portions of Immediate-Early Gene-1 or Immediate-Early Gene-2 (IEfusion), wherein the antigenic portions elicit an immune response when expressed by a vaccine. In one aspect, the IEfusion nucleotide sequence is SEQ ID NO:11.

One embodiment is directed to a vaccine comprising an immunologically effective amount of recombinant modified vaccinia Ankara (rMVA) virus which is genetically stable after serial passage and produced by a) constructing a transfer plasmid vector comprising a modified H5 (mH5) promoter operably linked to a DNA sequence encoding a heterologous foreign protein antigen, wherein the expression of said DNA sequence is under the control of the mH5 promoter; b) generating rMVA virus by transfecting one or more plasmid vectors obtained from step a) into wild type MVA virus; c) identifying rMVA virus expressing one or more heterologous foreign protein antigens using one or more selection methods for serial passage; d) conducting serial passage; e) expanding an rMVA virus strain identified by step d); and f) purifying the rMVA viruses from step e) to form the vaccine.

Another embodiment is directed to a method of modifying an immune response in a subject by administering a vaccine composition as described above to the subject. In one aspect, the subject is a human.

Yet, another embodiment is directed to a method for producing a genetically stable rMVA vaccine, comprising a) constructing a transfer plasmid vector comprising a modified H5 (mH5) promoter operably linked to a DNA sequence encoding a heterologous foreign protein antigen, wherein the expression of said DNA sequence is under the control of the mH5 promoter; b) generating rMVA virus by transfecting one or more plasmid vectors obtained from step a) into wild type MVA virus; c) identifying rMVA virus expressing one or more heterologous foreign protein antigens using one or more selection methods for serial passage; d) conducting serial passage; e) expanding an rMVA virus strain identified by step d); and f) purifying the rMVA viruses from step e) to form the vaccine; wherein the expression and immunogenicity of said foreign protein antigens are stable after serial passage in the rMVA vaccine obtained from step e).

In some aspects of some embodiments, at least one of the foreign protein antigens is a cytomegalovirus (CMV) antigen. In further aspects, the CMV antigen is selected from the group consisting of pp65, CMV pp150, IE1, IE1 exon 4 (IE1/e4), IEfusion, glycoprotein B (gB) and antigenic fragments thereof.

In other aspects of some embodiments, the identification of rMVA virus carrying the MVA virus vector is accomplished by one or more gene-in selection methods, one or more gene-out selection methods, or a combination of gene-in and gene-out selection methods.

In other aspects of some embodiments, serial passage is at least 10 passages.

Another embodiment is directed to an rMVA virus strain comprising a nucleotide sequence encoding a modified H5 (mH5) promoter operably linked to one or more heterologous foreign protein antigens, wherein at least one of the foreign protein antigens is an IEfusion, said IEfusion comprising a nucleotide sequence encoding two or more antigenic portions of Immediate-Early Gene-1 or Immediate-Early Gene-2, wherein the antigenic portions elicit an immune response when expressed by a vaccine. In one aspect, the nucleotide sequence of IEfusion is SEQ ID NO:11.

BRIEF DESCRIPTION OF THE DRAWINGS

FIG. 2A, panel (i) was blotted with mAb 28-103 specific for pp65; FIG. 2A, panel (ii) was blotted with p63-27 specific for IE1 exon4 and FIG. 2A, panel (iii) was blotted with mAb specific for vaccinia viral protein.

FIG. 8A is the mH5-IEfusion-pZWIIA (GUS) plasmid DNA sequence (SEQ ID NO:9).

FIG. 8B is the mH5-pp65-GUS-pLW51(GUS) plasmid DNA sequence (SEQ ID NO:10).

FIG. 29 is a table representing qPCR data for establishing the IEfusion standard curve for and the copy number of sample 8B1A1A1A. based on said standard curve.

DETAILED DESCRIPTION OF THE INVENTION rMVA vaccines, rMVA viruses and their antigenic components, methods for producing the rMVA vaccines and methods of their use are provided. Such rMVA vaccines comprise immunologically effective amounts of rMVA viruses that express one or more foreign protein antigens under the control of a modified H5 (mH5) promoter, and methods for their production. In some embodiments, the foreign protein antigens are cytomegalovirus (CMV) antigens as described below. The vaccines described herein comprise an immunologically effective amount of said rMVA viruses that exhibit immunogenicity and are genetically stable after serial passage. These rMVA vaccines may be used, for example, as a vaccine to prevent, control or treat CMV infection.

Figure 5A:
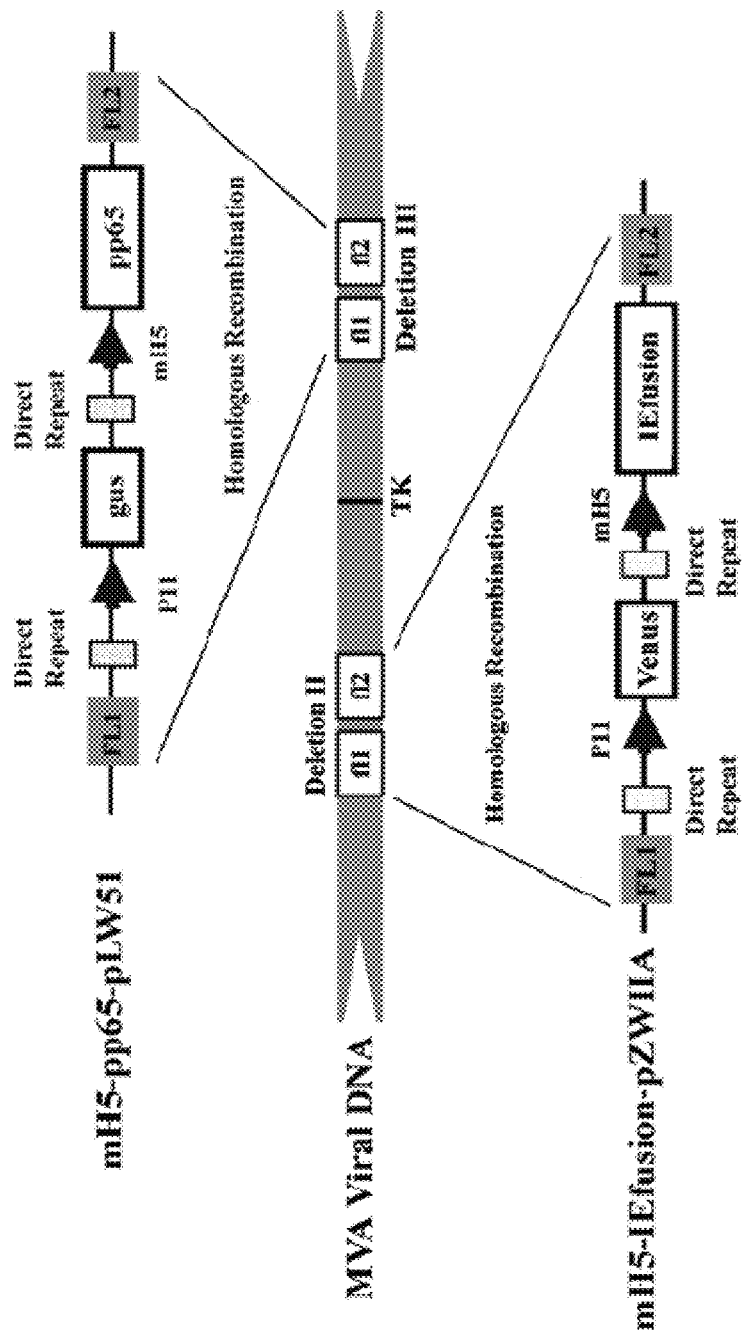
FIG. 5A is a schematic representation of the insertion sites for the transfer or shuttle plasmids to generate mH5-pp65-IEfusion-MVA.

In one embodiment, an rMVA vaccine comprising an immunologically effective amount of rMVA virus which is genetically stable after serial passage and can be produced by genetically engineering MVA viruses to express one or more foreign protein antigens under the control of a modified H5 (mH5) promoter. For example, an MVA transfer plasmid vector can be constructed first, which plasmid comprises a vaccinia mH5 promoter operably linked to a DNA sequence encoding one or more heterologous foreign protein antigens of interest, wherein the expression of the DNA sequence is under the control of the mH5 promoter. The plasmid may further contain DNA sequences coding for proteins used for screening or selection of rMVA viruses. The DNA coding sequence is in frame with the promoter, i.e., the vaccinia promoter and the DNA coding sequence (e.g., genes of interest and genes for screening or selection purposes) under the control of the promoter should have continuous open reading frames for expression of genes of interest. Next, rMVA viruses are generated by transfecting the plasmid vector obtained from the first step into wild type MVA virus for homologous recombination between the transfer plasmid(s) and the MVA backbone vector. See, e.g., FIG. 5A. An rMVA virus expressing the foreign protein antigen coding sequence can be selected by visible phenotype of the rMVA virus or by screening methods as further described below. The selected rMVA viruses are then purified or isolated to form the desired vaccine stock. The Examples below further illustrate more detailed procedures for the production of the genetically stable rMVA vaccine.

An "immunologically effective amount" as used herein means an amount that is both safe to a subject (animal or human) to be immunized and sufficient to improve the immunity of the subject. The immunologically effective amount can vary and can be determined by means of known art through routine trials.

In another embodiment, a cytomegalovirus (CMV) vaccine containing an immunologically effective amount of rMVA virus which is genetically stable after serial passage can be produced by the methods as described supra, in which the CMV gene is the gene of interest.

In one aspect of one embodiment, the foreign protein antigens may comprise one or more CMV antigens. Evidence from studies of murine CMV (MCMV) point to the important role of IE1 antigens for development of protective immunity in transplantation models (Reddehase et al. 1987). More recently, homologues of the human CMV pp65 antigen assembled into viral or plasmid DNA vectors showed evidence of stimulating protective immunity against murine CMV (MCMV), guinea pig CMV (GPCMV), or Rhesus CMV (RhCMV) (Morello et al. 2000; Schleiss et al. 2007; Yue et el. 2007). Further, an MVA may be developed into a vaccine for delivering CMV antigens and then clinically evaluated as to which of them exhibit protective qualities in the context of CMV complications resulting from transplant procedures (Song et al. 2007; Wang et al. 2004a; Wang et al. 2004b; Wang et al. 2007).

A CMV antigen can be a CMV protein antigen, a fragment of a CMV protein antigen, a modified CMV protein antigen, a fragment of a modified CMV protein antigen, a mutated CMV protein antigen or a fusion CMV protein antigen. Examples of CMV protein antigens and CMV fragments may include pp65, CMV pp150, IE1, IE1 exon 4 (IE1/e4), IE2 exon 5 (IE2/e5), glycoprotein B (gB) and antigenic fragments thereof. Examples of modified CMV protein antigens and fragments thereof may be found in U.S. Pat. No. 7,163,685 to Diamond et al. and is incorporated herein by reference in its entirety. Examples of mutated CMV protein antigens may be found in U.S. Pat. No. 6,835,383 to Zaia et al. and is incorporated herein by reference in its entirety.

Fusion CMV protein antigens may comprise two or more CMV proteins, modified CMV proteins, mutated CMV proteins or any antigenic fragments thereof. In some embodiments, a fusion CMV protein is an IEfusion protein, comprising a sequence that encoded two or more antigenic portions of Immediate-Early Gene-1 or Immediate-Early Gene-2. In one embodiment, an IEfusion protein is a fusion of IE1 exon 4 (IE1/e4) and IE2 exon 5 (IE2/e5), IE1/e4-IE2/e5 (IEfusion). Previous studies in CMV vaccine development point to robust immunity in mouse models using an MVA expressing pp65 and IE1 exon4 (Wang et al. 2007). The development of an IEfusion protein incorporating the adjacent exon5 increases the coverage of additional human leukocyte antigen (HLA) types by the vaccine, because of the different HLA recognition profiles for both IE1 and IE2 genes. Profound sequence differences between the major exons of both IE1 and IE2 genes result in a substantial difference in epitope motifs represented in both genes that is manifested by distinctly different immunologic profile of recognition among individuals who recognize either gene product. In one embodiment, the use of fusion proteins involves creating an IEfusion protein that comprises exon4 from IE1 and exon5 from the IE2 gene into a single gene without additional genetic material. The IEfusion protein comprises a more complete representation of the immediate-early antigens than either protein alone. Example 2 illustrates the construction of the IEfusion gene, its cloning into a transfer vector (pZWIIA), and generation of rMVA vector that expresses the IEfusion gene with or without co-expression of pp65.

In one embodiment, the nucleic acid sequence encoding pp65 has a sequence containing nucleotides 3235-4920 of SEQ ID NO: 9 (FIG. 8B). In another embodiment, the nucleic acid sequence encoding the IEfusion protein is SEQ ID NO:11.

To evaluate the IEfusion gene as an immunogen, extensive analysis was performed to establish parameters of expression and immunogenicity to qualify it for potential clinical use. Two forms of rMVA were designed to test the IEfusion protein, either as a single antigen or combined with pp65. Strong expression of the IEfusion protein as a single-antigen MVA or in combination with pp65 was shown. In either virus, the antigen was strongly expressed behind the synthetic E/L promoter (pSyn I). This demonstrates that the presence of pp65 did not interfere with IEfusion protein expression, contrary to earlier reports of interference (Gilbert et al. 1993; Gilbert et al. 1996). This result confirms the robust immunogenicity of an rMVA vaccine expressing IEfusion with or without co-expression of pp65 in mouse models as well as studies in human peripheral blood mononuclear cells (PBMC). These results are shown in Example 1 below. Immunogenicity analysis of this MVA vaccine is based on measuring CMV-specific IFN-γ+ T cell responses, which correlates with cytotoxic function in mouse models and protective immunity in clinical situations (Avetisyan et al. 2007; Sinclair et al. 2004). The immunogenicity of the recombinant MVA expressing pp65 and IEfusion antigens provides a strategic approach for developing a CMV vaccine for transplant recipients.

An rMVA that expresses IEfusion with or without co-expression of pp65 should expand the diversity of cellular immune responses against CMV to counter viremia in an immunosuppressed patient. The rationale of this vaccine virus is to include antigens from CMV that are expressed early to disrupt the viral life cycle. The representation of IE-specific immunity was maximized by including both the IE1 and IE2 antigens. pp65, IE1, followed by IE2, rank among the best recognized antigens in the CD8 subset, and with the largest proportion of the T cell memory response to CMV (Sylwester et al. 2005). There is no region of homology greater than 5 amino acids between the major exons of both proteins. Individually, both antigens are recognized broadly by almost 70% of the general population (Sylwester et al. 2005). While few epitopes have been mapped to unique sequence positions of either gene, the divergent sequence of both IE1/e4 and IE2/e5 used here predicts an entirely different subset of HLA binding peptides using publicly available Class I and II motif algorithms (Peters and Sette 2007). Human subjects that were evaluated for recognition of both IE1 and IE2 antigens were found in many instances to recognize one or the other but not both. Among the research subjects analyzed, 24% recognized IE2 with or without pp65 to the exclusion of IE1. This result strongly suggests that the recognition elements for both antigens are unique, and by including both of them in the vaccine, the breadth of individuals with disparate HLA types that will recognize and develop an immune response to the vaccine is extended. The fusion of major exons from both antigens achieves the dual goal of reducing the number of separate inserts and eliminating the need for a third insert promoter. The advantages of this approach include placement of all vaccine antigens in one vector, and diminishing the dose of virus needed to attain sufficient immunity simultaneously against all of the included antigens.

Humanized transgenic (Tg) mice that do not express murine Class I alleles (Lemonnier 2002) are available in a variety of forms that express human HLA A2, B7, A11, providing the most direct way to assess HLA recognition of vaccines in a mouse model (Firat et al. 2002). The processing of both rMVAs was first examined utilizing HHD II mice, which are known to be effective in processing and recognition of poxviruses specific for a wide variety of infectious pathogens, including CMV (Daftarian et al. 2005; Gomez et al. 2007; Wang et al. 2004b). The results confirm that the IEfusion antigen in MVA is processed and immunologically recognized throughout both exons, and the fusion joint does not impede this process. IFN-γ expression levels were used to assess T cell recognition of CMV antigens expressed from the vaccine, which is shown to have a strong correlation with cytotoxic function in mouse models (Daftarian et al. 2005; Song et al. 2007; Wang et al. 2004a). In addition, measurement of IFN-γ production has been relied upon to assess CMV immunity in CMV-infected healthy individuals (Ghanekar et al. 2001; Sinclair et al. 2004; Sylwester et al. 2005).

To further assess the capacity of the rMVA vaccine to be recognized in a variety of HLA context, B7 mice with a similar C57BL/6 background as the HHDII mice were also immunized with the pp65-IEfusion-MVA and investigated for immunogenicity using the same approach as with the HHDII mice. Highly effective recognition of the pp65 antigen was found as well as a CD8 response to the IE2 antigen using a peptide library. This illustrates that rMVA is processed efficiently by multiple HLA alleles, and provides further support for its utility as a clinical vaccine strategy. While HLA Class I Tg mice serve a fundamental and irreplaceable role to demonstrate the immunogenicity of the MVA constructs, they cannot be directly compared with human in vitro clinical results. The in vitro clinical results are best suited to be compared with human research subjects, because mice and human immune repertoires are not identical. As humans express a diversity of HLA alleles, a multi-antigen vaccine can encompass as many as possible to broaden the applicability of the vaccine to outbred human populations. While the Tg mice are a valuable tool to evaluate HLA Class I restricted CD8 T cell responses, they have an intact full complement of murine MHC Class II genes and cannot be directly compared to humans who possess a different repertoire of Class II MHC genes and DNA sequences. pp65 elicits the strongest CD4 response of the three antigens in both mice and humans. In contrast both IE1 and IE2 do not elicit strong CD4-based immunity in both mice and humans (compare FIGS. 11 and 13).

Prior to conducting experiments with rMVA in clinical samples, the capacity for stimulation of both CD4+ and CD8+ T cells was assessed using the commercially available pp65 and IE1 library and a newly designed IE2 peptide library. Relationships among the T cell populations were similar to prior results: pp65 promotes a substantial CD4 and CD8 response in over 70% of participants, while IE1 and IE2 are recognized less frequently and mainly in the CD8+ T cell compartment (Khan et al. 2002; Khan et al. 2007; Sylwester et al. 2005). This confirms that the IE2 formulation is a reagent of equal potency to the commercially available pp65 and IE1 peptide libraries to assess memory T cell responses in the volunteer pool, and should be an effective detection reagent of memory immune responses to rMVA. Recognition of all three libraries was evaluated in transplant recipients in all three risk groups including those with CMV-positive or -negative donors or themselves being CMV-negative with a CMV-positive donor. This study is unique because no previous evaluation of peptide libraries has been carried out with HCT recipients using all three antigens simultaneously (Lacey et al. 2006). Patient samples were examined at day 180 post-transplant to minimize the effects of myeloablation and incomplete immune reconstitution on the recognition of the peptide libraries. The immune recognition of all three libraries was successful in all patients, and the relative proportion of T cells that responded to each library also mirrored what was found in the healthy volunteers.

rMVA expressing the IEfusion antigen with or without the pp65 antigen was evaluated in PBMC from healthy volunteers to establish their recognition properties using a fully human system. The results showed that the memory T cell expansion stimulated by the rMVA for both the IEfusion and pp65 antigens, followed the proportions found ex vivo for the same volunteers using the peptide library approach. While there was substantial amplification of the relevant T cell populations, the stimulation did not skew the population towards a particular subset or antigen specificity. The data also confirms that the IEfusion protein is processed and presented appropriately to stimulate existing T cell populations in a manner that maintains the phenotypic distribution as expected in the ex vivo analysis. This outcome is most favorable towards using the rMVA as a vaccine in both CMV positives and negatives, since it is preferable to maintain the proportion of T cells that are associated with an asymptomatic phenotype and hopefully induce that same proportion in CMV-negative subjects. Stimulation of primary immunity in CMV-naïve mice was successful using in vivo immunization, but not from clinical samples in the CMV-naïve subject that was investigated. The conditions of in vitro immunization are insufficient in most cases to drive primary immunity, because the architecture of the lymph node, thymus and dendritic cell systems is missing, so the T cell precursors should pre-exist or form in culture. Developing primary immunity to CMV post-transplant is often delayed in the CMV-naïve recipient or donor in the case of stem cell transplant, and is thought to be a risk factor for CMV disease (Limaye et al. 2006; Ljungman et al. 2006). Precedent for poxvirus-based CMV vaccines to stimulate primary immunity was established with a single-antigen pp65-ALVAC used in a clinical trial conducted with CMV-negative healthy volunteers (Berencsi et al. 2001).

The rMVA vaccine described herein overcomes the unreliability of in vitro immunization for eliciting primary immunity. It also provides an alternative approach to adoptive transfer, which is not feasible when considering a CMV-negative donor for HCT or a CMV-negative recipient of a CMV infected donor organ (Walter et al. 1995). It is problematic for CMV itself to serve as a stimulator for characterizing memory responses. The concurrent activating and immunosuppressive properties of CMV can confound interpretation of immunologic methods using it for in vitro stimulation (Manley et al. 2004). In fact, one needs to artificially remove the immune-evasion genes from CMV in order to elicit a diverse immune response that includes the IE antigens, a fact that has been stressed in the literature (Khan et al. 2005; Manley et al. 2004). Laboratory strains of CMV that are the only practical approach for growing the virus to assess recall immunity are plagued with an artificial excessive accumulation of the pp65 protein that interferes with the recognition of IE proteins which also has been discussed in the literature and has been the source of controversy in the field (Gilbert et al. 1996; Kern et al. 1999; Wills et al. 1996).

In contrast, it has been shown that MVA vaccines composed of CMV subunit antigens (e.g. pp65, IE1, and gB) can elicit primary immunity in CMV-naïve rhesus macaques, even offering partial protection against a challenge dose of rhesus CMV (Yue et al. 2008). The profile of immune responses that are stimulated by MVA are different than what could be elicited using CMV as a viral stimulator in culture methods. Consequently, since rMVA or ALVAC expressing CMV antigens expand T cell populations in both CMV-naïve (mice and macaques) and experienced (human) hosts, one application of a CMV vaccine described herein is in the high-risk CMV-negative transplant recipient for protection against the effects of a CMV-infected organ. One example would introduce the pp65-IEfusion-MVA as a vaccine into the CMV-negative recipient as a precaution several months before transplant (Khanna and Diamond 2006; La Rosa et al. 2007). Another application is to use pp65-IEfusion-MVA as a vehicle to expand T cell populations from CMV-positive donors of HCT, and infuse the amplified T cells into a transplant recipient with active viremia.

The most rigorous evaluation of the processing of the rMVA for T cell response is using PBMC from transplant patients. PBMC from HCT recipients in all three risk categories were evaluated and an equivalently strong recognition of both rMVAs was found. In some cases, it was even more vigorous than in the PBMC of healthy adults. No interference with the recognition of the IE antigen by the co-expressed pp65 antigen was found from the same rMVA, which further confirms that the recognition of both antigens can take place at the same time and derived from the same vector. Prime-boost strategies utilizing heterologous vaccines, including DNA and viral vectors, suggest improved immunogenicity in several pathogen models, including malaria and HIV (Barouch et al. 2003; Gilbert et al. 2006; Goonetilleke et al. 2006; Peters et al. 2007). The ongoing evaluation of a DNA vaccine against CMV suggests a worthwhile strategy of combining MVA with a plasmid DNA vaccine. The excellent track record of MVA used as a vaccine in the immunosuppressed population makes it an ideal candidate as a therapeutic in HCT recipients (Cosma et al. 2003; Mayr and Danner 1978; Stittelaar et al. 2001).

The term "genetic stability" as used herein refers to a measure of the resistance to change, with time or serial passage of virus, of the DNA sequence of a gene, the expression level of the gene, or both. The genetic stability of the target gene in an rMVA vector is a concern in the development of a vaccine. A reduction of the genetic stability of the target gene may have the effect of reducing the immunogenicity of the rMVA vector due to changes in gene sequence or expression level.

Genetic stability of recombinant virus can be measured or assessed by numerous methods known in the art, e.g., testing foreign protein expression levels at each passage by Western blot (WB) or immunostaining virus plaques and calculating the percentage of foreign protein producing foci before and after serial passage (de Haan et al 2005; Timm et al. 2006; Wyatt et al. 2008a; Wyatt et al. 2008b). These methods are time-consuming and labor intensive. An alternative method to assess genetic stability is by quantitative PCR (qPCR), which amplifies isolated MVA genomic DNA and calculates the copy numbers of the inserted gene of interest and MVA vector after each passage. The ratio of the gene of interest copy number versus the MVA backbone vector copy number is used to determine the genetic stability of the gene or the MVA vaccine carrying the gene. A higher ratio of the gene of interest copy number to the MVA backbone vector copy number reflects a higher genetic stability, with the highest ratio=1 means approximately 100% gene expression remains after serial passage. qPCR is more sensitive, high-throughout and provides highly reproducible results relative to other methods, such as Western blot or immunostaining. The method of qPCR can be performed following well known procedures in the art or the manuals of commercially available qPCR kit, which is also illustrated in Example 2 below. The TaqMan PCR method can also be adapted for stability testing as previously described (Butrapet et al. 2006)

An rMVA vaccine carrying a gene of interest is genetically stable when the DNA sequence of the gene and the expression of the gene is substantially unchanged over the time or serial passage of the vaccine, particularly, after 5 or more passages, more particularly, after 10 or more passages.

Figure 1A:
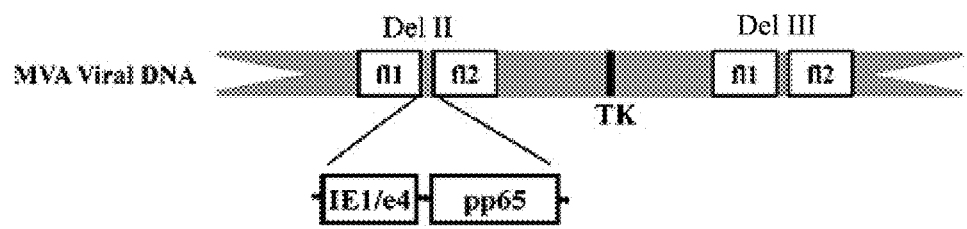
FIG. 1A is a schematic map of the pp65 and IE1/e4 gene expression cassette of pSyn-pp65-IE1/e4-MVA generated by homologous recombination.

As illustrated in the examples below, with a homogenous initial virus stock of MVA expressing pp65-IE1 or pp65-IEfusion under strong promoter pSyn, 100% (6 of 6 isolates) of individual isolates from passage 1 (P1) had pp65 expression. However, pp65 protein expression levels decreased significantly during serial passage. About 40% (8 of 18 isolates) of individual isolates of pSyn-pp65-IE1-MVA had lost pp65 protein expression in passage 10. Southern blot assays for pp65 and IE1 gene insertion demonstrated that non-expressing mutant isolates lost the entire gene expression cassette at the deletion II region of pSyn-pp65-IE1/e4-MVA (FIG. 1C).

As illustrated in Example 2 below, the deletion II region of the MVA has been studied using restriction endonuclease analysis of MVA genomic DNA and qPCR using a series of primers (SEQ ID NOs: 1-8) that targeted the surrounding deletion II (del II) region. The pp65 and IE1 gene expression cassettes including pSyn promoters together with the surrounding MVA del II region were absent after passages. As shown in Example 2, pSyn-pp65-IEfusion-MVA was serially passaged five times. However, instability was observed after a single passage. pSyn-pp65-IEfusion-MVA was highly unstable, as only 10% of the CMV-pp65 and IEfusion gene copies remained after 5 passages. This means that 90% of the original levels of pp65 and IEfusion insert sequences were lost as detected by qPCR. See FIG. 4B. pSyn-pp65-IE1/e4-MVA was slightly more stable, and had a 70% loss of insert gene copies after serial passage. These data are consistent with stability of rMVA being negatively affected by the type of insertion because the only difference between pSyn-pp65-IE1-MVA and pSyn-pp65-IE1/e4-MVA is the addition of IE2 exon5 gene and its fusion to IE1 exon4.

The molecular mechanism for genetic instability of rMVA using pSyn promoter and improved genetic stability using mH5 promoter has yet to be fully investigated. The cause for the instability of rMVA may be due to high protein expression levels, which may be toxic to the cells which are infected by the rMVA, since the pSyn promoter is optimized to attain high levels of transcriptional activity (Chakrabarti et al. 1997; Wyatt et al. 2009; Wang et al. 2010). Instability problems have also been observed with respect to HIV-Env and the measles virus F protein expressed in MVA (Gomez et al. 2007; Stittelaar et al. 2000). In both cases, toxicity of the expressed protein contributed to genetic instability of the rMVA expressing them (Wyatt et al. 2009). Further, it has been reported that rMVA expressing hemagglutinin-neuraminidase (HN) glycoproteins under control of the vaccinia pSyn promoter replicate poorly due to toxic levels of the gene product (Wyatt et al. 1996). The rMVA expressing PIV3 F and HN genes under control of pSyn replicates poorly whereas rMVA expressing both genes under control of mH5 promoter can replicate to high titer in CEF cells due to less expression of PIV3 and HN (Wyatt et al. 1996). Genetic stability of rMVA was enhanced by reducing expression levels of HN glycoproteins.

As illustrated by the Examples below, stable expression of foreign protein antigens, and thereby immunogenicity, of rMVA vaccines after serial passage can be rendered by expressing the foreign protein antigens under control of a mH5 promoter. For example, in MVA vectors expressing pp65, pp65-IE1/e4, pp65-IE2/e5, or pp65-IEfusion, mH5 promoter, which is a weaker promoter than pSyn, directs more stable expression after serial passage, thereby translates to more potent immunogenicity, relative to expression and immunogenicity exhibited by MVA vectors expressing the same proteins under pSyn.

Thus, an rMVA virus that expresses one or more foreign protein antigens under the control of modified H5 (mH5) promoter exhibits both genetic stability and immunogenicity after serial passage (Wang et al. 2010). In one embodiment, the nucleic acid sequence encoding vaccinia mH5 promoter has a sequence containing nucleotides 3075-3168 of SEQ ID NO: 9 or 3022-3133 of SEQ ID NO: 10 (FIGS. 8A and 8B).

The construction of the rMVA vector can be made by well-known techniques. See, e.g., Maniatis et al. *Molecular Cloning: A Laboratory Manual*, Cold Spring Harbor Laboratory Press (1982). For example, an MVA transfer plasmid containing IE, IEfusion and pp65 under pSyn or mH5 promoters can be constructed. See Examples 1 and 2. The expressing cassettes can be constructed with one promoter directing the expression of one or more genes of interest or in the form that each gene of interest is under control of a separate promoter. The plasmids are transfected into wild type MVA virus stock to produce rMVA viruses. Serial passages of rMVA viruses are conducted and expression levels of the CMV antigens are measured by Western blot or qPCR. Primers for qPCR can be designed with knowledge of gene information of the desired or interested foreign protein antigen and genomic information of MVA, e.g., CMV antigen coding gene MVA DNA sequence information illustrated in FIGS. 8A and 8B. The genetic stability and immunogenicity can be assessed after each passage and the final passage, as illustrated by Example 2 below (qPCR).

In one embodiment, an rMVA vector that expresses IEfusion and pp65 may be constructed from two MVA transfer plasmids, mH5-IEfusion-pZWIIA (GUS) (FIGS. 7A and 8A; SEQ ID NO:9) and mH5-pp65-pLW51 (GUS) (FIGS. 7B and 8B; SEQ ID NO:10).

The mH5-IEfusion-pZWIIA (GUS) plasmid (9.388 kbp) (FIG. 7A) has the following major sequence features that are integrated into MVA: (i) an MVA deletion II flanking region 1 (FL1) (SEQ ID NO:9; nucleotides 1-575), (ii) a restriction enzyme site and linker sequence (SEQ ID NO:9; nucleotides 576-599), (iii) an MVA direct repeat (DR) (SEQ ID NO:9; nucleotides 600-884), (iv) a P7.5 vaccinia promoter sequence (SEQ ID NO:9; nucleotides 885-919), (v) a bacterial gus marker gene (GUS) (SEQ ID NO:9; nucleotides 920-2739), (vi) an MVA direct repeat (DR) (SEQ ID NO:9; nucleotides 2740-3021), (vii) a vaccinia mH5 promoter and restriction site sequence (SEQ ID NO:9; nucleotides 3022-3133), (viii) an HCMV IEfusion gene (SEQ ID NO:9; nucleotides 3134-5842), (ix) a restriction site sequence (SEQ ID NO:9; nucleotides 5843-5931), (x) a non-bacterial origin pGEM-4Z vector backbone (SEQ ID NO:9; nucleotides 5932-6009), and (xi) an MVA deletion II flanking region 2 (FL2) (SEQ ID NO:9; nucleotides 6010-6399). In addition, the transfer plasmid includes the bacterial plasmid backbone (SEQ ID NO:9; nucleotides 6400-7896 and nucleotides 8758-9388) which corresponds to pGEM-4Z (accession no. X65305) and the bacterial ampicilin resistance gene (SEQ ID NO:9; nucleotides 7897-8757). See FIG. 8A.

The mH5-pp65-pLW51 (GUS) plasmid (8.152 kbp) (FIG. 7B) has the following major sequence features that are integrated into MVA: (i) an MVA deletion II flanking region 1 (FL1) (SEQ ID NO:10; nucleotides 1-652), (ii) an MVA direct repeat (DR) (SEQ ID NO:10; nucleotides 653-933), (iii) a P11 vaccinia promoter sequence (SEQ ID NO:10; nucleotides 934-975), (iv) a bacterial gus marker gene (GUS) (SEQ ID NO:10; nucleotides 976-2794), (v) an MVA direct repeat (DR) (SEQ ID NO:10; nucleotides 2795-3074), (vi) a vaccinia mH5 promoter and restriction site sequence (SEQ ID NO:10; nucleotides 3075-3168), (vii) a multiple restriction site sequence (SEQ ID NO:10; nucleotides 3169-3234) (PmeI/SalI/ClaI/HindIII/EcoRI/EcoRV/PstI), (viii) an HCMV pp65 gene (SEQ ID NO:10; nucleotides 3235-4920), (ix) a restriction site sequence (SEQ ID NO:10; 4921-4941) (AscI/PstI), and (x) a MVA deletion II flanking region 2 (FL2) (SEQ ID NO:10; nucleotides 4942-5330). In addition, the transfer plasmid includes the bacterial plasmid backbone (SEQ ID NO:10; nucleotides 5331-6672 and nucleotides 7534-8152) which corresponds to pGEM-4Z (accession no. X65305) and the bacterial ampicilin resistance gene (SEQ ID NO:10; nucleotides 6673-7533). See FIG. 8B.

The process of rMVA vector construction may include various selection methods in order to select only those vectors that contain desired characteristics. For example, one embodiment is directed to the construction of an rMVA containing IEfusion wherein an IEfusion plasmid is transfected into wild type MVA virus stock. The resulting population comprises unsuccessfully transfected MVA and successfully transfected rMVA that contains IEfusion. An antibody-based screening approach is then used to screen out the unsuccessfully transfected MVA. Another embodiment is directed to the construction of an rMVA containing pp65 wherein a pp65 plasmid is transfected into wild type MVA virus stock. The resulting population comprises unsuccessfully transfected MVA and successfully transfected rMVA that contains pp65. An antibody-based screening approach is then used to screen out the unsuccessfully transfected MVA.

A further embodiment is directed to the construction of an rMVA containing IEfusion and pp65 wherein a pp65 plasmid is transfected into rMVA that contains IEfusion. The resulting population comprises unsuccessfully transfected rMVA that contains IEfusion and successfully transfected rMVA that contains IEfusion and pp65. An antibody-based screening approach is then used to screen out the unsuccessfully transfected rMVA. Construction of an rMVA containing IEfusion and pp65 may also be attained wherein an IEfusion plasmid is transfected into rMVA that contains pp65. The resulting population comprises unsuccessfully transfected rMVA that contains pp65 and successfully transfected rMVA that contains pp65 and IEfusion. An antibody-based screening approach is then used to screen out the unsuccessfully transfected rMVA.

According to the invention, an rMVA virus can be selected by visible phenotype, if any. Many recombinant screening methods known in the art or their combinations can also be used for identifying rMVA virus carrying the rMVA virus vector. For example, by targeting the foreign gene to the thymidine kinase (TK) locus, recombinant viruses can be selected by their TK-negative phenotype in TK-deficient cells. Alternatively, the transfer vector may enable the co-integration of an antibiotic selection marker or a reporter gene allowing color screening due to β-galactosidase or β-glucuronidase synthesis. The reversal of host range restriction or plaque phenotype can also be used. See, e.g., Moss B, Genetically engineered poxviruses for recombinant gene expression, vaccination, and safety, *Proc. Natl. Acad. Sci. USA* 93(21):11341-48 (1996).

The screening methods contemplated by the invention include, but are not limited to, gene-in (positive selection) and gene-out (negative selection) methods. rMVA vector construction may include one or more screening methods that may include all gene-in methods, all gene-out methods, or any combination thereof.

A gene-in screening method is used to screen rMVA virus to determine whether a gene of interest is incorporated (by homologous recombination) into the MVA backbone and expressed by the rMVA virus. Examples of the gene-in method include, but are not limited to, antibiotic resistance selection, colorimetric screening, light or fluorescence screening, nucleic acid testing and immunoscreening.

In one gene-in method, antibiotic resistance selection, the MVA vector contains an antibiotic resistance gene such that when MVA viruses replicate, only those which incorporate the rMVA vector survive in the medium with the corresponding antibiotic. Any antibiotic, mixtures and the combinations thereof may be used, such as ampicillin, kanamycin, tetracycline, and chloramphenicol and their corresponding resistance gene.

Another gene-in method, colorimetric screening, is a method in which the detection of a target is indicated by a visible detectable color change, e.g., the detection of the product of a reporter gene genetically on rMVA vector virus binding to a substrate molecule. The strength of the binding can also be detected by the method and indicated by a color change. For example, the rMVA vector can be constructed to include a reporter gene such as a lacZ gene or gus gene. The lacZ encodes β-galactosidase (lacZ). rMVA virus expressing lacZ produce β-galactosidase which are turned blue by X-gal (5-bromo-4-chloro-3-indolyl-β-D-galactoside). See Joung et al. A bacterial two-hybrid selection system for studying protein-DNA and protein-protein interactions, *Proc Natl Acad Sci USA*, 97(13): 7382-87 (2000). Another reporter gene, gus, encodes beta-glucuronidase, which is an enzyme that can transform the host into colored or fluorescent products when incubated with some specific colorless or non-fluorescent substrates. See Jefferson et al., beta-Glucuronidase from *Escherichia coli* as a gene-fusion marker, *Proc Natl Acad Sci* 83(22): 8447-51 (1986). Thus, in an rMVA virus carrying a cassette expressing both a gene of interest and a reporter gene for colorimetric screening, the co-expression of the reporter gene, such as lacZ or gus gene, together with the gene encoding the foreign protein antigen is indicated by a color change due to the binding of the reporter gene products, such as β-galactosidase and beta-glucuronidase, with a substrate molecule.

In another gene-in method, fluorescence screening, the MVA vector includes a luminescence or fluorescence gene such that the co-expression of the luminescence or fluorescence gene together with the gene encoding the foreign protein antigen is indicated by illumination of light or fluorescence, which is visible by eye or can be detected by an instrument, such as a fluorescence microscope. One example of luminescent molecule is luciferase. Light is emitted when luciferase acts on the appropriate luciferin substrate. Examples of fluorescent molecule include, but are not limited to green fluorescent protein (GFP), blue fluorescent protein (BFP), red fluorescent protein (RFP), cyan fluorescent protein (CFP) and yellow fluorescent protein (YFP, such as the Venus™ fluorescent marker, a commercially available YFP variant, used the Examples below). For example, fluorescence gene constructed in the same open reading frame as the gene coding for the foreign gene in an rMVA vector, the expression of the genes causes the transformed MVA virus (rMVA virus) plaques to fluoresce. Further details of how to choose a fluorescent protein can be determined by means of known art through routine trials. See Shaner et al., A guide to choosing fluorescent proteins, *Nat Methods* 2(12): 905-9 (2005).

Nucleic acid testing is another gene-in method used to detect or sequence the nucleic acid molecule of the rMVA vector for a desired sequence. PCR may be used to detect the desired sequence, e.g., a sequence unique in rMVA vector but not in wild type MVA genome. As illustrated in Example 2, qPCR methods can be used to assess copy numbers of MVA vector and genes of interest after each passage. Primers for qPCR can be designed with knowledge of gene information of the desired or interested foreign protein antigen (e.g., cytomegalovirus (CMV) antigen coding DNA sequence information illustrated in FIGS. 8A and 8B) and genomic information of MVA. Other nucleic acid testing methods include sequencing the MVA vector DNA to determine whether the cassette expressing the gene of interest is incorporated into the MVA vector backbone sequence via homologous recombination.

Immunoscreening is another gene-in method for detecting the expression of a gene of interest in an rMVA vector via immunologic reaction. For example, the expression of interested or desired foreign protein antigen, e.g., a cytomegalovirus (CMV) antigen, can be detected by an antibody to the desired foreign protein antigen. See Akoolo et al., Evaluation of the recognition of *Theileria parva* vaccine candidate antigens by cytotoxic T lymphocytes from Zebu cattle, *Vet Immunol Immunopathol* 121(3-4):216-21 (2008).

Gene-in screening methods are useful in many situations. However, when a recombinant gene or protein is used in the development of gene therapy and vaccination methods, gene-out screening methods may be desired or necessary to ensure that a particular gene is not expressed in vivo. A gene-out screening method is used to screen rMVA virus to determine whether a gene of interest is not incorporated, excised or deleted in the rMVA virus. Such methods may include the use of inserted genes to provide a "suicide" or "fail-safe" trait that would permit the destruction of gene-modified cells if they would result in harm to the host. Other methods may include the removal of a gene used in a gene-in screening method. For example, an rMVA virus may contain a gus-selection marker gene used for isolation of successfully transfected rMVA based on blue color selection in the presence of β-glucoronidase substrate (gene-in). To ensure the isolated rMVA virus that is to be used as a vaccine does not contain an unnecessary and potentially allergenic bacterial protein, the gus-selection marker gene is flanked by two direct repeat sequences to facilitate gus gene removal by intragenomic recombination (gene-out). See FIG. 9. Other examples of gene-out methods include, but are not limited to toxic prodrug, flanking inverted repeats and cre-lox system.

A further embodiment is a method for producing a genetically stable rMVA vaccine by genetically engineering MVA viruses to express foreign protein antigens under the control of a mH5 promoter. As described supra, first, an MVA transfer plasmid vector can be constructed, which plasmid comprises a vaccinia mH5 promoter operably linked to a DNA sequence of interest encoding one or more heterologous foreign protein antigens, wherein the expression of the DNA sequence is under the control of the mH5 promoter. The plasmid may further contain DNA sequences coding for proteins used for screening or selection of rMVA viruses. The DNA coding sequence is in frame with the promoter, i.e., the vaccinia promoter and the DNA coding sequence (e.g., genes of interest and genes for screening or selection purposes) under the control of the promoter have continuous open reading frames for expression of genes of interest. Next, rMVA viruses are generated by transfecting the plasmid vector obtained from the first step into wild type MVA virus for homologous recombination between the transfer plasmid(s) and the MVA backbone vector. See, e.g., FIG. 5A. An rMVA virus expressing the foreign protein antigen coding sequence can be selected by visible phenotype of the rMVA virus or by screening methods as further described below. The selected rMVA viruses are then purified or isolated to form the desired vaccine stock. The Examples below further illustrate more detailed procedures for the production of the genetically stable rMVA vaccine. The rMVA vaccine obtained from the method exhibits genetic stability and maintains immunogenicity after serial passage, for example, after at least 5 or after at least 10 passages.

A further embodiment is a method for producing a genetically stable vaccine as described supra, wherein the foreign protein antigen is a CMV antigen.

Genetic stability of expression and immunogenicity after each passage and the final passage can be assessed as illustrated by Example 2.

Another embodiment is a method for the prevention or treatment of infections or cancer in a mammal subject by administering to the subject a genetically stable rMVA vaccine, wherein the rMVA vaccine contains a foreign protein antigen under control of a mH5 promoter. Another embodiment is a method for the prevention or treatment of infections or cancer in a mammal subject by administering to the subject a genetically stable CMV rMVA vaccine, wherein the rMVA vaccine contains one or more CMV antigens under control of a mH5 promoter. The subject is a human or animal subject, for example, a mammal subject or a human subject.

Having described the invention with reference to the embodiments and illustrative examples, those in the art may appreciate modifications to the invention as described and illustrated that do not depart from the spirit and scope of the invention as disclosed in the specification. The examples are set forth to aid in understanding the invention but are not intended to, and should not be construed to, limit its scope in any way. The examples do not include detailed descriptions of conventional methods. Such methods are well known to those of ordinary skill in the art and are described in numerous publications. All references mentioned above and below in the specification are incorporated by reference in their entirety, as if fully set forth herein.

EXAMPLE 1

CMV Antigens Stimulate Immunity in an rMVA Vaccine Vector

Materials and Methods.

Human patient specimens. The study protocols were approved by the institutional review board at City of Hope Medical Center (COH), and specimens and data were obtained prospectively after informed consent was obtained from subjects. PBMC from healthy donors and 9 HCT recipients at 180 days post-transplant were collected at COH and cryopreserved by standard methods (Maecker et al. 2005). HLA typing was performed at the COH HLA Laboratory by standard SSOP methods. Haplotypes for both Class I and II alleles were determined (data not shown). No intentional bias occurred in selection of HLA types to be included in this study, as all patients or volunteers were randomly chosen. The CMV serostatus of these subjects was determined as previously described by using latex agglutination (CMV-SCAN; Becton Dickinson) (La Rosa et al. 2007).

Mouse strains and conditions of immunization. HHD II (Pascolo et al. 1997) and HLA B*0702 (Rohrlich et al. 2003) Tg mice were bred and maintained under pathogen-free conditions in the AALAC-approved animal care facility at COH. Eight to ten-week old groups of Tg mice (Avetisyan et al. 2007; Barouch et al. 2003) were immunized i.p. with different rMVA constructs (as described in the figure legends).

Synthetic peptides and monoclonal antibodies. HLA-A*0201 pp65$_{495-503}$ (Diamond et al. 1997), HLA B*0702 pp65$_{265-275}$ (Longmate et al. 2001) and HLA-A*02 IE1316-324 (Khan et al. 2005) restricted CMV peptides were used as previously described (La Rosa et al. 2001). Overlapping 15-AA peptides (PepMix™) spanning full length CMV pp65 and IE1 proteins were purchased from JPT Peptide Technologies GmbH (Berlin, Germany). Splenic murine cell suspensions were evaluated in flow cytometry using the following antibodies: CD8-FITC (Clone Ly-2), CD4-PE (Clone L3T4), and IFN-γ-APC (Clone XMG1.2). Antibodies used for flow cytometry of clinical specimens include antihuman CD8-PE (Clone RPA-T8), CD4-FITC (Clone RPA-T4) and IFN-γ-APC (Clone B27), purchased from BD-Pharmingen.

Construction of synthetic IE2 peptide library. The 580 amino acid primary sequence of the IE2 protein [Swiss Prot #P19893] was divided into 15mer stretches that overlap successive peptides by 11 amino acids using an online program which excludes impermissible amino acids at the amino (Q) and carboxyl (GPEDQNTSC; SEQ ID NO:17) terminus of each 15mer peptide based on synthetic considerations. 133 peptides were predicted using the algorithm with an average length of 15 AA, but tolerating up to 5-AA length variance to eliminate forbidden terminal amino acids. A total of 123 peptides were synthesized with a Symphony™ peptide synthesizer (Protein Technologies, Inc., Tucson, Ariz.) using standard 9-fluorenylmethoxy carbonyl protocols and purified by high performance liquid chromatography (Agilent Technologies 1200 series) (Daftarian et al. 2005). The mass of each peptide was confirmed by matrix assisted laser description ionization time of flight analysis using a Kompact Probe™ mass spectrometer (Shimadzu Corp., Chestnut Ridge, N.Y.). The library was sub-divided into ~20 peptides/pool, and subsequently combined into one super-pool containing all the component peptides. Several peptides were impractical to synthesize, and they did not enter into the pool including a 32-AA stretch between 251 and 282 of IE2 sequence. All peptides were individually solubilized in 30% acetonitrile/water, except 6 with pKs N8, which were dissolved in 0.1% ammonium bicarbonate in 30% acetonitrile/water. The solubilized peptides, sub-divided into six pools, were further combined into a single super-pool, with each peptide at a concentration of 200 μg/ml, dissolved in 50% DMSO/water, and kept at −80° C. in single use aliquots. The single use aliquots were diluted into cell culture medium at a final concentration of 1 μg/ml/peptide for all cellular immunology assays based on previous titration studies.

Construction of recombination pZWIIA plasmids for derivation of rMVA. The MVA transfer plasmid named pZWIIA with dual vaccinia synthetic promoters (pSyn I and II) was constructed to facilitate the derivation of bacterial marker gene-free rMVA (Wang et al. 2007). To construct the IEfusion gene, the following primers were designed with synthetic restriction enzyme sites shown as underlined:

```
Primer a:
                                         (SEQ ID NO: 12)
5'AGCTTTGTTTAAACGCCACCACCATGGTCAAACAGATTAAGGTTCG

3';

Primer b:
                                         (SEQ ID NO: 13)
5'GGCATGATTGACAGCCTGGGCGAGGATGTCACCCTGGTCAGCC

TTGCTTCTAGTCACCAT3';

Primer c:
                                         (SEQ ID NO: 14)
5'TGTTAGCGTGGGCCCGGTGCTACTGGAATCGATACCGGCATGA

TTGACAGCCTGGGCGAGGATGTCACC3';

Primer d:
                                         (SEQ ID NO: 15)
5'TAGCACCGGGCCCACGCTAACAACCCAC3';
and Primer e:
                                         (SEQ ID NO: 16)
5'TTGGCGCGCCTTTATTTTACTGAGACTTGTTCCTCAGGT3'.
```

Figure 9A:
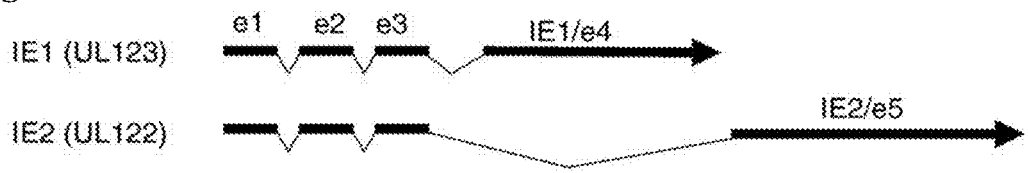
FIG. 9A illustrates the genomic structure of the regulatory immediate-early genes IE1 and IE2 of HCMV. IE1 is composed of 4 exons (exon1, 2, 3 and 4) indicated by solid dark lines and three introns as indicated by intervening thin lines; IE2 is also composed of 4 exons (exon1, 2, 3 and 5) as indicated by solid dark lines and three introns as indicated by intervening thin lines.
Figure 9B:
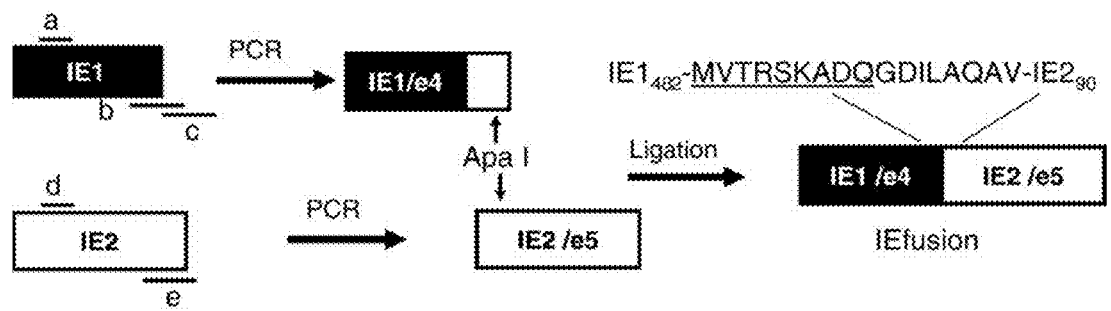
FIG. 9B illustrates construction of the IEfusion gene. Primers a, b, c, d, e are described in Example 1. IE1/e4 was amplified from the IE1 gene using primers a and b, and was further extended using primer a and c to introduce an internal Apa I site, and external Pme I and Asc I sites. IE2/e5 was amplified from the IE2 gene using primers d and e. It was digested at the newly created Apa I and synthetic Asc I site. IE1/e4 and IE2/e5 were joined together by ligation preserving the reading frame (shown as SEQ ID NO: 18).
Figure 9C:
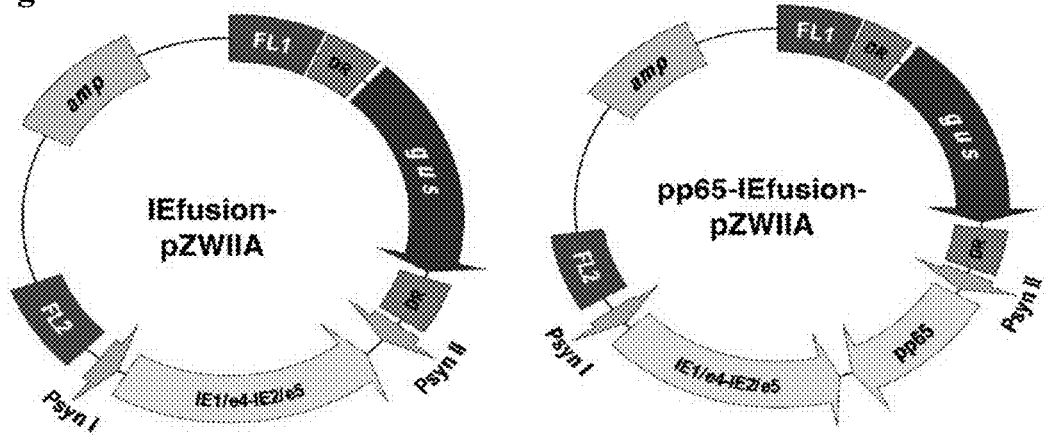
FIG. 9C is a schematic map of IEfusion-pZWIIA and pp65-IEfusion-pZWIIA MVA transfer plasmids. pZWIIA, an ampicillin resistant plasmid (amp shown in light grey) inserts DNA sequence within the boundaries of MVA deletion II via flanking regions 1 and 2 (FL1, FL2). pZWIIA has two vaccinia synthetic E/L promoters of slightly different sequence, arranged head to head to each drive expression of separate genes. IEfusion gene is driven by pSyn I promoter (Chakrabarti et al. 1997) and pp65 gene is driven by pSyn II promoter (Wyatt et al. 2004) The gus bacterial marker gene, used for identifying recombinant MVA, is flanked by two direct repeat (DR) sequences to facilitate gus gene removal by intragenomic recombination from IEfusion-MVA or pp65-IEfusion-MVA. pp65 was not fused to the IEfusion gene in either transfer plasmid.

Primers a and b were used to amplify IE1/e4, and after gel purification, the IE1/e4 PCR product was amplified again using Primers a and c and digested with Pme I and Apa I. Primer b overlaps the junction between IE/e4 and IE2/e5 without adding any non-CMV genomic sequence. Primers c (G to C) and d (C to G) contain a single nucleotide change that creates an Apa I site, but does not alter the amino acid sequence. The resulting fragment was cloned into pNEB193 to yield IE1/e4-pNEB193. IE2/e5 was amplified using Primers d and e and PCR products were digested with Apa I and Asc I and cloned into IE1/e4-pNEB193 to yield IE1-IE2-pNEB193. IE1-IE2 fusion gene (IEfusion) was excised from IE1-IE2-pNEB193 with Pme I and Asc I restriction enzymes and cloned into pZWIIA behind vaccinia pSyn I promoter (Chakrabarti et al. 1997) to yield IEfusion-pZWIIA (FIG. 9C). To construct pp65-IEfusion-pZWIIA, the 1.7 kb CMV pp65 gene was PCR amplified from an existing plasmid and cloned into Nhe I and Asc I sites of pZWIIA behind vaccinia pSyn II promoter (Wyatt et al. 2004) to yield pp65-IEfusion-pZWIIA (FIG. 9C). In neither MVA was pp65 fused to the IEfusion gene. MVA transfer plasmids were verified by restriction enzyme digestion and DNA sequencing.

Generation of IEfusion-MVA and pp65-IEfusion-MVA. pp65-IEfusion-MVA was generated in CEF cells via homologous recombination by a transfection/infection method as described previously (Wang et al. 2004a; Wang et al. 2007). pp65-IEfusion-MVA was isolated based on blue color selection by nine consecutive rounds of plaque purification on CEF cells in the presence of β-glucoronidase substrate (X-glcA). IEfusion-MVA was generated similarly to pp65-IEfusion-MVA. The gus selection marker gene in rMVA virus was screened out using a limiting dilution method as described previously (Wang et al. 2008). Wt MVA-free and color marker gene-free recombinant IEfusion-MVA and pp65-IEfusion-MVA virus were expanded and purified by 36% sucrose density ultracentrifugation, resuspended in PBS containing 7.5% lactose, retested for protein expression by Western blot (WB), aliquoted, and frozen at −80° C.

Western blot detection of protein expression. The pp65 and IEfusion protein expression levels, measured as separate proteins with distinct molecular weights from IEfusion-MVA and pp65-IEfusion-MVA-infected cells was determined by WB using an enhanced chemiluminescence-based ECL Plus™ detection kit (Amersham Pharmacia Biotech, Buckinghamshire, United Kingdom). Cell lysates were separated by SDS-PAGE on 10% gels. After electro-transfer of proteins from the gel onto PVDF membranes (Bio-Rad, Hercules, Calif.), the membranes were incubated first with purified mAb 28-103 (Britt et al. 1985) to detect pp65 as a separate protein, or mAb p63-27 (Plachter et al. 1993) to detect the IE1 or IEfusion protein, followed with HRP-labeled goat anti-mouse Ab according to the manufacturer's instructions.

Ex vivo and in vitro stimulation conditions for human PBMC. Cryopreserved PBMC were rapidly thawed and immediately cultured in 15-ml Falcon tubes at a density of 1 million/ml in RPMI 1640 medium (Invitrogen) supplemented with 10% FCS (Omega Scientific Inc, Tarzana, Calif.) and containing either pp65 PepMix™ IE1 PepMix™ or IE2 peptide library (at a final concentration of 1 μg/ml of the individual peptides) at 37° C. in a 5% CO2-gassed incubator. After 1 h in culture, brefeldin A (GolgiPlug; Becton Dickinson Biosciences) was added, and incubation continued for an additional 11 h under the same conditions.

IVS using rMVA was modified from a published method (La Rosa et al. 2001). Briefly, cryopreserved PBMCs were rapidly thawed and immediately dispensed in a 12-well plate at a concentration of 2×106 cells/ml in RPMI 1640 medium (2.5 ml/well) supplemented with 10% human AB serum (COH Blood Bank) and were incubated with 5 μg/ml of both CpG-A ODN 2216 and CpG-B ODN 2006 (TriLink Biotechnologies, San Diego, Calif., USA). After 3 days, ODN-treated PBMCs were infected with rMVA expressing pp65 and IEfusion antigens (pp65-IEfusion-MVA), or rMVAexpressing pp65 and IE1 exon4 (pp65-IE1-MVA), or rMVA-expressing only IEfusion antigen (IEfusion-MVA) at a multiplicity of infection of 5, for 6 h in RPMI 1640 medium with reduced (2%) human AB serum. Infected PBMCs were γ-irradiated (2500 rad) and used as APC. APC were plated in a 24-well plate (1.5×106/well), co-incubated with autologous PBMC (3×106/well), in a final volume consisting of 2 ml/well RPMI 1640 medium with 10% human AB serum and human rIL-2 (NIH AIDS Research and Reference Reagent Program, 10 units/ml). Every 2 days, 50% of the culture medium was removed, and replaced with fresh medium containing rIL2. Cells were incubated for 8 days and split into additional wells when necessary. At day 8, cells were collected and washed with medium without rIL-2 and transferred into 15 ml Falcon tubes. The same stimulation conditions for intracellular cytokine (ICC) assays performed on ex vivo PBMC were used for PBMC after IVS.

Intracellular cytokine staining of human PBMC. After 12 hours of incubation, PBMC were harvested, washed, labeled with PE-conjugated anti-CD8 and FITC-conjugated anti-CD4 antibodies, fixed, and permeabilized (Cytofix-Cytoperm; Becton Dickinson Biosciences) before they were labeled with APC-conjugated antibody to IFN-γ. The stained cells were analyzed on a FACSCanto™ (BD Immunocytometry Systems, San Jose, Calif.), and data were analyzed using FCS Express (version 3.0; DeNovo Software). 0.5× 106 events were acquired for each sample. Lymphocytes were initially gated using forward versus side scatter, then CD4+ and CD8+ lymphocytes cells were gated separately. The number of IFN-γ expressing cells is shown as a percentage of the CD8+ or CD4+ lymphocyte population.

In vitro stimulation of mouse splenocytes and detection of cellular responses. Three weeks after immunization, spleens were aseptically removed and splenocytes from individual or pooled mice were stimulated in vitro (IVS) for 1 week with syngeneic LPS blasts as APC, loaded either with the relevant CMV-CTL epitope or CMV-peptide library (La Rosa et al. 2001; La Rosa et al. 2007). The immunological activity of the stimulated murine cultures was determined after assessing the levels of IFN-γ CD4+ or IFN-γ CD8+ T cells by ICC staining (La Rosa et al. 2001; La Rosa et al. 2007). For CD4, CD8, and IFN-γ labeling, APC-conjugated antibody to IFN-γ, PE-conjugated CD4, and FITC-conjugated CD8 were used (BD, San Jose, Calif.). Flow cytometric acquisition was performed on a FACSCanto™ (BD Immunocytometry Systems). Between 0.80 and 1.0×106 events were acquired for each sample. FACS analysis was performed using FCS Express version 2 software (De Novo, Ontario, Canada). The number of double-positive cells is expressed as a percentage of the CD8+ T cell population.

Statistical analysis methods. Ex vivo IFN-γ production versus post-IVS with rMVA by PBMC against pp65, IE1 and IE2 peptide libraries were compared using Friedman's test with 2 degrees of freedom, followed by Wilcoxon's rank-sum test for pairwise comparisons. Comparison of paired data before and after IVS with rMVA was performed using the Student T-test.

Construction of the IE1/e4-IE2/e5 Fusion (IEfusion) Gene, Cloning into Transfer Vector pZWIIA and Generation of Recombinant MVA.

IE1, also known as UL123 is composed of four adjacent exons interspersed with 3 introns. The adjacent UL122 (IE2) gene is composed of the same initial 3 exons UL 123 but also contains a unique adjacent exon5 as a result of alternate splicing (FIG. 9A) (White et al. 2007). To approximate the genetic architecture in the CMV genome and to reduce the number of independent transcription units to be inserted into MVA, exon4 (e4) from IE1 and exon5 (e5) from IE2 were joined as shown in FIG. 9B. Genomic copies of e4 and e5 were amplified from CMV strain AD169 viral DNA, and primers were developed that made use of a newly created restriction site in IE2/e5 that was introduced into the IE1/e4 fragment by PCR methods. The independent exons with overlapping sequence were joined at the newly created Apa I site to create the fusion gene without introduction of new protein sequence. Exons 2-3 were omitted because they contain transcriptional activation domains whose activity might cause unexpected and undesirable gene activation events. (Gyulai et al. 2000; Johnson et al. 1999).

Figure 9D:
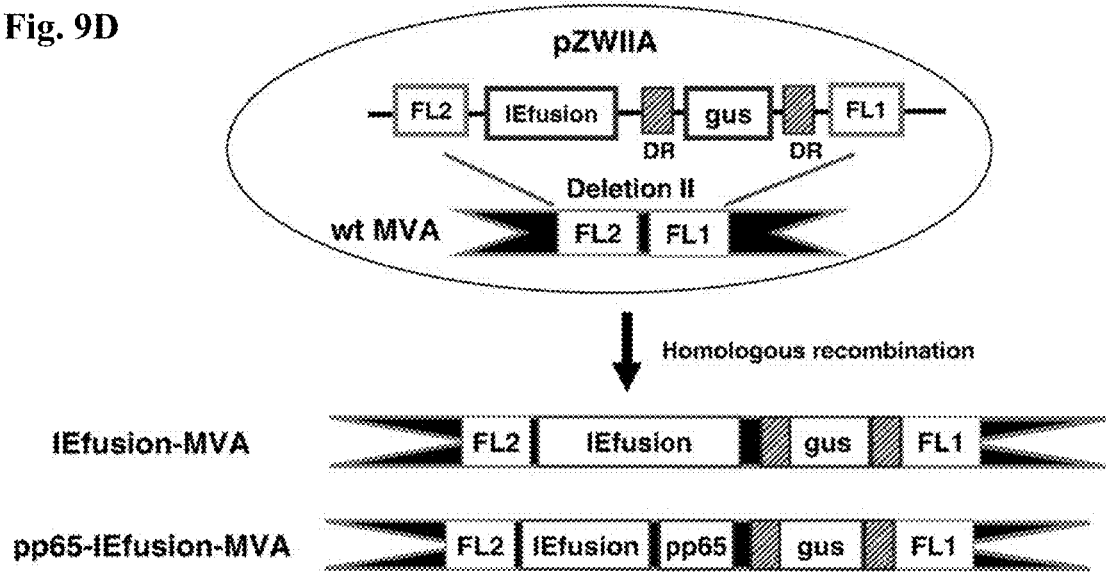
FIG. 9D illustrates the generation of IEfusion-MVA and pp65-IEfusion-MVA. IEfusion-pZWIIA or pp65-IEfusion-pZWIIA was transfected into wtMVA infected CEF cells to generate IEfusion-MVA or pp65-IEfusion-MVA via homologous recombination at deletion II whose flanking region is contained in the plasmid that is homologous to wtMVA.

The fusion gene was cloned into pZWIIA using unique restriction enzymes that were added by PCR to the ends of each exon (FIG. 9C). Versions of the transfer plasmid pZWIIA with UL83 (pp65) were also constructed (FIG. 9C). pZWIIA encodes two direct repeats flanking the bacterial marker gene (such as glucoronidase or gus) that facilitates their removal through stochastic recombination as earlier described (Wang et al. 2004). Both versions of pZWIIA were used in combination with wild type MVA to generate rMVA expressing the IEfusion gene alone or co-expressed with pp65 (FIG. 9D). The pp65 gene was kept separate from the IEfusion gene in the MVA shown in FIG. 9D. Each rMVA underwent ~8 rounds of purification, and was verified to be absent of parental wild type MVA (wtMVA) using PCR methods (Wang et al. 2007).

Figure 10A:
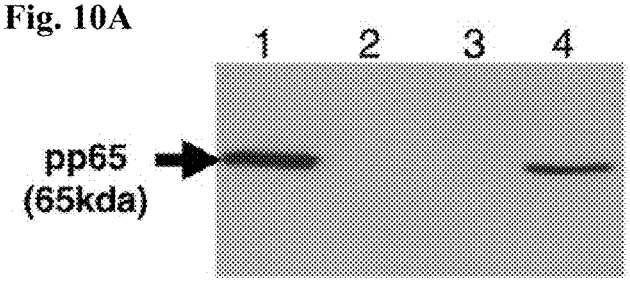
FIG. 10A is a Western blot (WB) detection of the pp65 protein antigen. Lane 1: CEF cell lysate infected with pp65-rMVA as (+) control; Lanes 2 and 3: cell lysate from wtMVA-infected and uninfected CEF as (−) controls; Lane 4: cell lysate of pp65-IEfusion-MVA-infected CEF cells. The WB in Panel A was incubated with mAb 28-103 against pp65.
Figure 10B:
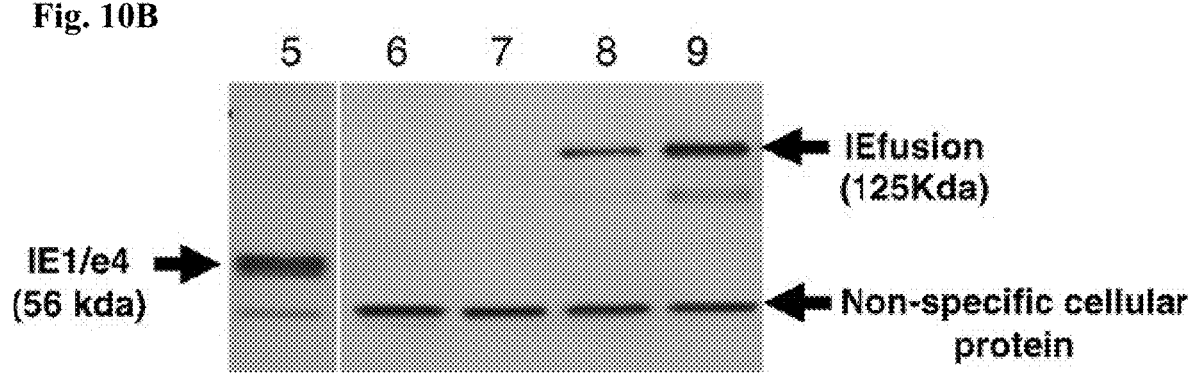
FIG. 10B is a Western blot (WB) detection of IEfusion protein antigens. Lane 5: cell lysate of CEF infected with rMVA expressing IE1/e4 as (+) control; Lanes 6 and 7: cell lysate from wtMVA-infected and uninfected CEF as (−) controls; Lane 8: cell lysate of pp65-IEfusion-MVA-infected CEF cells and Lane 9: cell lysate of IEfusion-MVA-infected CEF cells. The WB incubated with mAb p63-27 against IE1.

The artificial joint between IE1/e4 and IE2/e5 was tested as to whether it would allow continuous translation of the predicted full length protein product, by infecting chicken embryo fibroblast cells (CEF) with wtMVA and simultaneous transfection with pZWIIA containing the IEfusion gene. The results show a 125 kDa protein band composed solely of the IE1/e4 and IE2/e5 exons, detected using an IE1/e4-specific mAb that also detected the expected 60 kDa band after infection of CEF with IE1/e4-MVA (Wang et al. 2007). Virus plaques expressing the IEfusion gene with and without separately co-expressed pp65 were amplified, and titered viruses were used to make lysates that were separated using SDS-PAGE, followed by WB analysis using antibodies to detect pp65 (FIG. 10A) and IEfusion proteins (FIG. 10B). The results confirm that the IEfusion protein can be highly expressed alone or in combination with pp65 (FIG. 10).

Immunogenicity of rMVA that Expresses IEfusion Alone or in Combination with pp65.

In transgenic HLA A2 mice. To establish whether rMVA would elicit primary immunity in a CMV naive host, experiments were performed in transgenic (Tg) mice naive to all antigens expressed from the rMVA. HHDII mice which are Tg for the HLA A2 gene and focus presentation on the human MHC were immunized with the IEfusion-MVA or pp65-IEfusion-MVA for three weeks (Pascolo et al. 1997). Spleens were processed and in vitro stimulation (IVS) was set up for a period of 7 days followed by intracellular cytokine assay (ICC) to detect IFN-γ expression. To evaluate the HLA A2-restricted CD8+ T cell response, immunodominant HLA A2-restricted pp65 and IE1 CTL epitopes were used, as well as the IE2 peptide library, as no HLA A2-restricted IE2 epitopes have yet been defined (Wang et al. 2004b; Wang et al. 2007). To measure MHC Class II CD4+ T cell responses, peptide libraries specific for the pp65, IE1, and IE2 antigens were used both during the IVS and ICC stimulations.

Figure 11:
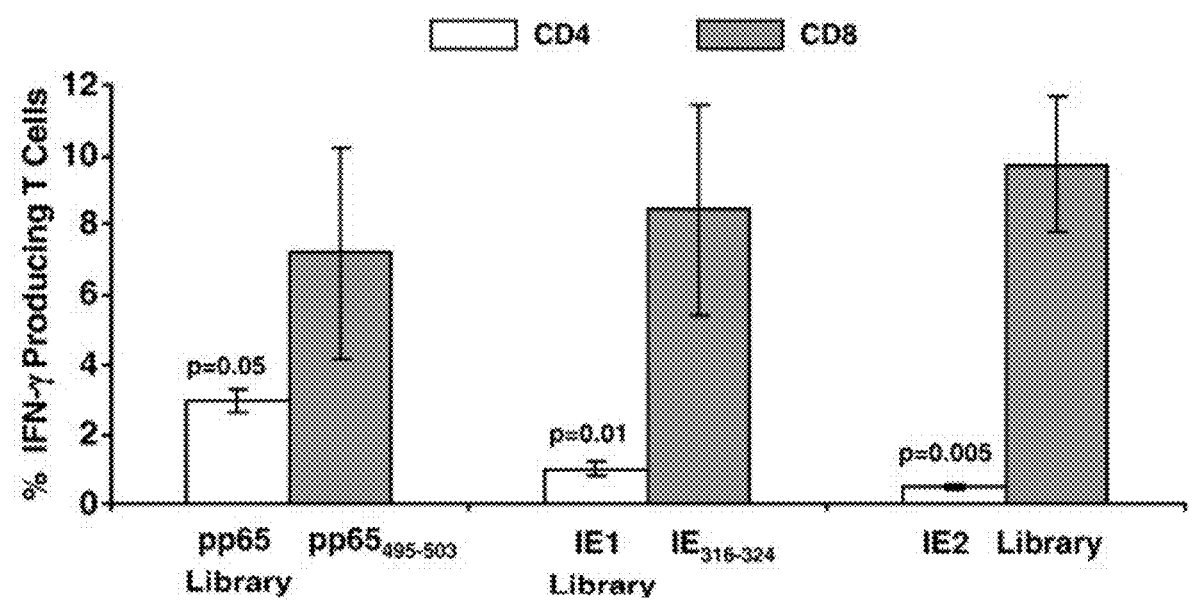
FIG. 11 is a bar graph showing the percentage of interferon-gamma (IFN-$\gamma$) producing splenocytes specific for pp65, IE1 and IE2 (x axis) in three HHDII mice immunized with 50 million pfu of pp65-IEfusion-MVA. Grey bars represent pp65-, IE1- and IE2-specific IFN-$\gamma$ production by CD8+ T cells using either peptide epitopes or libraries (identified below the x axis) during IVS and ICC stimulations. Unfilled bars represent simultaneous pp65-, IE1- and IE2-specific IFN-$\gamma$ production by CD4+ T cells, following IVS and ICC stimulation with the corresponding CMV libraries indicated below each set of bars. IVS and ICC stimulation conditions are described in Example 1. In all graphs, error bars represent standard error of the mean among the immunized mice (N=3). In all experiments, IFN-$\gamma$ production to mock stimulated cells was subtracted. P values indicate statistically significant differences measured by T-test.

The results presented in FIG. 11 demonstrate robust immunogenicity of the rMVA after infection in the HHDII mouse. Levels of specific IFN-γ produced by CD8+ T cells were significantly higher than for CD4+ T cells for all 3 CMV antigens. In contrast, both a robust CD4+ and CD8+ T cell response was found for pp65 (FIG. 11). Likewise, there was substantial recognition of the IE1/e4 portion of the IEfusion protein demonstrated by a potent CD8+ T cell response using the IE1 peptide library (FIG. 11). Finally there was a good CD8+ T cell response to the IE2 library, and a lesser response by CD4+T cells (FIG. 11). The immunogenicity of the IEfusion protein was not dependent on the presence of the pp65 antigen by immunizing HHDII mice with an MVA that included the IEfusion protein without coexpression of pp65. The HHDII mice responded similarly to the IE2 library, and also appropriately responded to the HLA-A2 restricted epitope of IE1 in a robust manner. These experiments confirm the strong immunogenicity of the IEfusion protein, and also verify that the immunogenicity of the IE1 portion of the molecule is not disrupted when the IE2 portion is fused to it. The immunogenicity of the IE1 portion compares favorably to constructs in which IE1/e4 is expressed as a single exon without fusion (Wang et al. 2004b; Wang et al. 2007).

Figure 12:
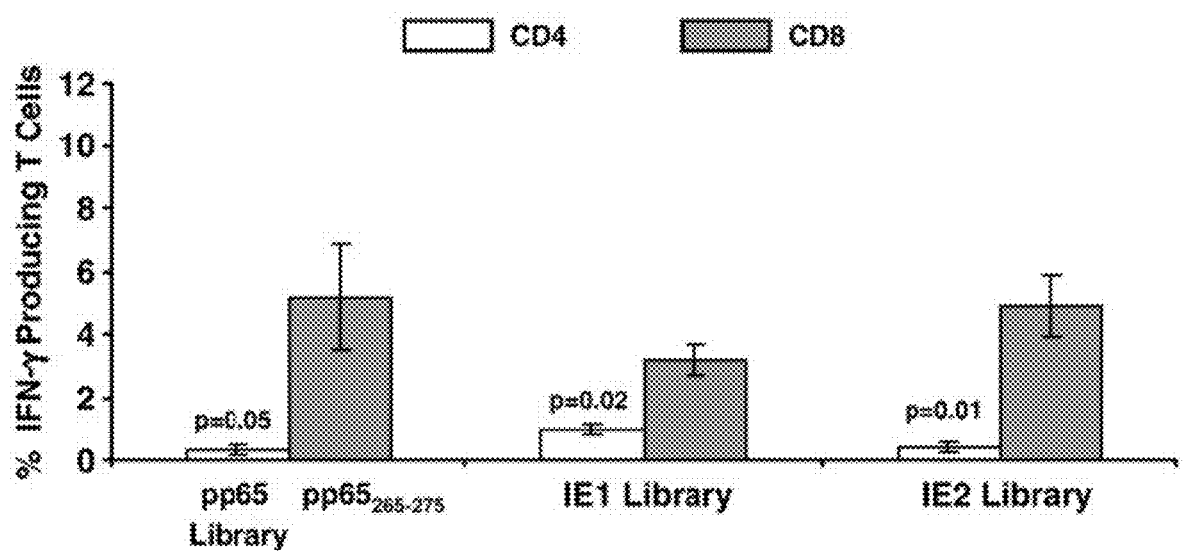
FIG. 12 is a bar graph showing the percentage of IFN-$\gamma$ producing splenocytes assessed by flow cytometry specific for pp65 (CTL epitope or library), IE1 and IE2 peptide libraries (x axis) in three B7 mice immunized with 50 million pfu of pp65-IEfusion-MVA, using methods as described in the legend to FIG. 11. In all graphs, error bars represent standard error of the mean among the immunized mice (N=3). In all experiments, IFN-$\gamma$ production to mock stimulated cells was subtracted. P values indicate statistically significant differences measured by T-test.

Immunization of Tg HLA B7 Kb$^{ko}$/Db$^{ko}$ mice with pp65-IEfusion-MVA. The success of the immunogenicity trial in HHDII mice led to an investigation of a Tg model expressing a different HLA allele to generalize the scope of immunogenicity of the rMVA in different HLA backgrounds. B7 mice are deficient in both Kb and Db murine genes, and mainly process Class I antigens using the Tg MHC molecule, HLA B*0702 (Rohrlich et al. 2003). Immunization conditions were similar as we described for HHDII mice, and after three weeks, mice splenocytes were stimulated during both IVS and ICC procedures with HLA B*0702pp65$_{265-275}$ epitope to evaluate the Tg CD8+ T cell response. In B7 mice, the recognition of HLA B*0702 IE1 epitopes is minimal, thus the IE1 peptide library was used to measure the Tg CD8+ T cell response (FIG. 12). Peptide libraries specific for the pp65, IE1, and IE2 antigens were also used to evaluate the MHC Class II responses. Similar to the findings in HHDII mice, higher levels of CD8+ and lower levels of CD4+ T cell responses were elicited against all 3 CMV antigens (FIG. 12). This demonstrates that both the pp65 and IEfusion genes are functional and immunologically recognized in the Tg HLA B7 mouse model.

Figure 13A:
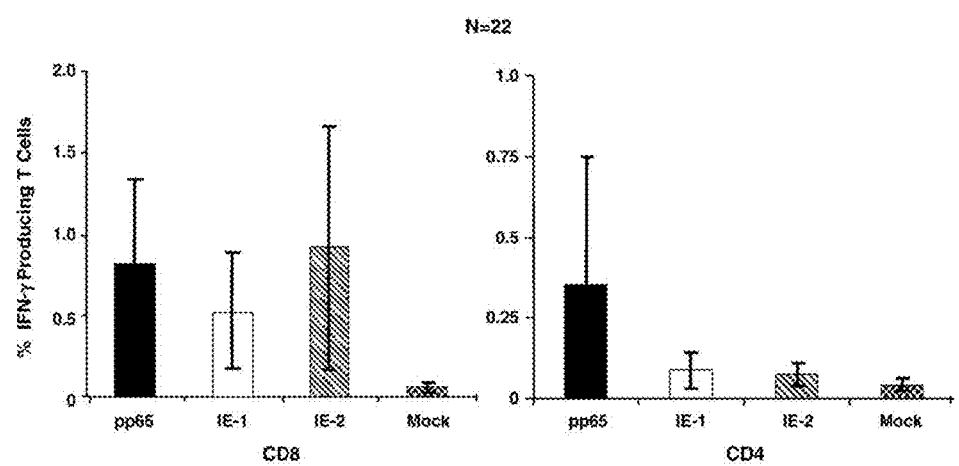
FIG. 13A is a pair of bar graphs showing ex vivo response to pp65, IE1, and IE2 peptide libraries in healthy volunteers. PBMC were obtained from N=22 healthy volunteers for which we had complete HLA typing. Five million PBMC were divided into four aliquots and were individually co-incubated with peptide libraries at 1 µg/ml/peptide in single use aliquots as described in Example 1. PBMC from each individual were treated in separate cultures with each peptide library at the same time, but not all individuals were evaluated on the same day. Standard gating procedures were employed for each individual flow acquisition, such that conditions were standardized for all evaluations. Separate aliquots from the ICC assay were incubated with CD4+, CD8+ or isotype control antibodies as described in Example 1. The plots show the percentage of T Cells that produce IFN-$\gamma$ for each antigen-specific peptide library. Error bars represent the standard error of the mean calculated using Microsoft Excel statistical package.

Ex vivo response to CMV0pp65, IE1 and IE2 peptide libraries in healthy volunteers and stem cell transplant (HCT) recipients. To gauge the strength of the rMVA to stimulate CMV-specific T cells from PBMC of CMV positives, ex vivo recognition of the three peptide libraries (pp65, IE1, IE2) corresponding to the cognate expressed proteins in rMVA was examined. Data was taken from 22 CMV-positive (FIG. 13) and 8 CMV-negative healthy adult volunteers and classified individuals as a responder if they had antigen-specific T cell frequencies of greater magnitude than levels found in CMV negatives, which averaged 0.05% of CD8+ and 0.05% of CD4+ T cells for each of the 3 peptide libraries. The number of individuals classified as responders was highest for pp65 in both the CD8 (16/22) and CD4 (10/22) subsets, and there were lower numbers of responders (9/22) for both the IE1 and IE2 library in CD8, but far fewer (3/22) in the CD4 subset. The number of individuals responding to the 3 peptide libraries is qualitatively similar to the only other comparable dataset (Sylwester et al. 2005). The CMV-specific CD8+ and CD4+ T cell frequencies for each of the 22 CMV positives were calculated, and roughly equivalent responses to all 3 libraries in the CD8+ T cell subset were found (FIG. 13A). In contrast, there was a dichotomy of response in the CD4+ T cell subset such that pp65 responses had a 3-fold higher average than IE responders, which is in line with previous findings (Sylwester et al. 2005). In summary, the T cell responses in the chosen group of CMV positive individuals confirm the reliability and the legitimacy of using results from a healthy volunteer group as a benchmark for comparisons with less well characterized HCT patients.

Figure 13B:
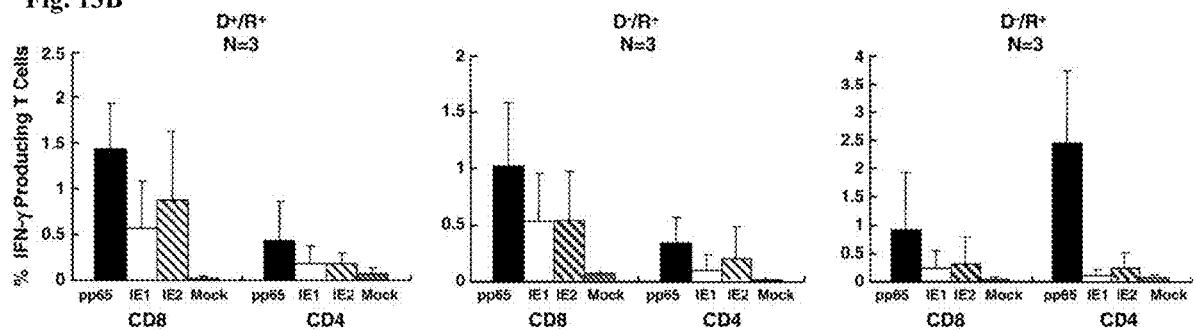
FIG. 13B is a set of bar graphs showing ex vivo response of PBMC from HCT recipients. Three examples from each of three separate risk categories of HCT shown in 3 separate plots (L–R; D+/R+, D−/R+, D−/R+) based on CMV status were evaluated for response against peptide libraries using the same technical approach as described in A). Data from all 3 individuals was averaged in each category, and the error bars represent the standard error of the mean.

Next, the immune response in HCT recipients was investigated in relation to all three peptide libraries in three combinations of donor (D) and recipient (R) pairs with increasing risk for complications of CMV infection (D+/R+, D+/R− and D−/R+) at 180 days post-transplant (FIG. 13B). All 9 recipients that we chose were part of a study of natural development of immunity to CMV and were known responders to CMV antigens (Gallez-Hawkins et al. 2005; Lacey et al. 2006). All 9 patients responded to the 3 peptide libraries by producing a CD8+ T cell response of similar magnitude to healthy adults with chronic CMV infection (FIG. 13A). Similar to the results for healthy volunteers, the pp65 library stimulated a strong response in both the CD4+ and CD8+ T cell subset, while the IE1 and IE2 libraries were most effective for stimulating a CD8+ T cell response (FIG. 13B). The low level of CD4+ T cell response to both the IE1 and IE2 libraries consistent with previous reports and the current results in healthy volunteers. These observations indicate that both the magnitude and quality of the T cell response to the pp65, IE1, and IE2 antigens are similar in recovering HCT recipients as it is in healthy CMV-positive volunteers.

Figure 14A:
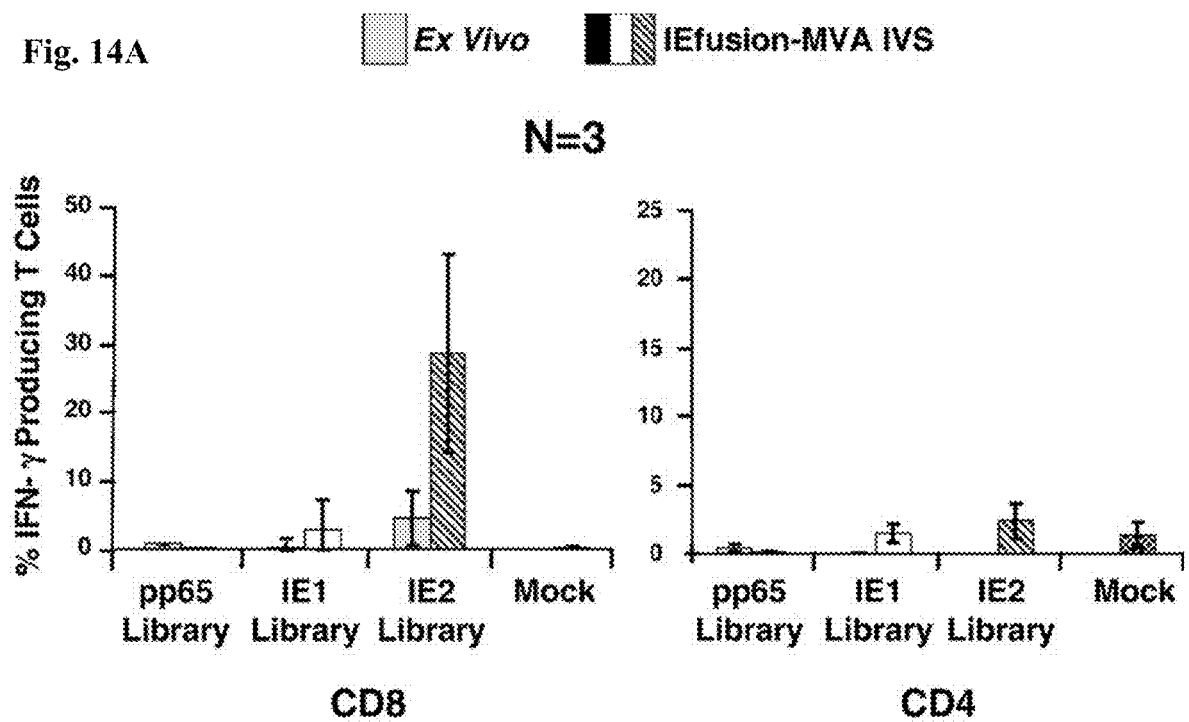
FIG. 14A is a pair of bar graphs showing that rMVA stimulates CMV-specific T cells in human PBMC. Using the IEfusion-MVA, as described in Example 1, APC were infected for 5-6 hours, irradiated, and then coincubated with unmanipulated PBMC from the autologous individual. The time course and conditions of the IVS are described in Example 1. Four separate evaluations were conducted with each IVS culture as shown in Panel A. After treatment with the peptide library and ICC was performed, aliquots of PBMC were either stained with CD4 or CD8 antibodies as described in FIG. 13A. Results shown are averages of measurements from three CMV-positive individuals selected randomly from a group of blood donors. Not shown is a comparison with a CMV-negative donor who showed no specific recognition of any of the three peptide libraries after IVS with IEfusion- and pp65-IEfusion-MVA.

IEfusion-MVA stimulates CMV-specific T cells in human PBMC. The immunogenicity of the IEfusion protein as a single immunogen or co-expressed with pp65 in rMVA was examined. Autologous antigen presenting cells (APC) were matured to be optimally receptive to MVA infection and antigen presentation by the use of a CpG DNA cocktail (La Rosa et al. 2006). Following three days of maturation, APC were infected with rMVA containing the IEfusion gene or rMVA containing both the IEfusion and pp65 genes, followed by irradiation to inactivate the APC for proliferation. IEfusion-MVA in PBMC from three CMV-positive healthy donors and one CMV-negative donor was then examined. First, ex vivo recognition of either the IE1 or IE2 peptide libraries was conducted as a comparison to the MVA IVS study (FIG. 14A). The average increase was quite substantial after IVS with IEfusion-MVA (nearing 5-fold) in each of the three CMV-positive individuals evaluated in either the CD4+ or CD8+ subset as detected with the IE1 or IE2 peptide libraries (FIG. 14A). In contrast, there was no evidence for ex vivo recognition of peptide libraries in the CMV-negative individual, nor was there any significant stimulation of either IE-specific T cell population. No evidence of pp65-specific stimulation beyond ex vivo levels was found in CMV positives or negatives, because the rMVA did not express pp65.

Figure 14B:
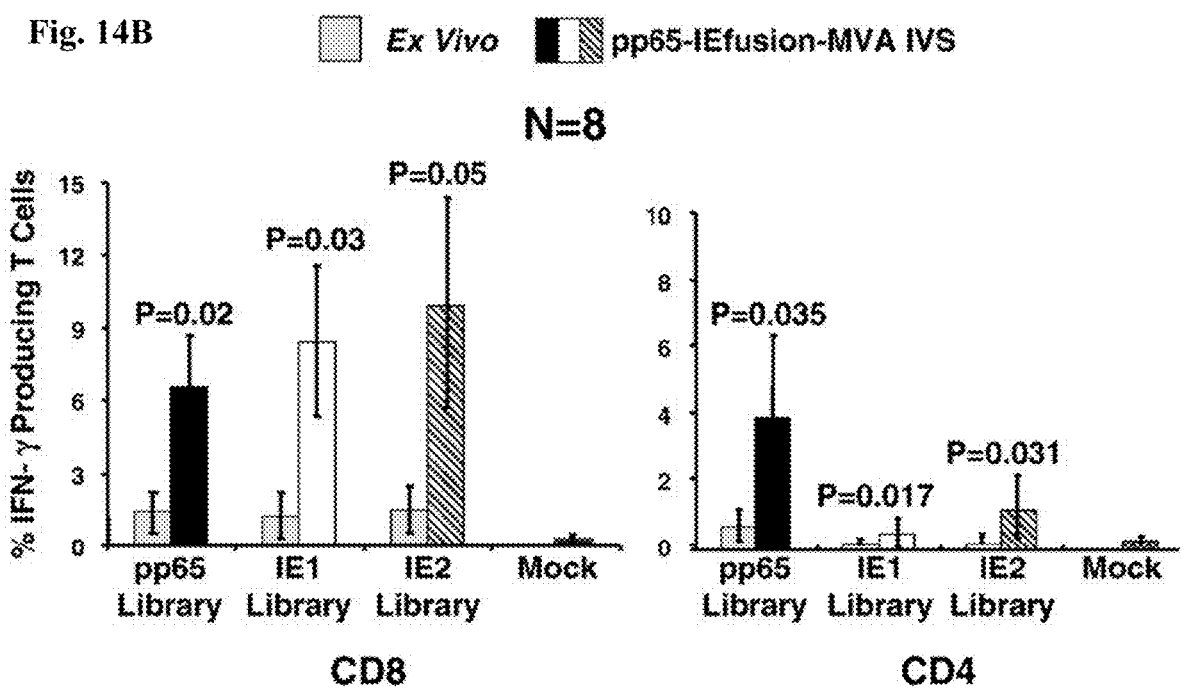
FIG. 14B is a pair of bar graphs showing results of the same protocol as in FIG. 14A, but using the pp65-IEfusion-MVA. PBMC from 8 healthy CMV positive blood donors were evaluated both ex vivo without manipulation and post-IVS following infection with rMVA as described in FIG. 14A. Statistical differences between ex vivo levels of CMV-specific T Cells versus post-IVS were calculated as described in Example 1. When a P value is ≤0.05, it is shown above the error bar for each evaluation of individual peptide libraries. All methods for IVS, ICC, and flow cytometry are described in Example 1.
Figure 15:
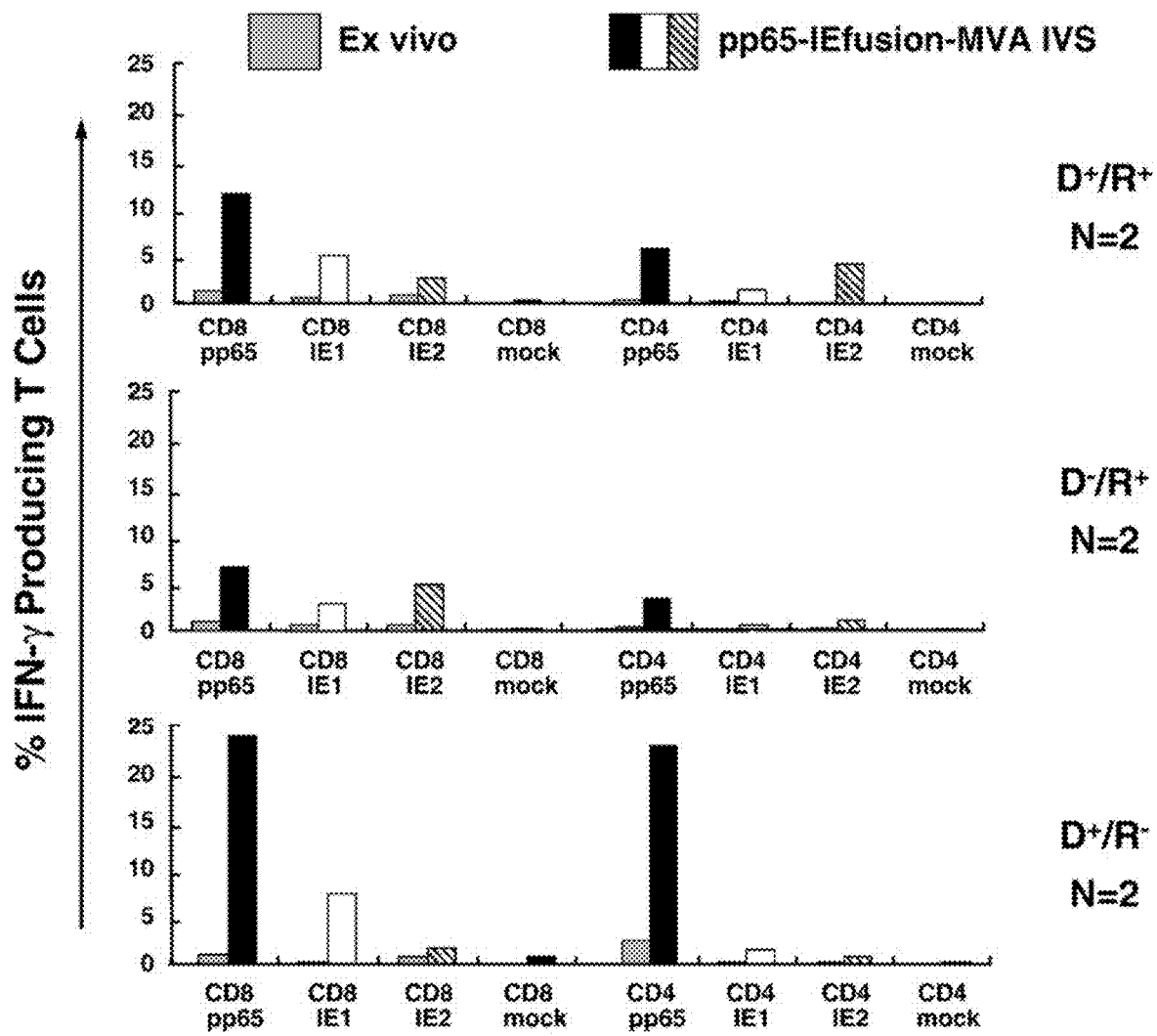
FIG. 15 is a set of bar graphs showing that rMVA stimulates CMV-specific T cells in PBMC from HCT recipients. Six examples of patients that were evaluated for response to peptide libraries shown in FIG. 13B were also evaluated after IVS with pp65-IEfusion-MVA. Methods including conditions for IVS, post-IVS analysis of cell population, ICC, and flow cytometry are identical as described in FIG. 14. A comparison was made between the ex vivo level versus post-IVS for each stimulation, and each category of donor and recipient serostatus is shown in 3 separate plots as discussed in the legend to FIG. 13B.

The immunogenicity of pp65-IEfusion-MVA was assessed by comparison to ex vivo measurements of the autologous PBMC populations using all three peptide libraries (FIG. 14B). In all individuals examined, there was brisk stimulation of antigen-specific T cell populations that often exceeded levels found with IEfusion-MVA (FIG. 14A). In the case of the CD8+ T cell subset, IVS caused substantial increase in all three antigen-specific T cell populations. The ex vivo level of the CD4+ subset recognizing pp65 was far greater than for the IE antigens, which was also reflected in the amplified frequencies after IVS with rMVA. The same CMV-negative healthy donor that was investigated with IEfusion-MVA, had no evidence of pp65 or IEfusion-specific immunity after in vitro immunization with pp65-IEfusion-MVA. Results from both vaccine viruses establish that rMVA stimulation does not substantially alter the relationship of the T cell subset proportion measured ex vivo for all three antigens; it amplifies ex vivo levels to a higher level after IVS (FIGS. 14A and B). As a further control for specificity of CMV antigen recognition, in vitro immunization of PBMC from 3 healthy donors was investigated as shown in FIG. 14B with an MVA only expressing the gus gene (gus-MVA) that was constructed using different transfer vectors and described in a previous report (Wang et al. 2004a). There was no incremental increase in CMV-specific recognition of all 3 peptide libraries greater than what was measured ex vivo.

rMVA stimulates CMV-specific effectors in PBMC from transplant recipients. Next, the capability of the three-antigen rMVA to stimulate memory responses in PBMC from HCT recipients was evaluated. Two examples were chosen from three different risk categories of patients that were also examined ex vivo: O+/R+, O−/R+ and O+/R− (FIG. 13B). Results of the IVS with MVA are shown side-by side with the ex vivo response to demonstrate the magnitude of the stimulation of CMV-specific T cell responses in all patient risk groups (FIG. 15). The CD8+ was more substantial than the CD4+ T cell stimulation which reflected the ex vivo profile, which shows substantial over-representation of CD8 versus CD4 responses (FIG. 15). The levels of rMVA amplification of CMVspecific T cells in many cases exceed those found in healthy volunteers (FIGS. 14 and 15). This is evident in both the CD4 and CD8 T cell populations, and is observed in all three patient groups with different combinations of CMV serostatus. While not all antigens were equally stimulated in all patients, the majority of measurements demonstrate a substantial amplification from ex vivo levels in both the CD4+ and CD8+ T cell population. The specificity of the immune responses to CMV antigens was confirmed by including an additional in vitro immunization culture using gus-MVA, from two of the six HCT patients that had sufficient PMBC to conduct this additional control. There was no evidence of CMV-specific immune stimulation, beyond what was measured ex vivo from both individuals (FIG. 15).

Example 2

Increased Stability of CMV Antigens Under Control of mH5 Promoter

Materials and Methods

Cells, virus, peptides, and mice. Primary CEF cells prepared from specific pathogen-free chicken eggs were purchased from Charles River SPAFAS (North Franklin, Conn., USA). BHK-21 cells (ATCC CCL-10) were purchased from American Type Cell Collection (Manassas, Va., USA) and maintained in minimal essential medium (MEM) supplemented with 10% fetal calf serum in a 37° C. incubator containing 5% CO2.

Wild type (wt) MVA virus stock, pLW51 and pSC11 transfer plasmids were kindly provided by Dr. Bernard Moss (Laboratory of Viral Diseases, NIAID, NIH). rMVA expressing CMV pp65 alone (pSyn-pp65-MVA) or together with IE1/e4 under control of pSyn promoter (pSyn-pp65-IE1/e4-MVA) were generated as previously described [Wang et al. 2007]. rMVA expressing CMV pp65, IEfusion protein (IE1/e4 and IE2/e5) under control of pSyn promoter (pSyn-pp65-IEfusion-MVA) were also developed using a homologous recombination method (Wang et al. 2008).

Construction of MVA transfer plasmids and viruses containing mH5 promoters. pZWIIA transfer vector containing two pSyn promoters was constructed as previously described (Wang et al. 2007). Additional MVA transfer plasmids were constructed after replacement of pSyn with the mH5 promoter. The two pSyn promoters in pZWIIA were replaced with one mH5 promoter. Briefly, a 228 bp DNA fragment including the 70 bp mH5 promoter sequences and multiple cloning sites was synthesized (Genebank accession # FJ386852) and cloned into pZERO-2 (Integrated DNA Technologies, Coralville, Iowa). This 228 bp DNA fragment was excised with Xho I and Not I, gel purified and cloned into pZWIIA to yield mH5-pZWIIA. The mH5-pZWIIA was then modified to replace the bacterial gus (β-glucuronidase) marker gene with the Venus™ fluorescent marker gene (Clontech, Mountain View, Calif., USA) to improve the speed of rMVA screening. The CMV pp65 gene was cloned into mH5-pZWIIA to yield mH5-pp65-pZWIIA. The IEfusion gene was cloned into mH5-pZWIIA to yield mH5-IEfusion-pZWIIA, and an MVA transfer plasmid was used to generate mH5-IEfusion-MVA. To make rMVA expressing both pp65 and IEfusion protein simultaneously, a new MVA transfer vector that contained mH5 promoter and targets MVA deletion III region was constructed based on the pLW51 plasmid. pLW51 was then modified by replacing the original expression cassette by excision at XhoI and AscI sites and inserted the mH5 promoter followed by the CMV pp65 gene to yield mH5-pp65-pLW51. The structure of MVA transfer vectors (mH5-pp65-pZWIIA, mH5-IEfusion-pZWIIA and mH5-pp65-pLW51) were verified by restriction enzyme digestion and DNA sequence analysis.

mH5-pp65-MVA was generated by transfecting mH5-pp65-pZWIIA into wtMVA-infected BHK-21 cells and screened based on the Venus™ fluorescent marker to eliminate wtMVA as previously described (Wang et al. 2006). mH5-pp65-IEfusion-MVA was generated in two steps. First, mH5-IEfusion-MVA was generated by transfecting mH5-IEfusion-pZWIIA into BHK-21 cells infected with wtMVA in six-well plates. mH5-IEfusion-MVA was screened to eliminate wtMVA based on Venus™ fluorescent marker expression. mH5-IEfusion-MVA was expanded on BHK-21 cells after 8-10 rounds of screening to create a stock for the 2nd round of gene insertion after verification that wtMVA was eliminated. Next, mH5-pp65-pLW51 was transfected into BHK-21 cells that were simultaneously infected with mH5-IEfusion-MVA. mH5-pp65-IEfusion-MVA was screened based on the bacterial gus gene marker for 8-10 rounds until parental virus (mH5-Iefusion-MVA) was removed completely. mH5-pp65-MVA and mH5-pp65-Iefusion-MVA were expanded on BHK-21 cells to create virus stocks that were stored long term at −80° C.

Stability analysis of individual rMVA isolates from passage 10. rMVA with expression cassettes based on mH5 (mH5-pp65-MVA, mH5-pp65-IEfusion-MVA) or pSyn promoters (pSynpp65-IE1/e4-MVA, pSyn-pp65-IEfusion-MVA) were consecutively passaged 10 times on either CEF or BHK-21 cells. Briefly, a 150 mm tissue culture dish of either CEF or BHK-21 cells was infected with rMVA at multiplicity of infection of 0.1 (MOI=0.1). rMVA was harvested 48 h after infection, resuspended in 1.0 ml of MEM containing 2% fetal calf serum (MEM-2) and subjected to 3×freeze/thaw cycles followed by sonication to release the virus. The virus from each passage was subsequently titrated on either CEF or BHK-21 cells and after adjustment to an MOI of 0.10, it was used for the next passage. DNA samples of each passage were obtained for qPCR analysis using the Qiagen™ column purification kit according to manufacturer's instructions (Valencia, Calif., USA). Cell lysates of each passage used for Western blot (WB) analysis were prepared from 100 mm dishes of either CEF or BHK-21 cells infected with the same number of pfu of rMVA of each serial passage.

To further characterize virus plaques from passage 10 (P10) of pSyn-pp65-IE1/e4-MVA, individual plaques were isolated from P10 virus stock by plaque purification. Briefly, P10 virus stock of pp65-IE1/e4-MVA (pSyn) was titrated by immunostaining using anti-vaccinia polyclonal sera (AbD serotech, Raleigh, N.C., USA), diluted and distributed at 0.5 pfu per well into 96-well plates. At 4 days post-infection, 18 wells that appeared to be infected by no more than one virus isolate were collected, expanded and analyzed by WB for CMV-pp65 expression levels. Six individual plaques from P1 were also isolated at random using the same method.

Western blot (WB) detection of rMVA protein expression. Protein expression levels of the pp65, IE1/e4 and IEfusion genes from pSyn-pp65-IE1/e4-MVA, pSyn-pp65-IEfusion-MVA and mH5-pp65-IEfusion-MVA infected cells were measured by Western blot using the Amersham ECL Plus™ detection kit (Amersham Pharmacia Biotech, Buckinghamshire, United Kingdom). Cell lysates were separated by SDS-PAGE on 10% gels. After electro-transfer of proteins from the gel onto PVDF membranes (Bio-Rad, Hercules, Calif.), the blots were incubated with purified mAb 28-103 (against pp65) or mAb p63-27 (against IE1), then washed and further incubated with HRP-labeled goat anti-mouse Ab according to the manufacturer's instructions (Amersham Pharmacia Biotech™).

Southern blot detection of CMV-pp65 and IE1/e4 insertion gene in rMVAs. To determine the presence of the pp65 and IE1/e4 gene in individual pp65-IE1/e4-MVA isolates after P10, southern blot (SB) was performed. Briefly, a 150 mm culture dish of BHK-21 cells was infected with individual pp65-IE1/e4-MVA isolates at MOI=1 and incubated at 37° C. for 24 hours. The MVA viral genomic DNA was isolated according to a described method (Cwynarski et al. 2001). Briefly, cells were homogenized in 1.25 ml hypotonic buffer (10 mM Tris-HCl, pH 7.8 containing 12 mM KCl followed by incubation with 450 units of micrococcal nuclease (Sigma-Aldrich St. Louis, Mo.) for one hour at 25° C. to digest cellular DNA. The reaction was stopped by adding EGTA (glycol-bis(2-aminoethylether)-N,N,N',N'-tetraacetic acid). Cell lysates were treated with proteinase K for one hour at 25° C. to release MVA viral DNA and then extracted using the phenol/chloroform method. For SB, MVA viral DNA was digested with Pme I and Nhe I restriction enzymes to excise the 3.9 Kb fragment containing the foreign gene cassette, separated on a 1% agarose gel and transferred to nylon membrane. This filter was hybridized with a $^{32}$P-labeled DNA probe specific for both pp65 and IE1 exon4 gene and exposed to HyPerfilm (Amersham Bioscience, Piscataway, N.J. 08855).

qPCR to measure DNA copy number. MVA viral DNA was extracted using a Qiagen QIAmp miniprep kit according to the manufacturer's instructions (Qiagen, Valencia, Calif.). The plasmid DNA used to generate the standard curve was made by inserting both the pp65 and IEfusion gene into the pSC11 vector containing the TK gene (La Rosa et al. 2002). The absolute concentration of the plasmid was measured by two independent means: $OD_{260}$ by UV spectrophotometry and a fluorophore-based method using Quant-iT™ Picogreen® dsDNA kit (Invitrogen™ Carlsbad, Calif., USA). The concentration was converted to plasmid copy number using the molecular weight of the plasmid DNA. Quantitative PCR primers of target genes were designed based on standard qPCR conditions using Primer Express Software Version 3.0 (Applied Biosystems Inc., Foster City, Calif., USA) and listed in Table 1, below. Quantitative PCR was performed using an ABI 7300 real-time PCR system and Power SYBR green master mix (SYBR) kit (Applied Biosystems). Briefly, 5 mL of MVA genomic DNA was amplified in a mixture of 25 μL containing 1 μM forward, 1 μM reverse primers and SYBR solution. The thermal cycling conditions were 95° C. for 10 min, 40 cycles of 95° C. for 15 seconds, and ending with one cycle at 60° C. for 30 seconds. Gene copy numbers were calculated using ABI sequence detection system software (SDS). The ratio of insert CMV genes and MVA backbone (ratio=CMV gene copy number/MVA backbone computed copy number) was calculated for each passage.

TABLE 1

Quantitative PCR Primers.

| Name | Forward or Reverse | Sequence | SEQ ID NO |
|---|---|---|---|
| pp65 | Forward | 5' ATCAAACCGGGCAAGATCTCGC 3' | 1 |
| pp65 | Reverse | 5' ATCGTACTGACGCAGTTCCACG 3' | 2 |
| IE1 exon4 | Forward | 5' CCATCGCCGAGGAGTCAGAT 3' | 3 |
| IE1 exon4 | Reverse | 5' AGTGTCCTCCCGCTCCTCCT 3' | 4 |
| IEfusion | Forward | 5' AAGTTGCCCCAGAGGAAGAG 3' | 5 |
| IEfusion | Reverse | 5' CTGCTAACGCTGCAAGAGTG 3' | 6 |
| TK | Forward | 5' TGTGAGCGTATGGCAAACGAA 3' | 7 |
| TK | Reverse | 5' TCGATGTAACACTTTCTACACACCGATT 3' | 8 |

Immunogenicity of mH5-pp65-IEfusion-MVA using human PBMC. CMV-positive healthy volunteers were enrolled in an IRB-approved protocol with informed consent. Whole blood was collected Human peripheral blood mononuclear cells (PBMC) were collected, purified using Ficoll™ and cryopreserved at −80° C. All human blood samples were considered discard and anonymous, except for HLA A and B typing information provided to investigators without other identifiers. IVS of PBMC using rMVA was performed according to previously described methods (La Rosa et al. 2006, Wang et al. 2007). Briefly, cryopreserved PBMC were rapidly thawed and cultured with both CpG-A ODN 2216 and CpG-B ODN 2006 (TriLink BioTechnologies, San Diego, Calif., USA). After 3 days, PBMCs were infected with rMVA for 6 hours, γ-irradiated (2500 rads) and used as APC incubated with autologus PBMC for 7 days.

PBMC that were harvested at 8 days post-IVS and incubated with either CMV-pp65 or IEfusion peptide library for 12 hours in the presence of brefeldin A, then washed and labeled with PE-conjugated anti-CD8 and FITC-conjugated anti-CD4 antibodies, fixed, and permeabilized (Cytofix-Cytoperm; BD Biosciences) before they were labeled with APC-conjugated antibody to IFN-γ. The stained cells were analyzed on a FACSCanto™ flow cytometer (BD Biosciences). Comparison of paired data between P1 and P7 of mH5-pp65-IEfusion-MVA was performed using the student t-test based on two-tailed procedure. The P values were considered significant if <0.05.

Immunogenicity of rMVA in HHD II Tg mice. Immunogenicity of m H5-pp65-mH5-IEfusion-MVA of passage 1 and 7 also was tested in HHD II mice (HLA A2.1). HHD II mice (Tg HLA A2.1) were used at 6-12 weeks for immunization and were bred and maintained under SPF conditions in a centralized animal care facility. HHD II mice were immunized with 5×10$^7$ pfu of purified rMVA intraperitoneally (i.p.). Spleens were removed three weeks after immunization and were stimulated in vitro for one week using a simplified protocol with HLA-matched human EBV-LCL (Krishnan et al. 2008) as antigen presenting cells (APC), loaded either with the relevant CMV-CTL epitope HLA- A*0201 IE-1$_{316-324}$ (IE1-A2), pp65$_{495-503}$ (pp65-A2) (Wills et al. 1996; Diamond et al. 1997; Khan et al. 2002) or IE2 CMV-peptide library (4 µg/ml) as described above.

ICC was used to measure pp65, IE1 and IE2 IFN-γ$^+$/CD4$^+$ or IFN-γ$^+$/CD8$^+$ T cells from the stimulated splenocytes according to methods previously described (La Rosa et al. 2001; La Rosa et al. 2006; Cobbold et al. 2005; Cosma et al. 2003). 0.5 to 1×10$^6$ events were acquired for each sample on a FACSCanto™ (BD Biosciences, San Jose, Calif.). Analysis was performed using FCS Express version 2 software (De Novo, Ontario, Canada). The number of double-positive cells was expressed as a percentage of the CD8$^+$ T-cell population.

Comparison of mH5 and pSyn Promoter Activity in rMVA Infected Cells. To determine early or total transcriptional activity of mH5 and pSyn promoters in rMVA infected cells, pp65 expression levels were determined in BHK-21 cells that were infected with mH5-pp65-MVA or pSyn-pp65-MVA in the absence or presence of cytosine arabinoside (Ara-C) by quantitative Western blot. BHK-21 cells were seeded at 0.6×10$^6$ per well onto a 6-well plate. The cells were infected with either mH5-pp65-MVA or pSyn-pp65-MVA at MOI=5 in the presence or absence of 40 µg/ml of Ara-C and incubated for 24 hours at 37° C. in a 5% CO2 incubator. The infected cells were harvested at 24 h post-infection and lysed in SDS-PAGE loading buffer (62.5 mM Tris-HCl, pH 6.8, 2.8 mM β-mercaptoethanol, 2% SDS, 10% glycerol, 0.4% Bromophenol Blue). Cell lysates were separated by SDS-PAGE on 10% gels. After electro-transfer of proteins from the gel onto PVDF membranes (Bio-Rad, Hercules, Calif., USA), the blots were incubated with purified mAb 28-103 (Britt et al. 1985) against pp65 and mAb against β-tubulin (Sigma-Aldrich), and then washed and further incubated with HRP-labeled goat anti-mouse Ab according to the manufacturer's instructions. pp65 protein expression was measured by incubating the blots with chemifluorescence substrate solution in ECL Plus detection kit (Amersham, Calif.) for 30 minutes and were scanned using Typhoon™ 9410 workstation and analyzed using ImageQuant TL software (GE Healthcare Bio-Sciences Corp, Piscataway, N.J., USA). β-tubulin was used as internal control for each lane.

Pulse-Chase Metabolic Labeling and Immunoprecipitation. Pulse-chase (PC) and immunoprecipitation (IP) were performed based on modification of described methods (Tobery et al. 1997; Wang et al. 2004b). Briefly, subconfluent cultures of CEF or BHK-21 cells grown in 6-well plates were infected at an MOI of 10 with mH5-pp65-MVA or pSyn-pp65-MVA. At 1 hour postinfection (hpi), cells were washed and incubated with Cys-free and Metfree DMEM (Invitrogen, Carlsbad, Calif., USA) medium containing 5% dialyzed fetal calf serum (FCS; Invitrogen) for 1 hour. Cells were then metabolically labeled (100 µCi/mL/well) for 30 min with a mixture of [$^{35}$S]Cys+[$^{35}$S]Met [Express Protein Labeling Mix™ (1000 Ci/mmol) PerkinElmer, Boston, Mass., USA]. After labeling, the cells were washed twice with PBS and either harvested immediately or chased in RPMI medium with 10% FCS (ISC-BioExpress, Kaysville, Utah, USA) supplemented with excess unlabeled methionine (1 mM) and cysteine (5 mM) up to 10 hours. After each time point, cells were immediately pelleted, then lysed in 1.0 mL PBS containing 1.0% Triton X-100, 1.0% sodium deoxycholate (Sigma, St. Louis, Mo., USA) and 0.1% SDS in the presence of Protease Inhibitor Cocktail (Roche, Nutley, N.J., USA). Supernatants (0.5 mL) were precleared once with 50 µL of protein A/G-agarose beads (Santa Cruz Biotechnology) for 1 h. Sequential incubation with 2.4 µg purified mAb against CMV-pp65 (mAb 28-103; Britt et al. 1987) was followed by an isotope-specific mAb (19C2; Schmeiz et al. 1994) for 2 hours. Immune complexes were captured by incubation for 1 hour with 50 µL of protein A/G beads. The immune complex bound Protein A/G beads were washed 4 times with 0.1% Triton X-100 in PBS and bound proteins were eluted by boiling in 0.2% SDS, 5 mM DTT, 40 mM sodium phosphate buffer (pH 6.5) into SDS-polyacrylamide gel electrophoresis (PAGE) sample buffer. Proteins were separated by 10% SDS-PAGE and detected by autoradiography using X-OMAT film (Kodak, Rochester, N.Y., USA).

Serial Passage of pSyn-pp65-IE1/e4-MVA pp65-IE1/e4-MVA (pSyn) was generated using a pZWIIA transfer plasmid as previously described (Wang et al. 2007). The pp65 and IE1/e4 gene expression cassettes were integrated into the deletion integration site II of the MVA genome (Del II) via homologous recombination as shown in FIG. 1A. pSyn-pp65-IE1/e4-MVA was sequentially passaged for 10 rounds on primary chicken embryo fibroblast (CEF) cells prepared from specific pathogen-free chicken eggs. The virus titer and growth rate of each passage was measured. There was no significant change in virus titer and growth rate during serial passage. Cell lysates of each passage were prepared in parallel from 100 mm culture dishes of cells infected with the same amount of virus established by titration on CEF cells.

Figure 1B:
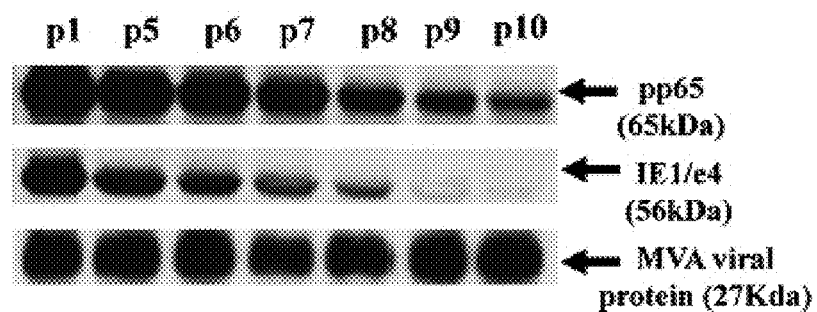
FIG. 1B illustrates Western blot (WB) detection of pp65 and IE1 exon4 expression levels of pSyn-pp65-IE1/e4-MVA after serial passages 1-10. The top panel shows a membrane blotted with mAb28-103 specific for pp65; the middle panel shows a membrane blotted with p63-27 specific for IE1/e4, and the bottom panel shows a membrane blotted with mAB 19C2 that detects VV-BR5.
Figure 1C:
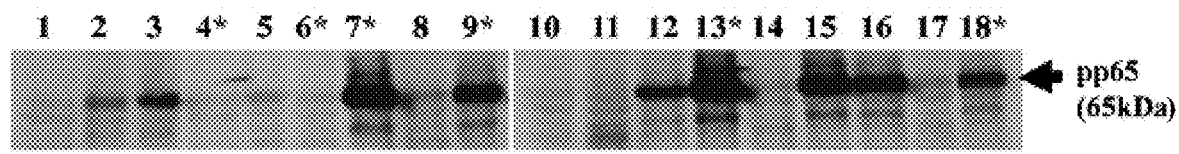
FIG. 1C illustrates Western blot (WB) detection of pp65 expression of 18 pSyn-pp65-IE1/e4-MVA individual isolates. Each lane represents a single individual isolate from passage 10. Samples #4, #6, #7 and #13 marked with a star were selected for viral genomic DNA extraction and Southern blot analysis as described below.

FIG. 1B shows Western blot detection of pp65 and IE1 exon4 expression levels of pp65-IE1/e4-MVA-infected CEF cells (serial passages p1 to p10). pp65 and IE1/exon4 protein levels progressively decreased during passage, and were significantly reduced after ten serial passages. The top panel was blotted with mAb 28-103 specific for pp65 to determine pp65 expression levels; the middle panel was blotted with p63-27 specific for IE1 exon4 to determine IE1 exon4 protein expression levels. The bottom panel of FIG. 1B shows the constitutively expressed MVA protein BR5, which was also proved at each passage from the same lysates using the 19C2 mAb (Schmeiz et al. 1994), The steady state expression level of BR5 was unchanged during the 10 passage evaluation. Serial passage of pSyn-IE1/e4-MVA was also carried out on CEF cells with similar results.

Preparation and Expression Analysis of 18 Individual P10 Isolates

To determine whether gradual decrease of the pp65 and IE1 expression levels during serial passage can be caused by genetic changes that result in non-expressing variants, individual isolates were isolated from passage 10 (P10) by plaque purification. Eighteen wells that appeared to have cyto-pathologic effects (CPE) were collected at 4 days post-infection. Each virus sample was considered to be a single isolate because the equivalent of 0.5 pfu of virus was distributed in each well. Viral infection from these collected samples was confirmed by continuous virus growth and virus titration. Thus, eighteen individual pSyn-pp65-IE1/e4-MVA viruses were isolated from passage 10 by virus plaque purification and expanded in CEF cells to prepare cell lysates for Western blot. See FIG. 1C. As illustrated in FIG. 1C, eight of the 18 (40%) collected individual isolates had lost pp65 expression. In contrast, six of six (100%) individual isolates from P1 all had similar strong levels pp65 expression. Each lane of FIG. 1C contains a single individual isolate from passage 10. Samples #4, #6, #7 and #13 (marked with a star in the figure) were selected for further analysis as described below.

Deletion of the pp65 and IE1/e4 Gene was the Cause of Loss of pp65 and IE1/e4 Protein Expression from Individual Virus Isolates of pSyn-pp65-IE1/e4-MVA.

To determine whether mutations or total deletion of the pp65 and IE1 genes during serial passage were responsible for this loss of protein expression, two of the isolates described above with full expression levels, two isolates that lost pp65 protein expression (#4, #6 in FIG. 1C) and two isolates that retained pp65 expression from P10 (#7, #13 in FIG. 1C) were selected. Western blot was performed on these isolates to detect both pp65 and IE1 protein expression levels, and Southern blot was used to detect pp65 and IE1 expression cassettes from viral DNA.

A monoclonal antibody specific for an MVA viral protein (BR5) was included in the Western blot to detect endogenous viral gene expression to control for virus input in all six samples. See FIG. 2A, panel (iii). The two individual isolates from passage 10 that maintained pp65 expression also expressed IE1 at similar level as P1. (FIG. 2A, panel (i)) In contrast, the two isolates from P10 that lost pp65 expression also coordinately lost IE1 protein expression (FIG. 2A, panel (ii)). All four cases showed either coordinate expression of both antigens or their absence, suggesting that the whole cassette was either maintained or inactivated by deletion or mutation when protein expression was not detected. In contrast, the expression of the MVA BR5 protein remained uniformly unchanged (FIG. 2A, panel (iii)).

A Southern blot detected the pp65 and IE1 genes and established the relationship of protein expression levels and the presence of the genes. Equal amounts of DNA from each viral isolate was digested with Pme I and Not I restriction enzymes to excise pp65 and IE1/e4 gene expression cassettes (3.9 Kb), which were detected by a $^{32}$P-radiolabled DNA probe. The gene expression cassette was detected in two individual virus isolates from P1 and P10 (lanes 1, 2, 5, 6 in FIG. 2B), but not detected in two viral isolates from P10 that also lost protein expression (Lane 3 and 4 in FIG. 2B). The del II site of MVA was further analyzed by DNA restriction endonuclease analysis of MVA genomic DNA and by PCR using a series of primers that target the surrounding del II region. CMV-pp65 and IE1 gene expression cassettes together with the surrounding MVA del II region were found to be absent. The possibility that the two non-expressing mutants were contaminant wild type MVA virus that was introduced and amplified during the serial passage was excluded using additional qPCR primers. Expression of pp65 and IE protein was correlated with the presence of the corresponding genes, suggesting that large deletions rather than small ones resulted in their absence.

Figure 2A:
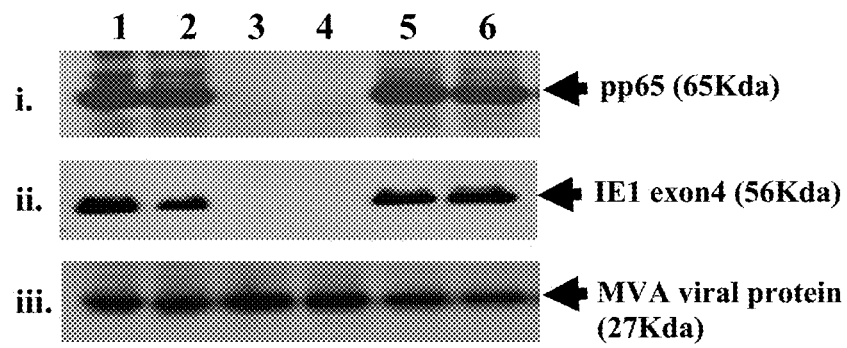
FIG. 2A is a series of Western blots detecting pp65 and IE1 exon4 protein expression of selected individual isolates of pSyn-pp65-IE1 exon4-MVA.
Figure 2B:
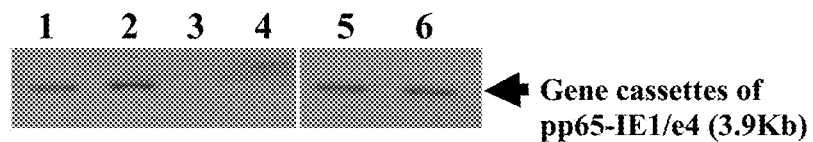
FIG. 2B is a Southern blot detecting pp65 and IE1 exon4 gene insertion of selected individual isolates of pSyn-pp65-IE1/e4-MVA. MVA viral genomic DNA was digested with restriction enzymes to excise 3.9 Kb fragments of pp65-IE1 gene expression cassettes, separated by 1% agarose gel and transferred to nylon membrane filter. This filter was hybridized with the $^{32}$P-radiolabled DNA probe specific for both pp65 and IE1 exon4 gene and exposed to x-ray film. Lanes 1 and 2 in FIGS. 2A and 2B are two individual isolates selected randomly from passage 1 of pSyn-pp65-IE1/e4-MVA. Lanes 3 and 4 of FIGS. 2A and 2B are the two individually isolates of #4 and #6 marked with * from FIG. 1C with no expression of pp65 and IE1 exon4. Lanes 5 and 6 of FIGS. 2A and 2B are the two individual isolates #7 and #13 marked with * in FIG. 1C with pp65 and IE1 exon4 protein expression levels.

Two isolates from P10 maintained pp65 and IE expression levels as P1 (FIG. 2A, lanes 1 and 2). These isolates were tested to determine whether they represented stable forms of pSyn-pp65-IE1/e4-MVA and could maintain stable expression of both insert genes during serial passage. These two isolates were sequentially passaged for an additional 10 rounds on CEF cells. Both pp65 and IE1 protein expression still decreased to a low level at the conclusion of additional serial passage. These results demonstrate that high-expressing isolates from P10 are not stabilized forms of pSyn-pp65-IE1 exon4-MVA, and are subject to deletion during passage.

Immunogenicity of pSyn-pp65-IE1/e4-MVA is Reduced after Serial Passage.

To determine if reduction of pp65 and IE1 protein expression impacted immunogenicity, P1 and P10 virus stocks were expanded for mouse immunizations. HHD II mice (Tg HLA A2.1) were used at 6 to 12 weeks for immunization and were bred and maintained under SPF conditions in a centralized animal care facility. Human peripheral blood mononuclear cells (PBMC) were collected, purified using Ficoll™ and cryopreserved at −80° C. HHD II mice were separately immunized with both P1 and P10 passage strains for 3 weeks.

Figure 3:
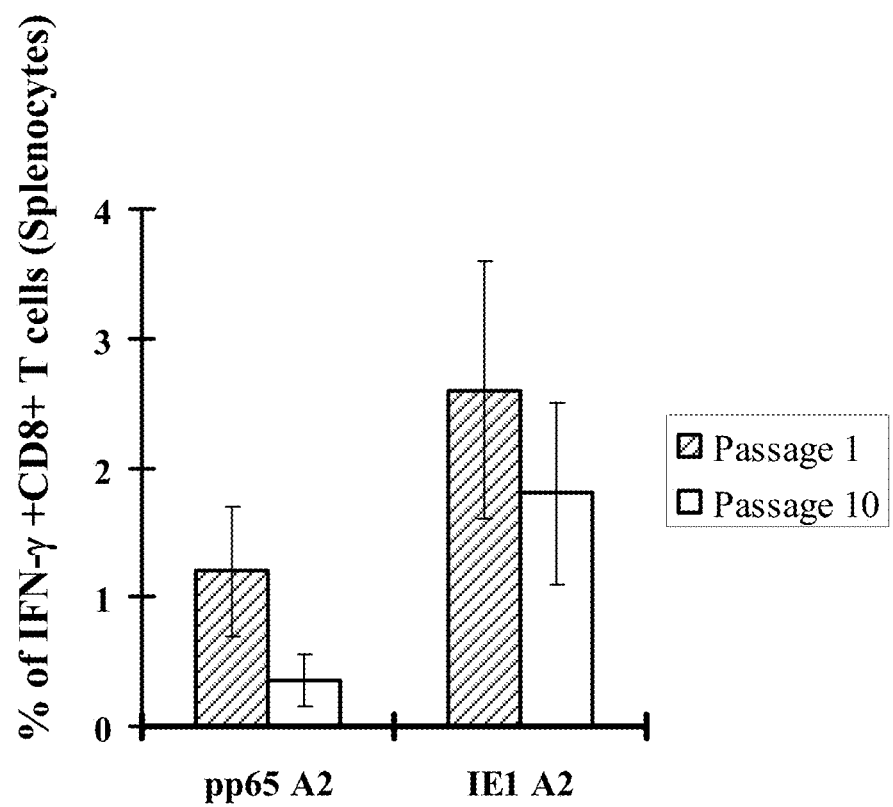
FIG. 3 is a bar graph showing the immunogenicity of pSyn-pp65-IE1/e4-MVA passage 1 and passage 10 immunized HHD II mice (HLA A2.1). Average levels of IFN-γ producing specific for the CMV pp65- or IE1-A2 epitope (x axis) for all immunized mice is shown in Y-axis. IFN-γ producing CD8$^+$ T-cells to mock during the ICS procedure were subtracted. Error bars represent the SEM for all immunized mice.

Splenocyte immune response was assessed by ICC to detect IFN-γ expression. Immunodominant HLA A2-restricted pp65 and IE1 CTL epitopes were used to evaluate the HLA A2-restricted CD8+ T cell response. See FIG. 3. The results show a statistically significant diminution of pp65 and IE1 specific-INF-γ producing CD8 positive T cells between P1 and P10 immunized groups.

Genetic Stability of pSyn-pp65-IE1/e4-MVA Measured by qPCR

Since progressive loss of pp65 and IE1 protein expression is correlated with the deletion of gene expression cassettes, the kinetics of the loss of the genes was measured to develop a potential mechanism. The genetic stability of rMVA can be assessed by computing the ratio of the gene insert and the MVA backbone copy number.

The ratio of gene insert to MVA backbone at initial passage was normalized to unity, and a gradual reduction during serial passage. Only 20% of the rMVA retained pp65 and IE1 exon4 gene inserts after round P10. See FIG. 4A. This measurement establishes a correlation between the disappearance of foreign protein antigen genes that is confirmed by qPCR, lower protein expression levels and reduced immunogenicity of the passaged viral population.

Genetic Stability of pSyn-pp65-IEfusion-MVA Measured by qPCR

Figure 4A:
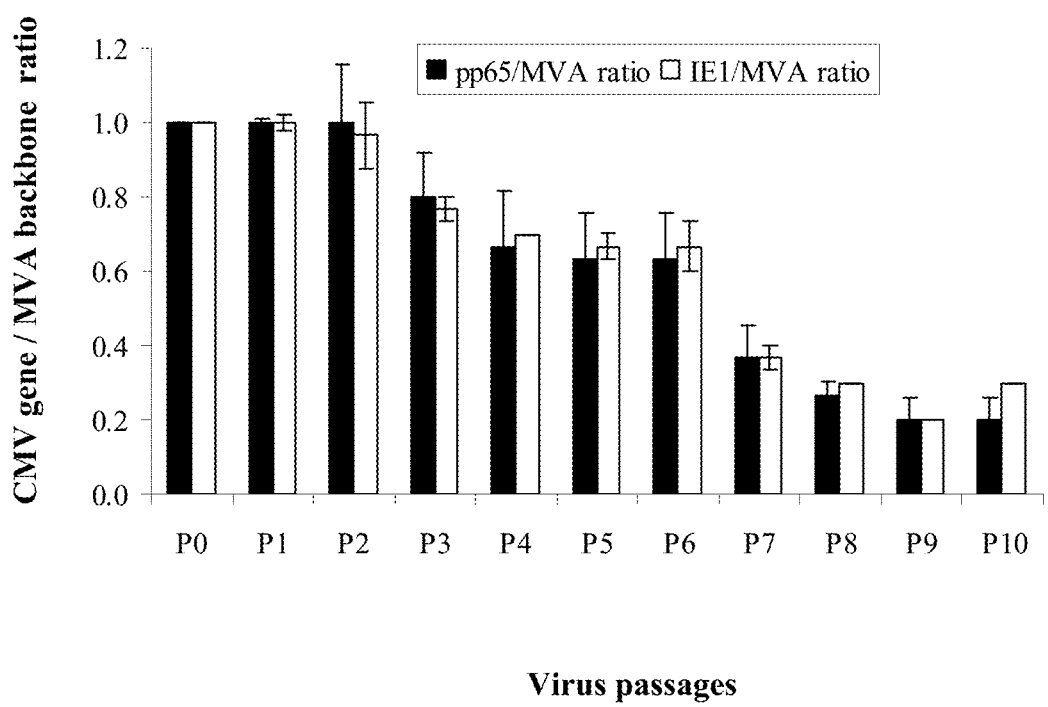
FIG. 4A is a bar graph showing data related to the genetic stability of pSyn-pp65-IE1/e4-MVA at serial passages P0-P10 as determined by qPCR. pSyn-pp65-IE1/e4-MVA genomic DNA was extracted as described in Example 8. pSC11 plasmid containing CMV genes (pp65, IE1/e4 and IE2/e5) was used to prepare absolute standards. The qPCRs were performed using primers specific for pp65, IE1 exon4 and TK gene. The copy numbers for pp65 gene, IE1 gene and MVA backbone copies were calculated using ABI software (SDS3.2) and the genetic stability of the mH5-pp65-IEfusion-MVA was determined by computing the ratio of the pp65 gene insert and the MVA backbone or the ratio of the IE1 exon4 gene insert and the MVA backbone as indicated in Y-axis. The ratio at passage 1 was normalized to 1 and each consecutive passage was normalized based on passage 1. The qPCR for each DNA sample were performed three times independently in duplicate. The average ratio and error bar shown in the figure represent three independent determinants.
Figure 4B:
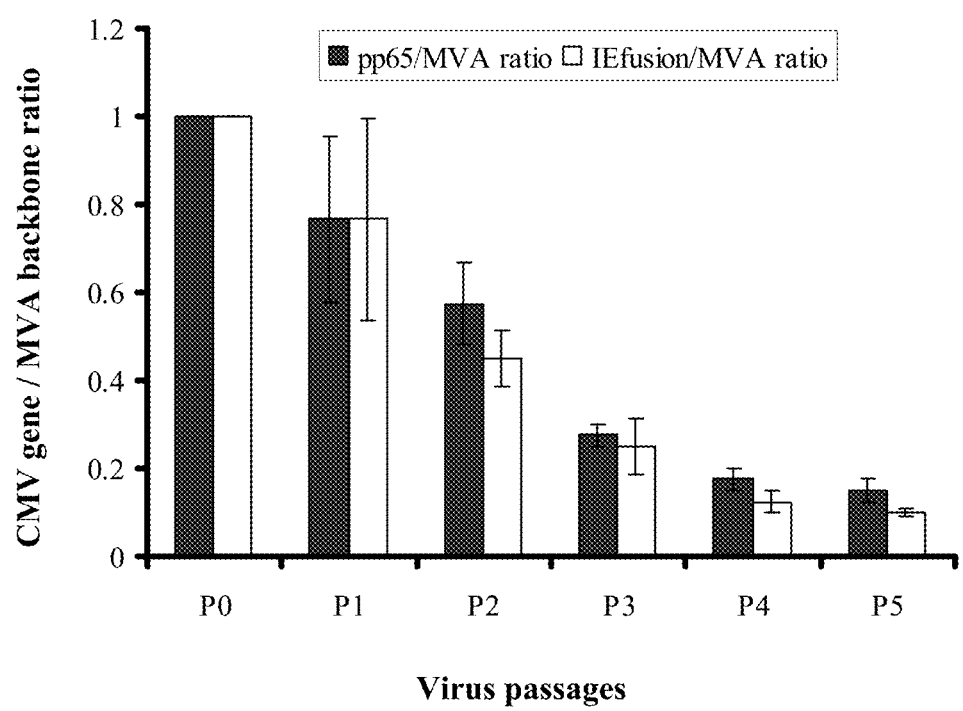
FIG. 4B is a bar graph showing data related to the genetic stability of pSyn-pp65-IEfusion-MVA at serial passages P0-P5 as determined by qPCR. The copy numbers for pp65 gene, IEfusion gene and MVA backbone were analyzed using ABI software (SDS3.2) and the genetic stability of the mH5-pp65-IEfusion-MVA was determined by computing the ratio of the pp65 gene insert and the MVA backbone or the ratio of the IEfusion gene insert and the MVA backbone. The ratios at passage 1 for pp65 and IE1 exon4 gene were normalized to 1. The qPCR for each DNA sample were performed for three times independently in duplicates and average ratio and error bar shown in FIG. 4B represent three independent determinants.

Recombinant MVA expressing three CMV antigens under control of pSyn promoters (pSyn-pp65-IEfusion-MVA) were constructed to expand the representation of early genes and epitope according to methods as described in Example 1. pSyn-pp65-IEfusion-MVA includes the IE2-exon5 gene which is fused to IE1-exon4. pSyn-pp65-IEfusion-MVA viral genomic DNA was extracted and qPCR was performed using pp65, IEfusion and TK specific primers as described herein.

pSyn-pp65-IEfusion-MVA was serially passaged five times. Even after a single passage, however, evidence of instability was observed (FIG. 4B). Only 10% of the original levels of pp65 and IEfusion insert sequences were detected by qPCR after 5 passages, which demonstrates an unexpected decrease in stability, possibly because of the gene fusion. See FIG. 4B. This result highlights that different combination of genes (pp65 and IE1/e4 and pp65 and IEfusion) result in pronounced genetic instability using the pSyn promoter, suggesting that the genes themselves are not the main contributor to genetic instability compared to the activity of the pSyn promoter.

Construction of mH5-pp65-MVA and Measurement of Genetic Stability

Figure 5B:
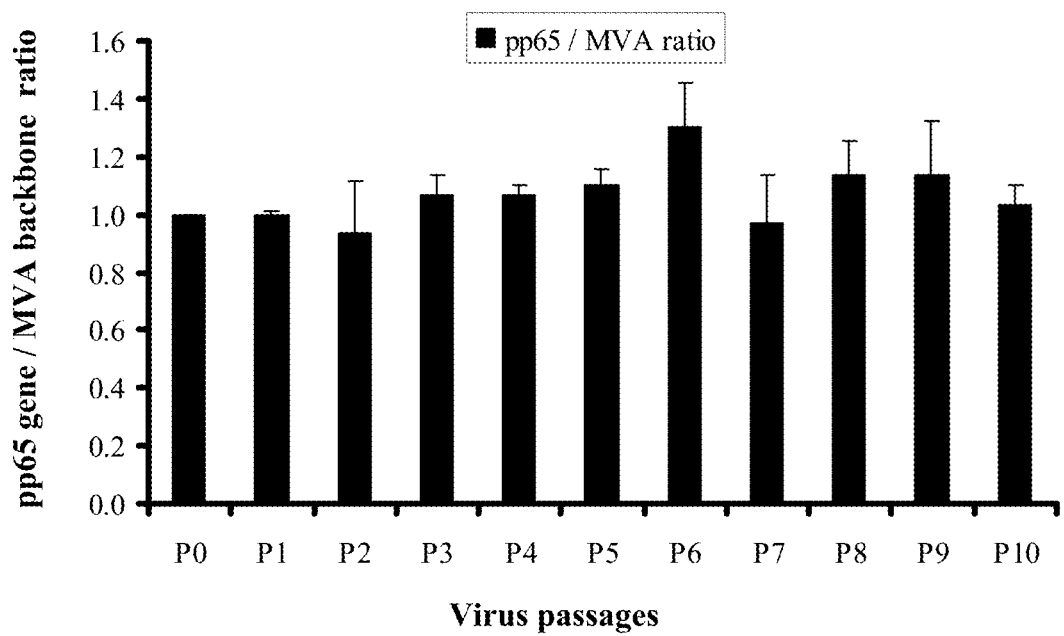
FIG. 5B is a bar graph showing quantitative PCR results relating to the genetic stability of 10 serial passages of mH5-pp65-MVA. Recombinant MVA was generated using shuttle plasmids that had the mH5 promoter directing the transcription of pp65. mH5-pp65-MVA viral genomic DNA was extracted and qPCR was performed using pp65, and TK specific primers as described above. The copy numbers for pp65 gene and MVA backbone were analyzed using ABI software (SDS3.2) and the genetic stability of the mH5-pp65-IEfusion-MVA was determined by computing the ratio of the pp65 gene insert and the MVA backbone. The ratios at passage 1 were normalized to 1. The qPCR for each DNA sample were performed three times independently in duplicate. The average ratio and error bars represent three independent determinants. No significant changes were seen in the ratio of CMV gene:MVA backbone genomic copy number during serial passage. The results of immunogenicity measurements in the HHD II (HLA A2.1) mouse were superior to that observed with similar viruses employing the pSyn promoter.

Although the pSyn promoter was optimized for high level protein expression and was designed to be highly active by combining several early and late promoter elements, it is dominated by its late stage promoter activity (Chakrtabarti et al. 1997). Therefore the instability of pSyn-pp65-IE1/e4-MVA and pSyn-pp65-IEfusion-MVA may be due to the properties of pSyn promoters. To improve genetic stability, the pSyn promoter was replaced with the mH5 promoter which stimulates a greater proportion of its transcriptional activity at an earlier stage of the virus life cycle (FIG. 5A) (Wyatt et al. 1996; Earl et al. 2009). rMVA was generated using shuttle plasmids that had the mH5 promoter directing the transcription of the CMV-pp65 gene. Quantification by qPCR revealed no significant changes in the ratio of CMV insert gene/MVA backbone genomic copy number during 10 serial passages of a virus using the mH5 promoter directing recombinant protein expression (FIG. 5B).

Figure 5C:
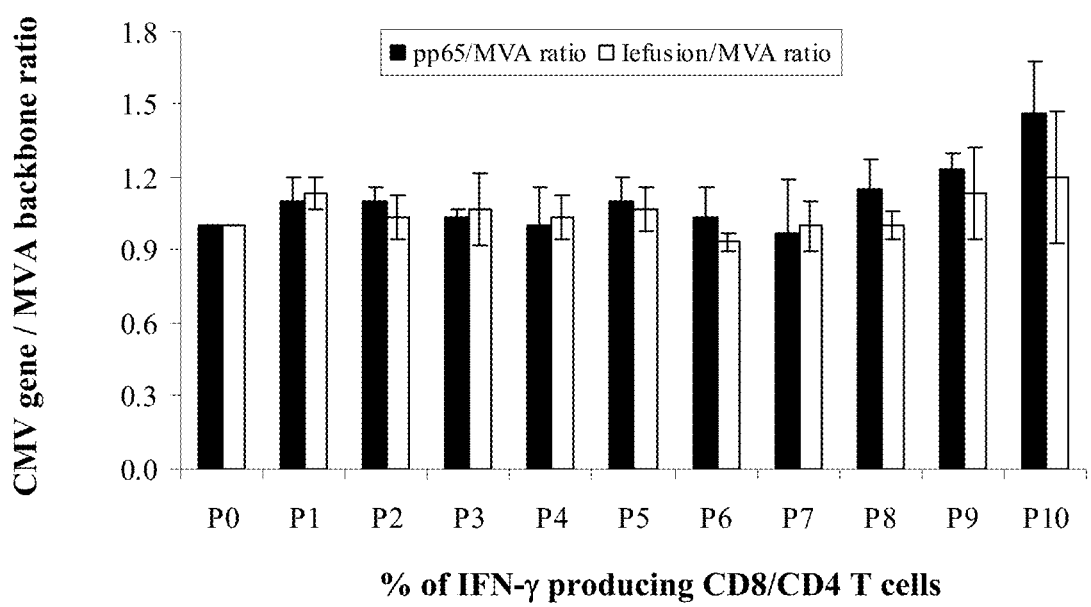
FIG. 5C is a bar graph showing quantitative PCR results relating to the genetic stability of 10 serial passages of mH5-pp65-IEfusion-MVA. mH5-pp65-IEfusion-MVA genomic DNA was extracted and qPCR was performed using pp65, IEfusion and TK specific primers as described in the Examples below. The copy numbers for pp65 gene, IEfusion gene and MVA backbone were analyzed using ABI software (SDS3.2) and the genetic stability of the mH5-pp65-IEfusion-MVA was determined by computing the ratio of the pp65 gene insert and the MVA backbone or the ratio of the IEfusion gene insert and the MVA backbone. The ratios at passage 1 for pp65 and IE1/e4 gene were normalized to 1.
Figure 5D:
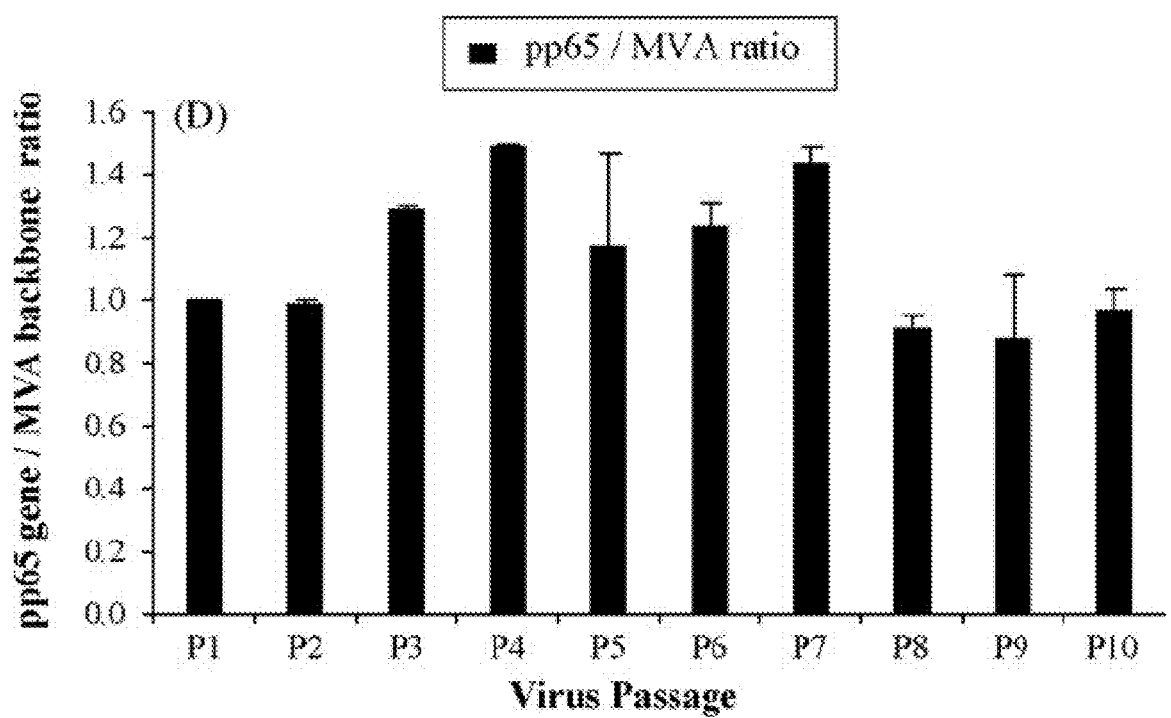
FIG. 5D is a bar graph, similar to FIG. 5C, except the 10 serial passages were conducted on CEF and results shown are computed using pp65 and TK-specific primers. The qPCR for each DNA sample were performed for three times independently in duplicates and the ratios and error bars shown in the figure represent an average of three independent determinants.

Genetic Stability of rMVA Expressing CMV-pp65 and IEfusion Under mH5 Promoter Control A single rMVA simultaneously expressing both CMV-pp65 and IEfusion proteins was constructed using dual mH5 promoters using two strategies. First, an MVA expressing all three foreign protein antigens was constructed by targeting a single integration site (del II) with a plasmid shuttle vector that had tandem mH5 promoters in opposing orientation. It could not be stably prepared, likely due to intramolecular homologous recombination, that is presumably initiated by the identical mH5 promoter copies. Second, the CMV-pp65 and IEfusion genes were inserted at two separate sites in MVA (del II located at 149,261 and del III located at 20,625 of the MVA genome) to prevent the deletional recombination mediated by the two identical copies of the mH5 promoter. A schematic picture of the structure of this rMVA and the insertion sites is provided in FIG. 5A. This virus was successfully constructed, and passaged 10 times in a similar manner as was done for the pSyn viruses above (FIGS. 4A and 4B). The passages were conducted on both BHK-21 (FIG. 5C) and CEF (FIG. 5D) cells. Genetic stability was evaluated by qPCR using three primer pairs specific for the CMV-pp65 and IEfusion genes, and the MVA viral genomic backbone, respectively. The qPCR results for both CMV antigens are computed as a ratio to the viral genomic MVA backbone (FIG. 5C). Both CMV gene inserts at del II and III integration sites had excellent stability, with almost 100% of each gene copy number maintained after 10 passages compared to P0 (FIG. 5C). A similar result was found with virus passaged on CEF, using the CMV-pp65 and the MVA backbone sequences as targets for qPCR (FIG. 5D).

Target sequences measured by qPCR represent a small region (0.2-0.3 bps) of CMV-pp65 (1.7 kb) and IEfusion gene (2.9 kb) insertion. To exclude the possibility that the qPCR results may not represent focused regions of instability throughout the entire length of both genes, several additional pairs of primers targeting different regions of CMV-pp65 and IEfusion gene were designed. The ratio of CMV-pp65 or IE1 or IEfusion compared to the MVA genomic DNA backbone was similar throughout the length of each insert gene.

Minimal Change in Immunogenicity of mH5-pp65-IEfusion-MVA after Serial Passage

Figure 6A:
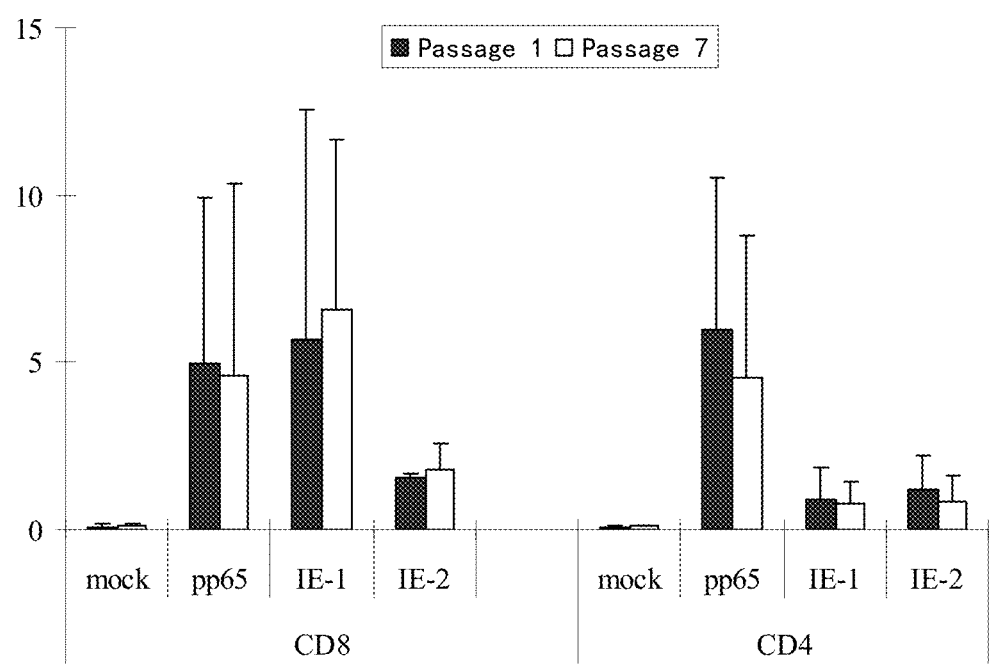
FIG. 6A is a bar graph showing the immunogenicity of mH5-pp65-IEfusion-MVA of passage 1 and 7 using human peripheral blood mononuclear cells (PBMC). PBMCs from healthy donors who were ex vivo positive responders to CMV antigens (Wang et al. 2008) were incubated with antigen presenting cells infected with either passage 1 or passage 7 of mH5-pp65-IEfusion-MVA for 7 days followed by overnight incubation with diluent (mock), pp65, IE1 or IE2 peptide libraries in the presence of brefeldin A. Cells were then harvested and stained with anti-human CD8 or CD4, permeabilized and stained with anti-human IFN-γ antibodies and evaluated by flow cytometry. Average percentages of IFN-γ producing CD8 or CD4 T cells are shown (N=4). Error bars represent standard deviation.
Figure 6B:
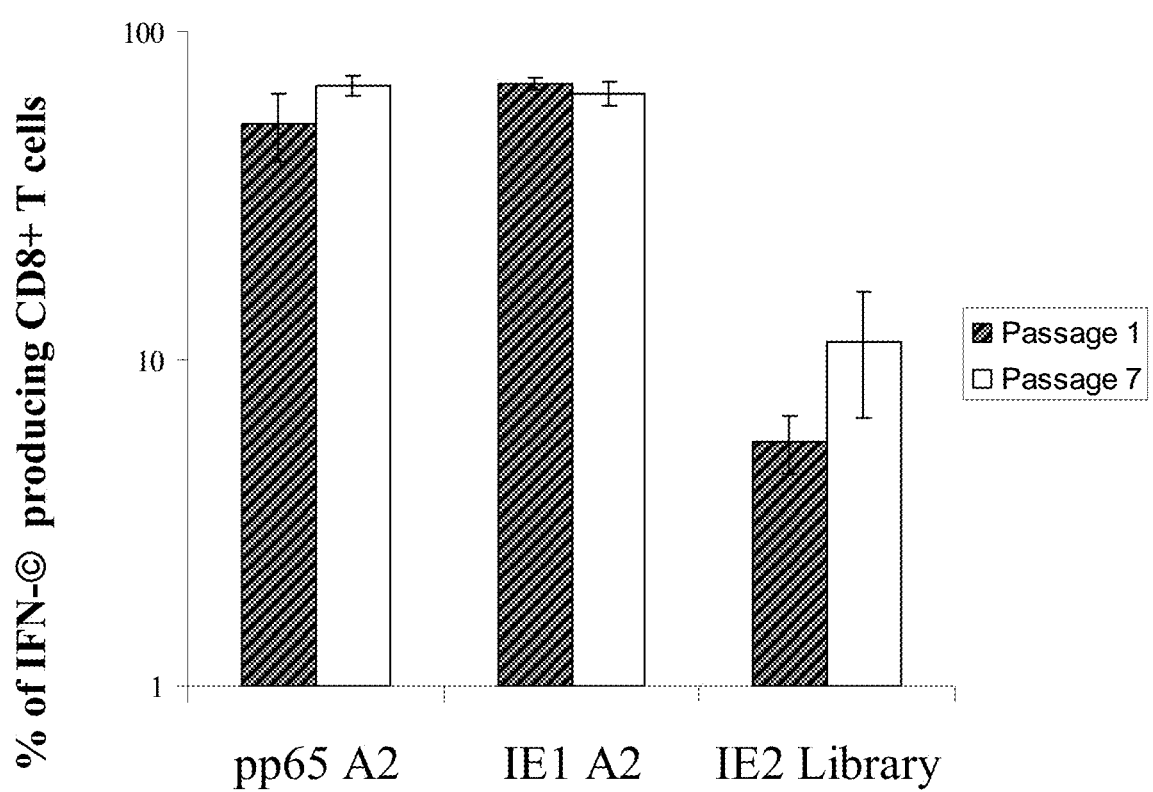
FIG. 6B is a bar graph showing the immunogenicity of mH5-pp65-IEfusion-MVA of passage 1 and 7 in HHD II mice (HLA A2.1) Splenocytes from HHD II mice immunized with pSyn-pp65-IE1 exon4-MVA from passage 1 (P1) or passage 7 (p7) were subjected to in vitro stimulation (IVS) separately with either pp65 A2 or IE1A2 peptides or IE2 peptide library-loaded HLA-A*0201 EBV-lymphoblastoid cells (LCL) derived from a healthy CMV positive volunteer (La Rosa et al. 2001) for 8 days. After IVS, the splenocytes were incubated with mock A2, pp65A2, IEA2 peptides or IE2 peptide library overnight and harvested for ICC as described in the examples below. Average levels of CD8+ T-cell IFN-γ production specific for the CMV pp65A2, IE1A2 epitopes or IE2 peptide library shown (x-axis) for all immunized mice. IFN-γ production to mock stimulated cells during the ICS procedure was subtracted. Error bars represent the SEM for all immunized mice.

To determine if genetic stability of mH5-pp65-IEfusion-MVA after 10 multiple passages translated to equivalent immunogenicity at passage P1 and P7, the capacity of both the P1 and P7 passage viral stocks to support vigorous amplification of a memory T cell response after exposure of human PBMC to MVA vaccines was assessed (Wang et al. 2004b). Both P7 and P1 passages (p=NS by Student t-test) (FIG. 6A) showed equivalent immunogenicity. The qualitative differences between T cell subsets stimulated by individual foreign protein antigens were not altered after 7 passages in peripheral blood mononuclear cells (PBMC) from four healthy volunteers. There also was no significant difference (p>0.5, paired t test) in the response of HHD II mice immunized with the mH5-pp65-IEfusion MVA virus stocks at passages P1 and P7 similar in design to experiments described above and shown in FIG. 3. Very high levels of CMV pp65-specific, IE1-specific and IE2-specific IFN-γ $^+$CD8$^+$ T cells were found, confirming the equivalence of P1 and P7 viral passages states at eliciting high-level immunogenicity in all immunized mice. See FIG. 6B.

Early Expression of CMV-pp65 is Stronger Under Control of mH5 Promoter than pSyn Promoter while Late Expression Levels are Similar Ara-C (cytosine β-D-arabinofuranoside) is a deoxycytidine analog which incorporates into DNA and inhibits DNA replication by forming cleavage complexes with topoisomerase I resulting in DNA fragmentation [Azuma et al. 2001]. It is a selective inhibitor of DNA synthesis that does not affect RNA synthesis in mammalian cells [Dawson et al. 1986] and so can be used to distinguish early and late protein expression in cells and the timing of transcriptional activation of the mH5 and pSyn promoters. Cell lysates prepared from rMVA infected cells in the absence of Ara-C contained both early and late pp65 protein expression, however, cell lysates prepared from rMVA infected cells in the presence of Ara-C contain only early expression of pp65 protein because DNA replication and late gene expression were blocked by Ara-C.

Quantitative WB employing β-tubulin was used as an internal standard to compare CMV-pp65 expression levels in lysates from cells infected with either mH5-pp65-MVA or with pSyn-pp65-MVA in the absence or presence of Ara-C. In the absence of Ara-C, similar CMV-pp65 protein expression levels were observed in both mH5-pp65-MVA-infected and in pSyn-pp65-MVA-infected cells. However, in the presence of Ara-C, there was a 7-fold higher level of CMV-pp65 expression in cells infected with mH5-pp65-MVA as compared to cells infected with pSyn-pp65-MVA (Table 2). As shown in Table 2 below, early pp65 expression in mH5-pp65-MVA (+Ara-C) accounted for 40% of total pp65 expression (−Ara-C) while early pp65 expression in pSyn-pp65-MVA (−Ara-C) accounted only for 6% of total pp65 expression (−Ara-C).

TABLE 2

Early and late activities of mH5 and pSyn promoters as measured by quantitative Western blot.

| Promoter | Insert gene | pp65 expression | | pp65 expression ratio |
| --- | --- | --- | --- | --- |
| | | +Ara-C | −Ara-C | (−Ara-C/+Ara-C) |
| mH5 | pp65 | 0.9 | 2.25 | (2.25/0.90) |
| pSyn | pp65 | 0.13 | 2.23 | (2.23/0.13) |

Pulse-Chase Analysis Reveals Equal Protein Stability of CMV-pp65 Antigen Under the Control of Either pSyn or mH5 Promoters.

Figure 16:
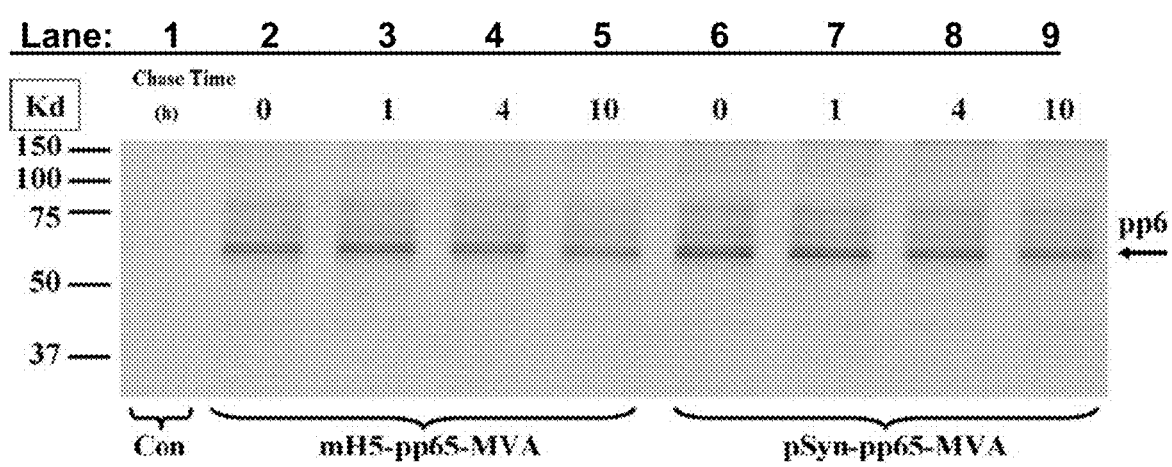
FIG. 16 is a gel illustrating metabolic radio-labeling of CMV-pp65 detected by immunoprecipitation after viral infection of CEF cells. mH5-pp65-MVA (lanes 2-5) and pSyn-pp65-MVA (lanes 6-9) viruses were used to infect primary CEF plated on 60 mm TC dishes at an MOI of 10 for 1 hour, followed by depletion of intracellular stores of Met+Cys for 1 h, and labeled with 35S [Met+Cys] for an additional 30 minutes. Excess unlabeled Met+Cys was diluted into fresh medium, and further incubation times are indicated in hours (0, 1, 4 and 10) above the gel profile. At the conclusion of the "chase" period, cell lysates were made and immunoprecipitation was conducted as described in the Examples below. The CMV-pp65 antigen detected by the mAb 28-103 is indicated by an arrow to the right and adjacent to the gel profile. The 1st lane at the far left (Con) represents a control CEF culture that was radio-labeled after infection with a gus-MVA virus which expresses the α-glucoronidase bacterial marker without CMV-pp65 (Wang et al. 2007).
Figure 17:
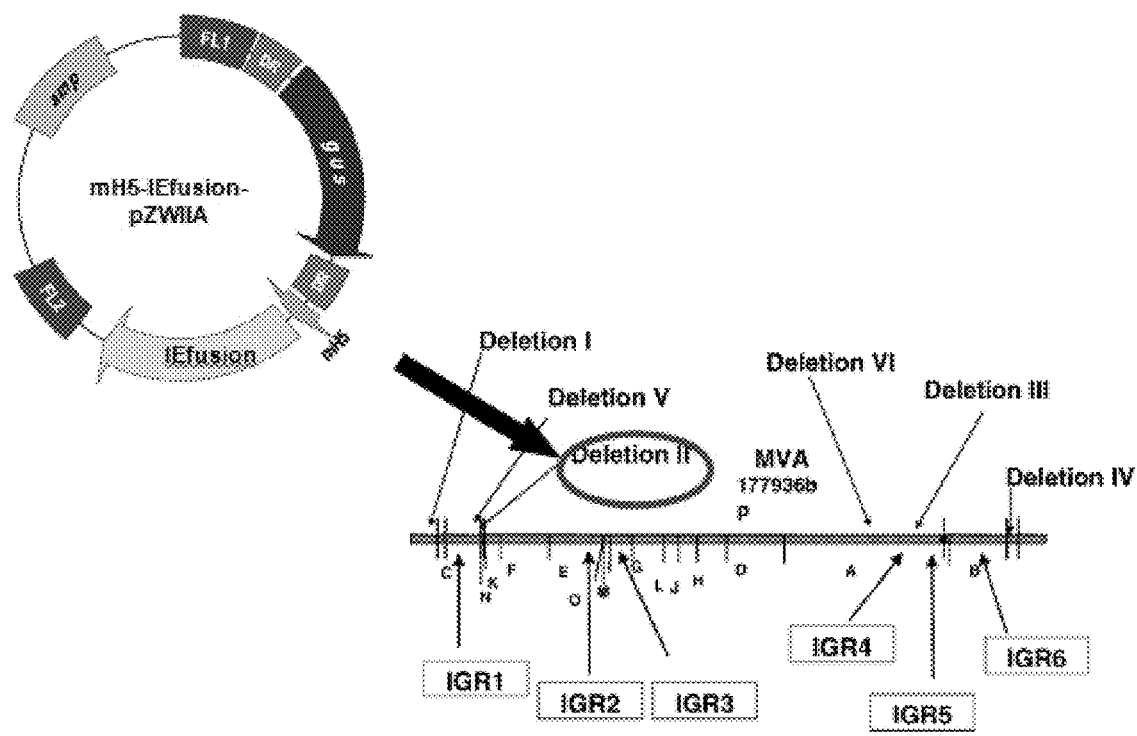
FIG. 17 is a scheme of the MVA genome showing deletions and intergenic regions (IGRs). The MVA deletion II insertion site (del II) for the mH5-IEfurion-pZWIIA (GUS) shuttle plasmid is shown by the arrow. The shuttle plasmid has insertion sites for foreign genes (IEFusion) controlled by an mH5 promoter, a marker gene (gus), homologous flanking sequences for recombination (FL1, FL2), ampicillin resistance (amp) and direct repeats for marker gene removal (DR).
Figure 18:
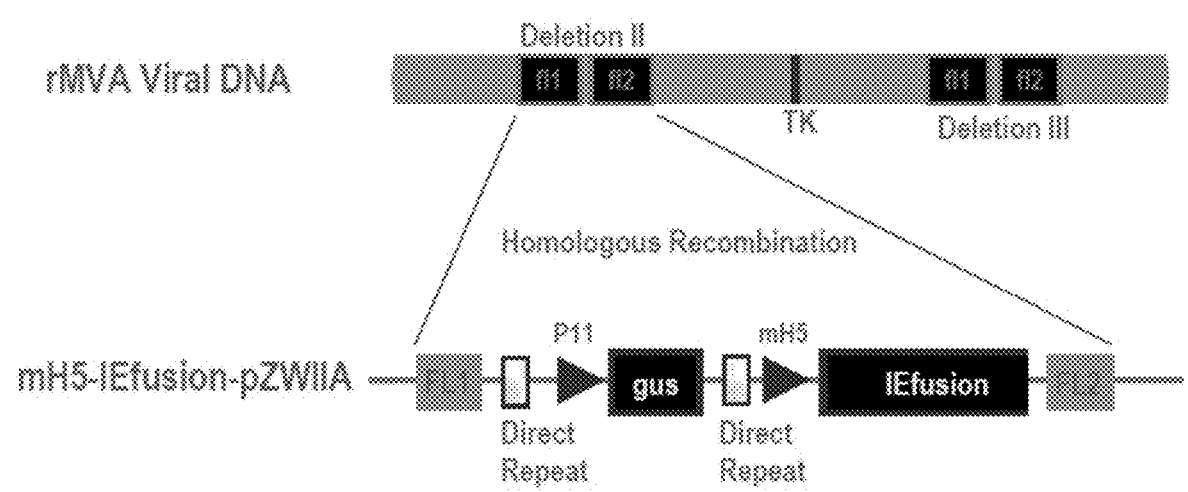
FIG. 18 is a schematic representation of the Deletion II (del II) insertion site on the rMVA Viral DNA for mH5-IEfusion-pZWIIA (GUS).

Alternative explanations for the difference in stability of MVA viruses that utilize the pSyn or mH5 promoter originally demonstrated by a reduction of specific signal from the CMV-pp65 and IE1/e4 protein bands (FIGS. 1 and 2) were explored. To determine whether the reduction in expression can be explained by differential protein stability when the pSyn promoter is used, rather than timing of expression, a pulse-chase approach was used. In this approach, MVA-infected CEF (FIG. 16) and BHK-21 cells (data not shown) were metabolically radio-labeled, followed by cold chase to measure the disappearance of radio-labeled CMV-pp65 protein, which is a measure of its stability to degradation.

The pulse-chase approach used in these studies was similar to previous approaches (Wang et al. 2004b). Three time points of cold chase through 10 hours were utilized, as this time frame is sufficient to measure differences in protein stability based on prior work with CMV-pp65. The infection conditions of CEF and BHK-21 cells were similar as those used for the analysis of protein expression in FIGS. 1 and 2.

Figure 7A:
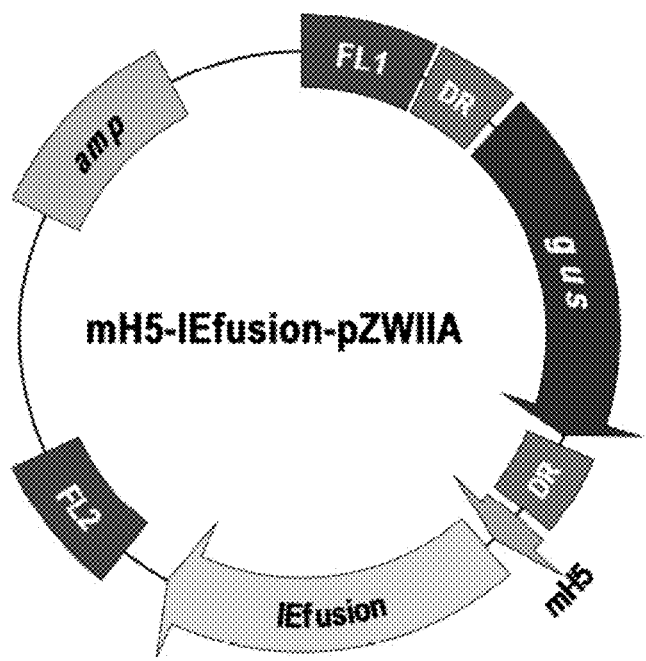
FIG. 7A is a plasmid map of mH5-pp65-pLW51(GUS) plasmid (SEQ ID NO:9).
Figure 7B:
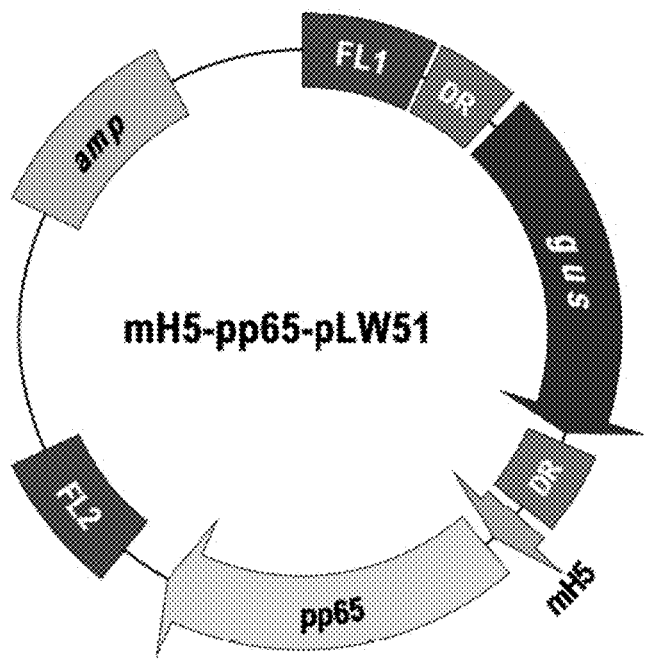
FIG. 7B is a plasmid map of mH5-IEfusion-pZWIIA (GUS) plasmid (SEQ ID NO:10).

The change in labeled CMV-pp65 is limited over the first 4 hours of chase, with only a minimal decline at the 10 hour time point for both promoter constructs (FIG. 7). The pattern of CMV-pp65 expression and stability is equivalent when either the mH5 or pSyn constructs were evaluated. The specificity of the recognition of radiolabeled CMV-pp65 is shown by the absence of an equivalent CMV-pp65-specific radiolabeled band in the gus-MVA infected control lane. Similar to previous studies, two closely juxtaposed bands are found after immunoprecipitation (IP) with mAb 28-103. Based on the differences between the CMV-pp65 decay profile and the non-specific band, the lower band is likely to reflect the target pp65 protein. Moreover, examining the same extracts using an isotype control mAb shows absolute specificity for the pp65 protein (data not shown). Therefore, the choice of promoter does not dramatically influence the degradation rate of the CMV-pp65 antigen. Consequently, protein stability is likely not a factor in determining the stability characteristics of both MVA expressing CMV-pp65.

Example 3

Figure 19:
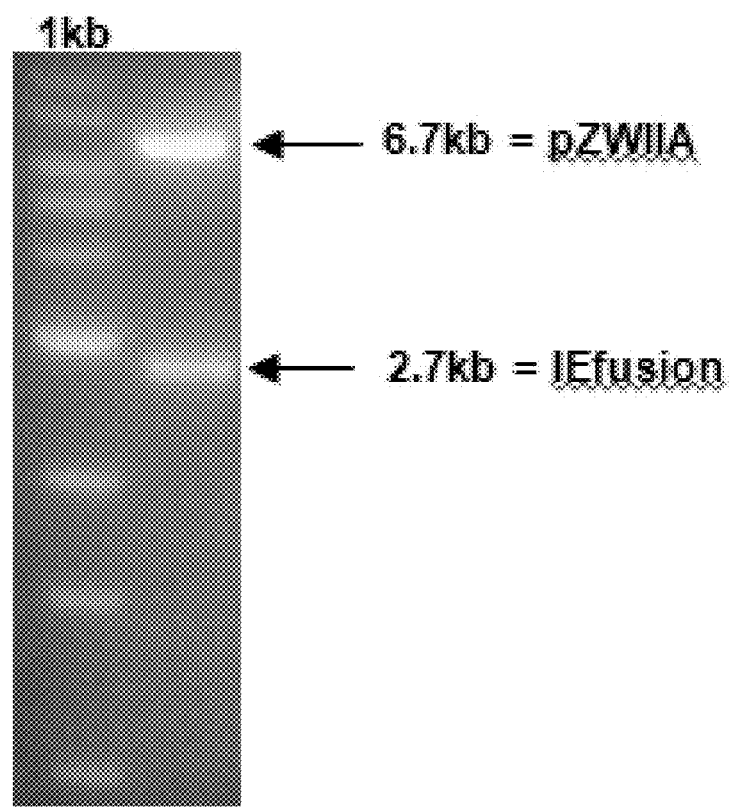
FIG. 19 is a Western blot verifying IEfusion incorporation by restriction enzyme digestion (Asc I and Pme I) followed by DNA sequence analysis.
Figure 20:
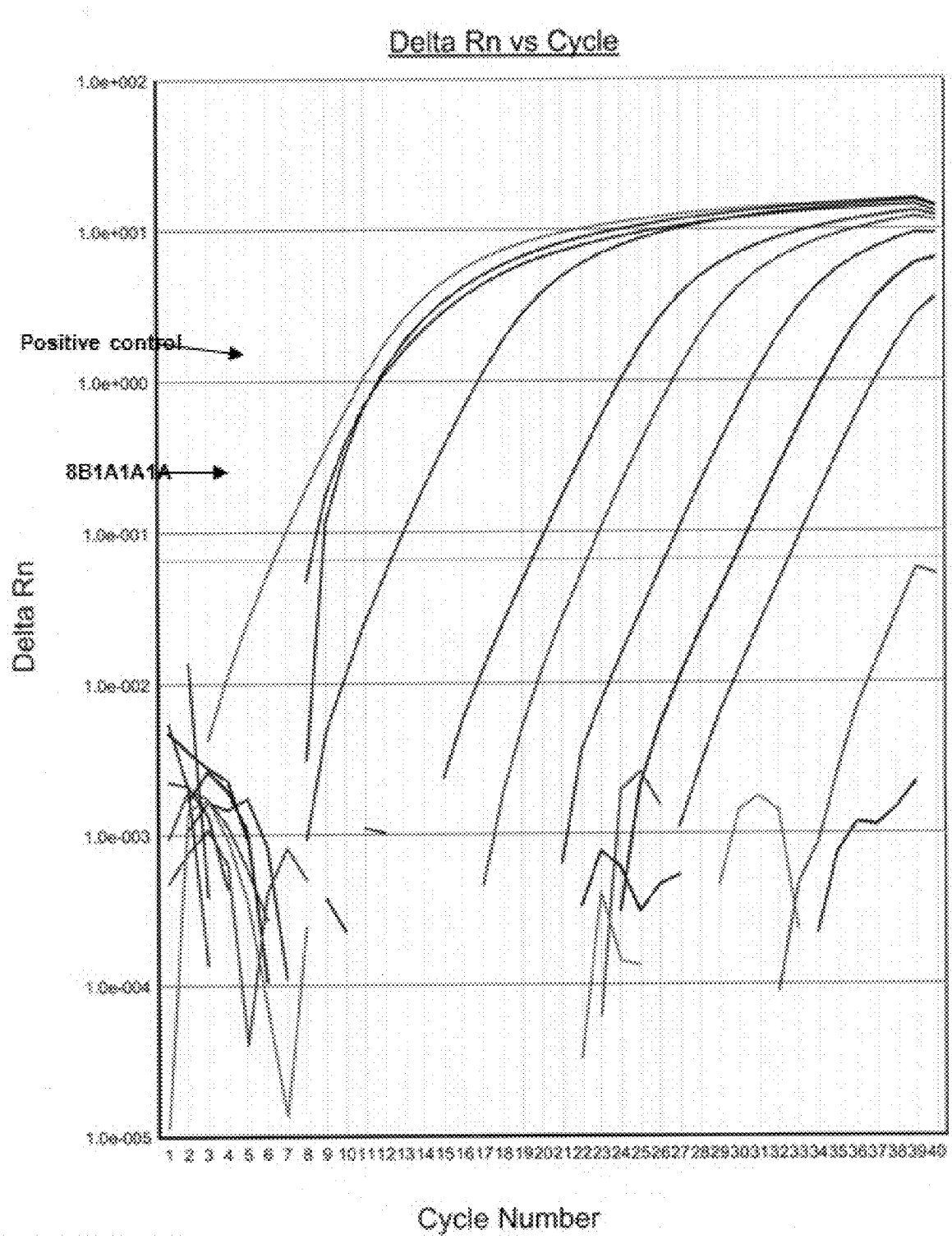
FIG. 20 is a qPCR amplification plot for IEfusion. The standard curve was established with $10^2$-$10^7$ copies of IEfusion. The cycle number is plotted versus the Delta Rn (normalized reporter signal). Delta Rn represents the Rn munus the baseline signal established in early PCR cycles. Copy number of R10 isolate sample No. 8B1A1A1A was determined to be $9 \times 10^7$, which was comparable to the positive control.

Generation and Expansion of pp65-IEfusion-MVA (CMV-MVA) Virus Seed for Large Scale GMP Production The genetic stability of the recombinant virus is a concern for viral vector based vaccines intended for clinical investigation, because they must be amplified multiple times to reach the scale needed for cGMP manufacturing process (Wyatt et al. 2009; Earl et al. 2009). The vector must retain its potency to fulfill expectations of regulatory agencies including FDA that require the manufacturing process not irrevocably alter the virus structure or the potency of the vaccine. Genetically stable pp65-IEfusion-MVA virus seed was generated and tested according to the examples above and was further characterized to optimize virus productivity and to establish feasibility for its use in large scale GMP production.

mH5-IEfusion-pZWIIA (GUS) shuttle plasmid (as described above) was generated using an endotoxin-free preparation (Qiagen) and was verified by restriction enzyme digestion (AscI and Pme I) and DNA sequence analysis (FIG. 19). The mH5-IEfusion-pZWIIA (GUS) was transfected into MVA 572.FHE-22.02-1974 infected primary CEF cells and screened based on the gus marker gene. Ten independent isolates (R10 isolates) were selected for the first round of plaque isolation and were screened for IEfusion antigen by immunostaining using anti-CMV IE1 mAb (p63-27). The five isolates having the highest expression in the first round were selected for the second round of plaque isolation. Ten rounds of plaque isolation were conducted, using five isolates at each successive round. At rounds 3, 6, 8 and 10, qPCR using primers shown in Table 1 above was performed to determine gene copy numbers of IEfusion and contaminating wtMVA. Gene copy numbers were determined using SYBR Green as a reporter. An IEfusion standard curve was established using plasmid copy numbers from $10^2$ to $10^7$ (FIG. 29). Each isolate was then measured against the standard curve. An exemplar amplification plot for R10 isolate sample 8B1A1A1A (9.00E+07 copies; FIG. 29) is shown in FIG. 20. The qPCR Results for IEfusion-MVA R10 isolates are shown in Table 3 below.

TABLE 3 qPCR Data for IEfusion-MVA R10 Isolates

| R10 Isolates | IEfusion copy # | wt copy # | MVA backbone # |
|---|---|---|---|
| 7A2B2B1B1C | 1.59E+07 | undetected | 1.74E+07 |
| 7A2B2B1B1C | 1.64E+07 | undetected | 1.94E+07 |
| 7A2B2B1B1D | 5.93E+07 | undetected | 1.03E+08 |
| 7A2B2B1B1D | 6.21E+07 | undetected | 9.54E+07 |
| 8B1A1B1B1A | 7.02E+06 | undetected | 1.99E+07 |
| 8B1A1B1B1A | 6.54E+06 | undetected | 1.66E+07 |
| 8B1A1A1A (R8) | 9.00E+07 | undetected | 2.22E+08 |

Figure 21:
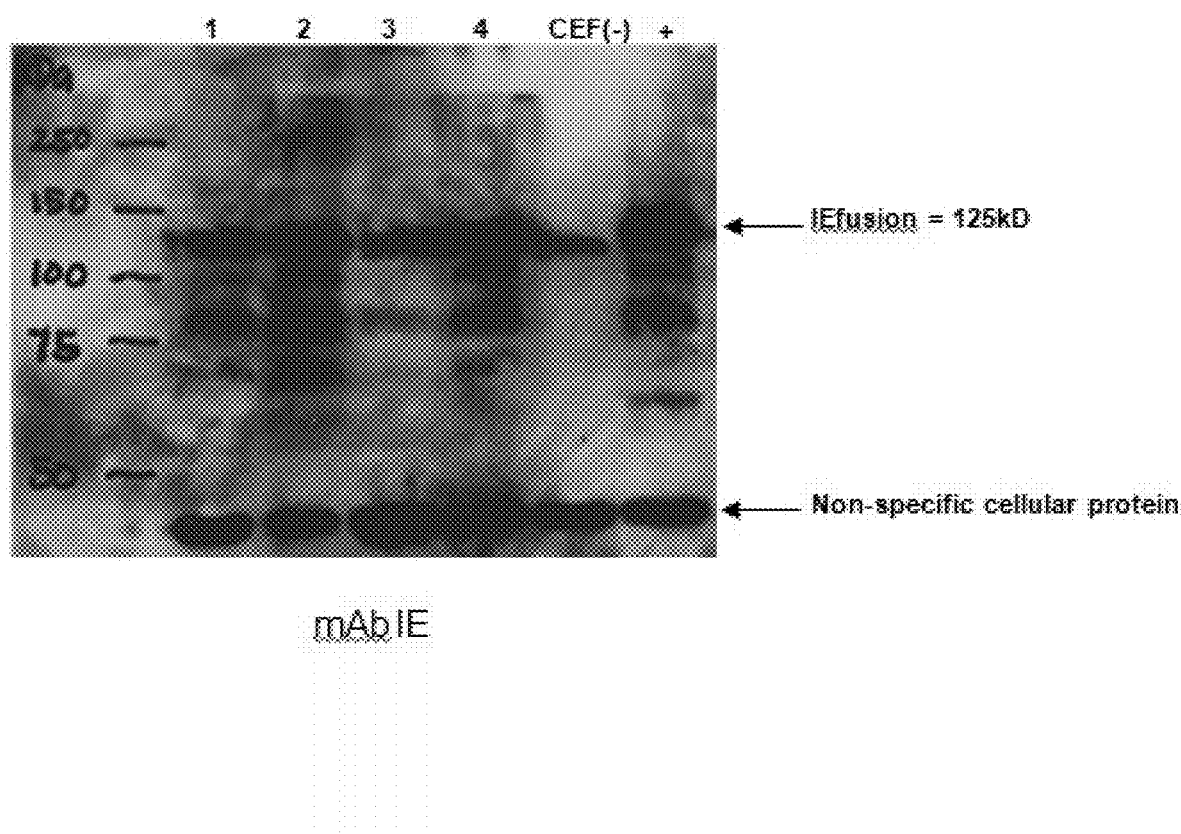
FIG. 21 is a Western blot detecting IEfusion antigen in four wt-free MVA isolates (8B1A1A1A (lane 1), 8B1A1B1B1A (lane 2), 7A2B2B1B1C (lane 3) and 7A2B2B1B1 D (lane 4)).
Figure 22:
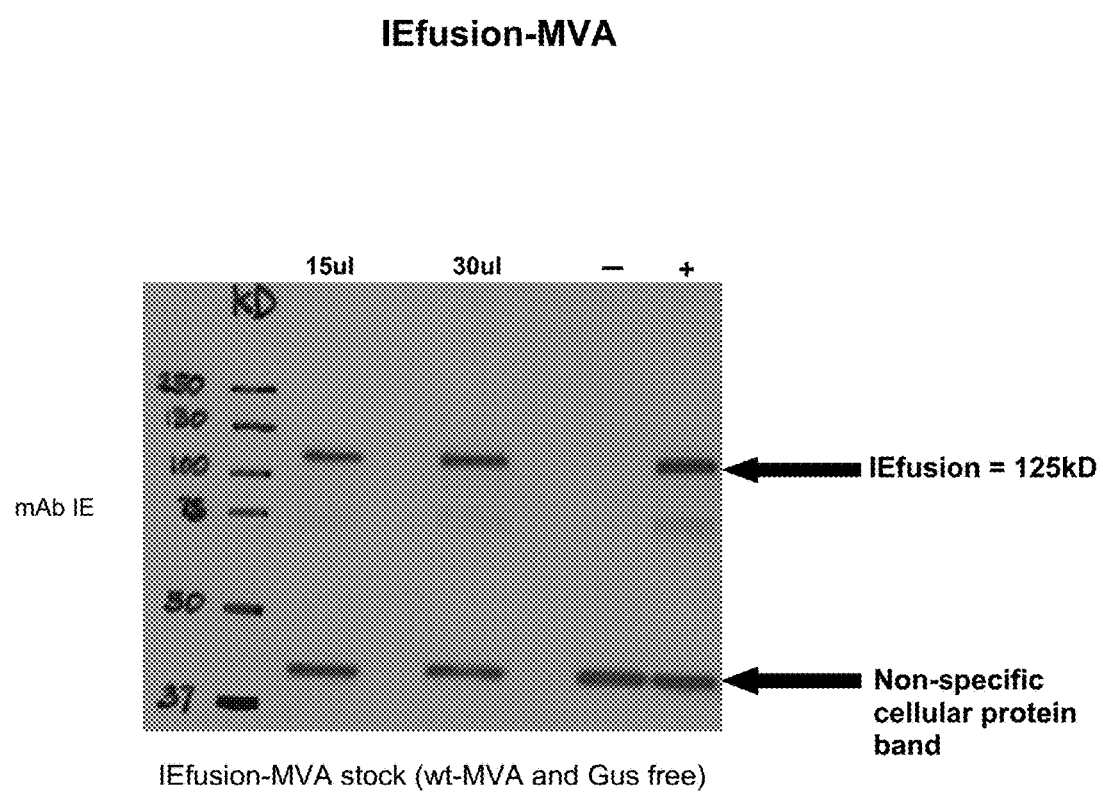
FIG. 22 is a Western blot detecting IEfusion protein expression in an expanded sample that was confirmed to be gus marker-free and wt-MVA-free, and that had a high IEfusion gene copy number.
Figure 23:
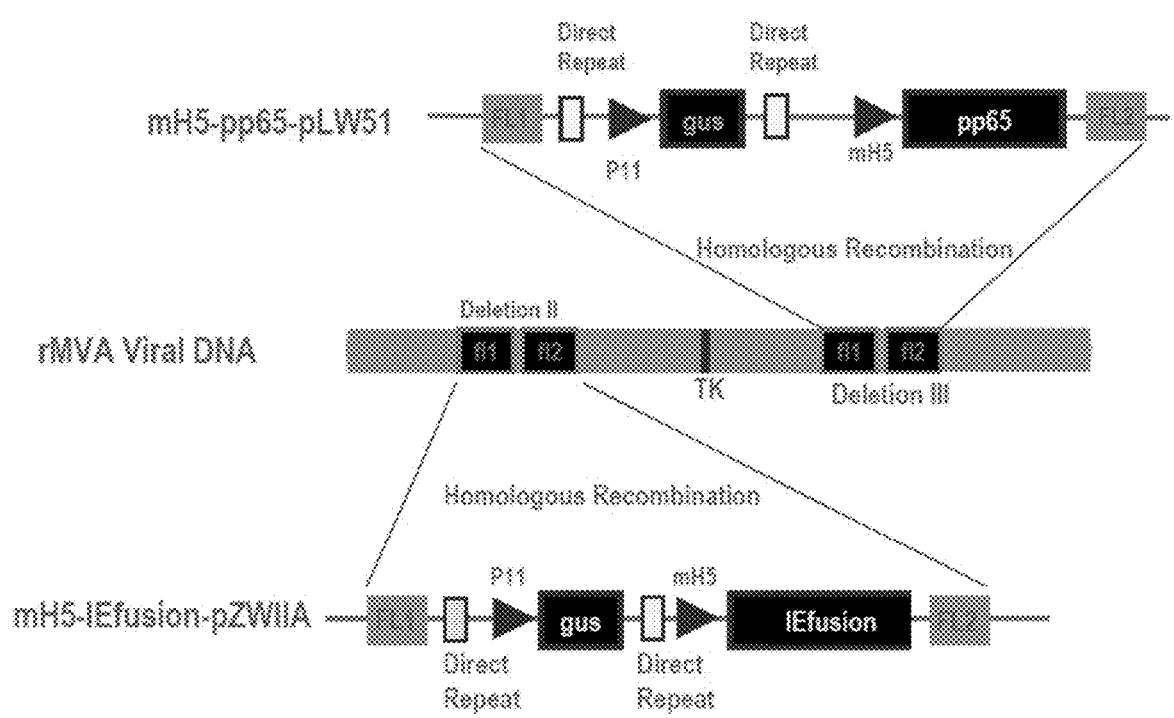
FIG. 23 is a schematic representation of the mH5-IEfusion-pZWIIA (GUS) construct that is inserted at the Deletion II (del II) insertion site on the rMVA Viral DNA and the hH5-pp65-pLW51 (GUS) construct that is inserted at the Deletion III (del III) insertion site on the rMVA Viral DNA.
Figure 24:
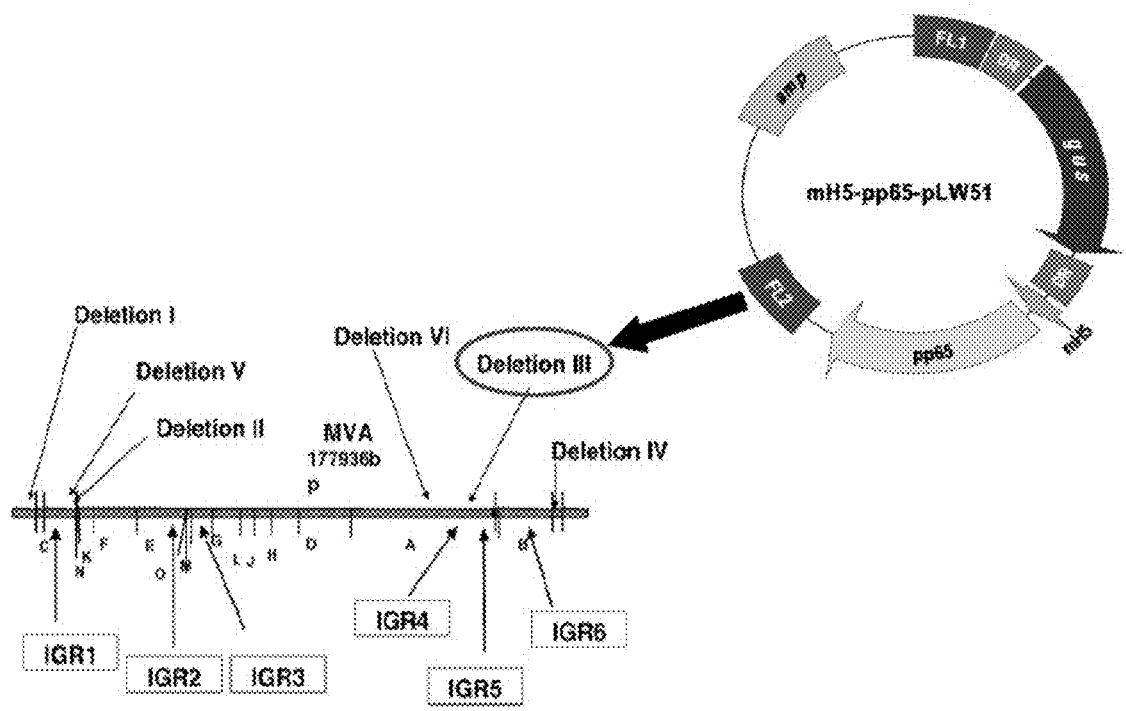
FIG. 24 is a scheme of the MVA genome showing deletions and intergenic regions (IGRs). The MVA deletion III insertion site (del III) for the mH5-pp65-pLW51 (GUS) shuttle plasmid is shown by the arrow. The shuttle plasmid has insertion sites for foreign genes (pp65) controlled by an mH5 promoter, a marker gene (gus), homologous flanking sequences for recombination (FL1, FL2), ampicillin resistance (amp) and direct repeats for marker gene removal (DR).

Four wt-free MVA isolates (8B1A1A1A, 8B1A1B1B1A, 7A2B2B1B1C and 7A2B2B1B1D) were expanded to create candidate expanded stocks. The stocks were then further characterized for microbial contamination, and were analyzed by Western blot for detection of IEfusion antigen and virus titer (FIG. 21). The gus marker gene was then removed by limiting dilution from two of the candidates (8B1A1B1B1A and 7A2B2B1B1D), and non-blue samples were screened by immunostaining to verify IEfusion expression. Samples that were positive for IEfusion were analyzed by qPCR for the presence of the IEfusion gene and absence of gus and wt-MVA genes. One sample that was confirmed to be gus marker gene-free, wt-MVA-free and had a high IEfusion gene copy number was selected and the selected expanded stock and further characterized for microbial contamination, IEfusion protein expression by Western blot (FIG. 22), and titer. The IEfusion-MVA was sequenced (SAIC-F COTR) to verify that no point mutations occurred.

Figure 25:
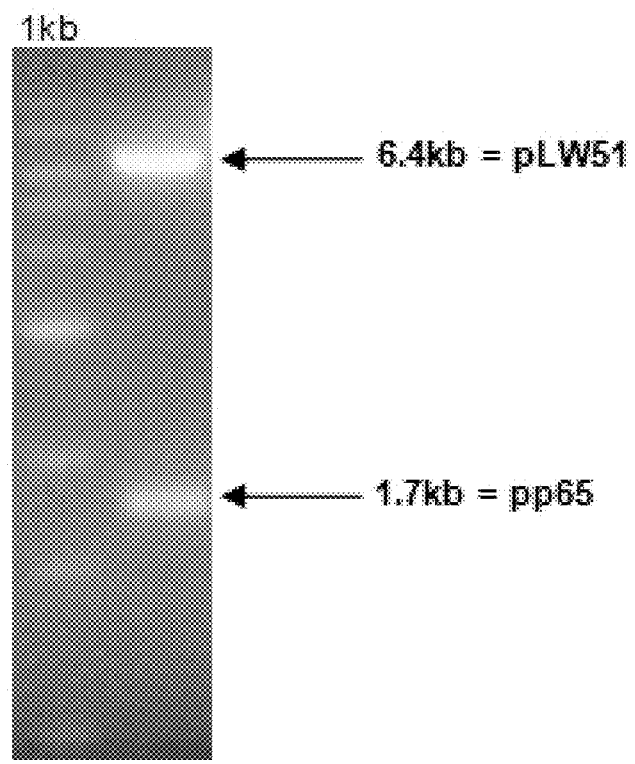
FIG. 25 is a Western blot verifying pp65 incorporation by restriction enzyme digestion (Asc I and Pme I) followed by DNA sequence analysis.

After the IEfusion-MVA virus seed was established, pp65-IE-fusion-MVA (CMV-MVA) was generated. Briefly, CEF cells were simultaneously infected with IEfusion-MVA generated in the first step and mH5-pp65-pLW51 shuttle plasmid that was verified by restriction enzyme digestion (Asc I and Pme I) and DNA sequence analysis (FIG. 25). The co-infected CEF cells were screened based on the gus marker gene. Eight rounds of plaque isolation were performed, and 15-20 plaques (gus+) were selected at each round.

Figure 26A:
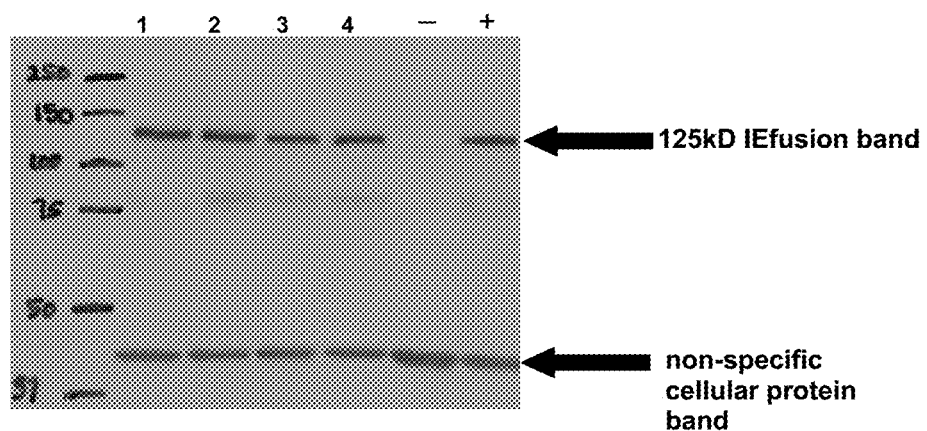
FIGS. 26A and 26B are a set of Western blots detecting IEfusion (FIG. 26A) and pp65 (FIG. 26B) in four expansion candidates (14B1C2A3B (lane 1), 14B1C2E4B (lane 2), 14B1C2E7C (lane 3), and 14B1C2F1B (lane 4))
Figure 26B:
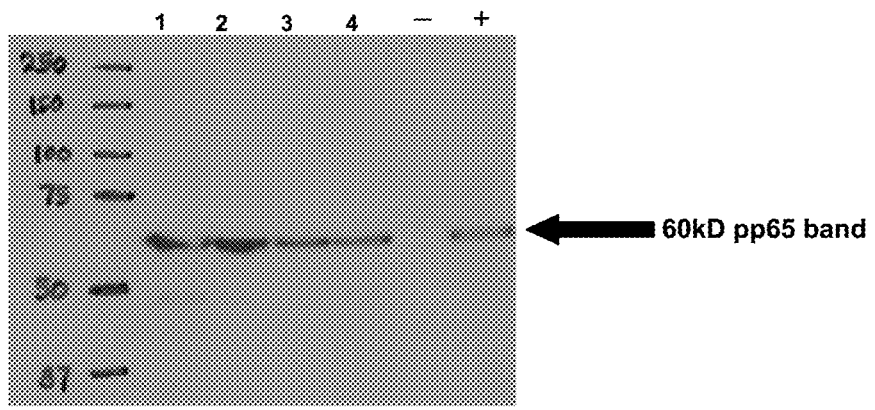

The plaques were immunostained at each round using mAb against IE (p63-27) and pp65 (28-103). After the eighth round (R8), eighteen samples were characterized by qPCR for absence of parental MVA (IEfusion-MVA) and for detection of IEfusion, pp65, MVA backbone copy numbers, and candidates for expansion are shown in Table 4 below. All eighteen samples were determined to be parental MVA-free, and detection of IEfusion (FIG. 26A) and pp65 (FIG. 26B) was confirmed.

TABLE 4 pp65-IEfusion-MVA: Candidates for Expansion

| R8 Sample ID | IEfusion copy # | pp65 copy # | MVA backbone copy # | Deletion III copy # | IE:pp65 copy ratio | IE:backbone copy ratio | pp65:backbone copy ratio |
|---|---|---|---|---|---|---|---|
| 14B1C2A3B | $1.48 \times 10^7$ | $9.65 \times 10^6$ | $9.15 \times 10^6$ | Undetected | 1.5 | 1.6 | 1.05 |
| 14B1C2E4B | $7.81 \times 10^6$ | $7.94 \times 10^6$ | $5.01 \times 10^6$ | Undetected | 0.98 | 1.56 | 1.58 |
| 14B1C2E7C | $1.23 \times 10^7$ | $1.10 \times 10^7$ | $1.19 \times 10^7$ | Undetected | 1.1 | 1.03 | 0.92 |
| 14B1C2F1B | $1.27 \times 10^7$ | $1.65 \times 10^7$ | $1.28 \times 10^7$ | Undetected | 0.77 | 0.99 | 1.29 |

Figure 27A:
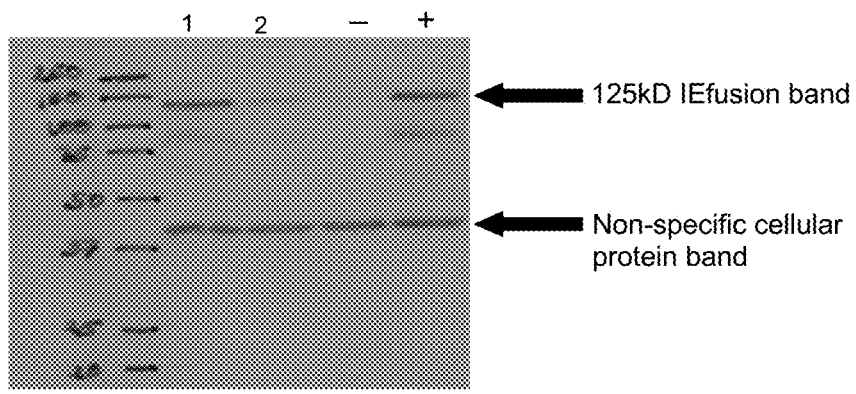
FIGS. 27A and 27B are a set of Western blots detecting IEfusion (FIG. 27A) and pp65 (FIG. 27B) in two expansion candidates, F8 (lane 1) and 23D5 (lane 2), that were gus marker-free, parental MVA-free and that had equivalent copy numbers of IEfusion and pp65.
Figure 27B:
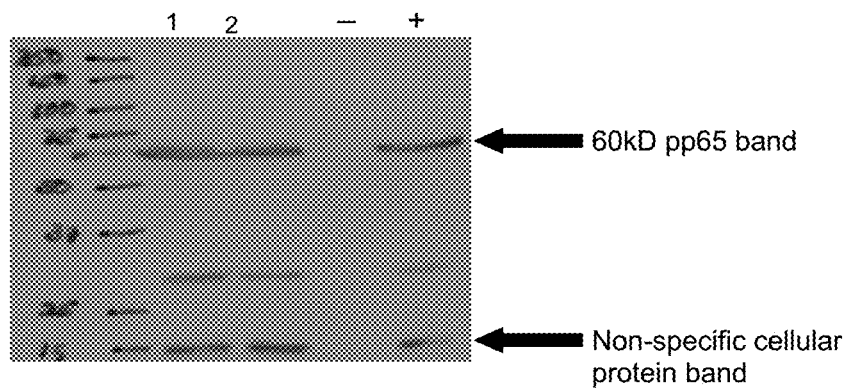

The gus marker was removed from two candidates by limiting dilution, and non-blue samples for IE and pp65 were immunostained for antigen expression. Samples that were positive by immunostaining for both IE and pp65 were characterized by qPCR for absence of gus and presence of IEfusion and pp65. Two samples that that had equivalent copy numbers of IEfusion and pp65 and were gus marker gene-free and parental MVA-free were identified (F8 and 23D5) and the two pp65-IEfusion-MVA were expanded. The expanded pp65-IEfusion-MVA were completely characterized for microbial contamination, and were analyzed by Western blot for detection of IEfusion (FIG. 27A) antigen, pp65 (FIG. 27B) antigen and virus titer.

Figure 28A:
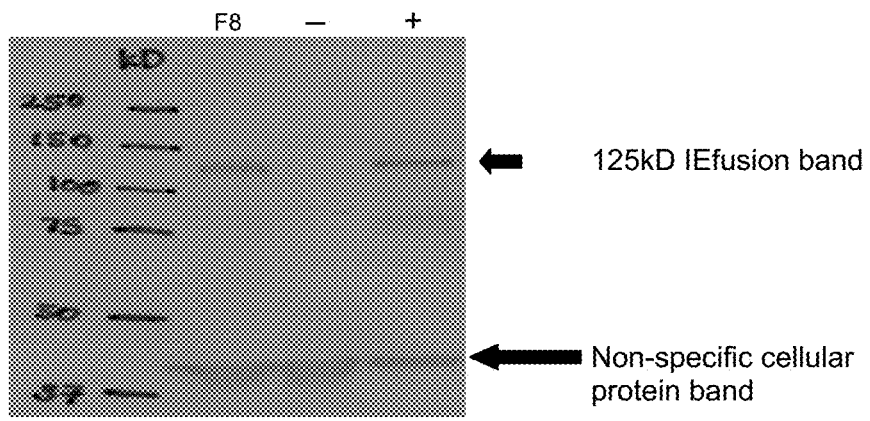
FIGS. 28A and 28B are a set of Western blots detecting IEfusion (FIG. 28A) and pp65 (FIG. 28B) in the selected virus seed, candidate F8.
Figure 28B:
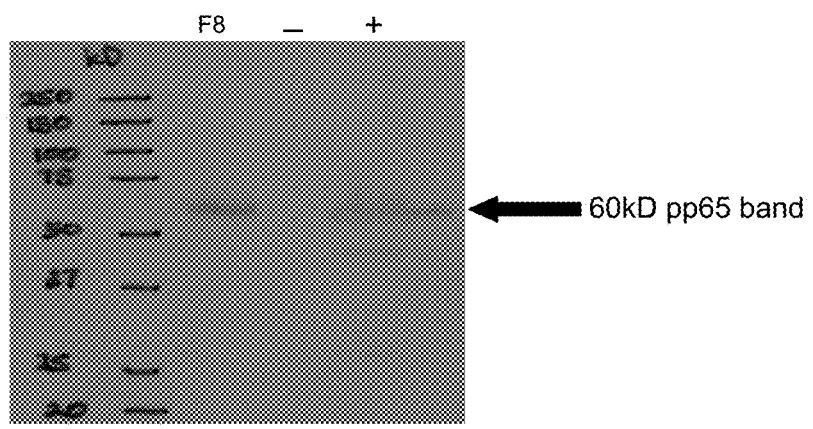

For large-scale expansion, twenty-five T-175 flasks were used to generate the CMV-MVA seed for the expanded sample F8, which expressed both IEfusion and pp65 described above. Complete characterization was accomplished by plaque assay titration, detection of IEfusion (FIG. 28A) and pp65 (FIG. 28B) by Western blot, host cell restriction, microbial and *mycoplasma* contamination tests, and sequence identity. The CNV-MVA virus seed was negative for microbial and *mycoplasma* contamination tests, the CMV-MVA virus seed titer was $1.95 \times 10^8$ pfu/ml, and the sequence identity of the virus seed was confirmed by SAIC-F COTR. Use of the CMV-MVA seed described herein for large-scale GMP production is thus feasible.

REFERENCES

The references listed below, and all references cited in the specification are hereby incorporated by reference in their entirety.

1. Antoine, G., Scheiflinger, F., Dorner, F., Falkner, F. G., 1998. The complete genomic sequence of the modified vaccinia Ankara strain: comparison with other orthopoxviruses. Virology 244:365-396.
2. Acres, B. 2007. Cancer immunotherapy: phase II clinical studies with TG4010 (MVA-MUC1-IL2). J Buon 12 Suppl 1:S71-5.
3. Avetisyan, G., Aschan, J., Hagglund, H., Ringden, O., Ljungman, P., 2007. Evaluation of intervention strategy based on CMV-specific immune responses after allogeneic SCT. Bone Marrow Transplant 40:865-869.
4. Azuma A, Huang P, Matsuda A, Plunkett W. 2_-C-cyano-2_-deoxy-1-beta-Darabino-pentofuranosylcytosine: a novel anticancer nucleoside analog that causes both DNA strand breaks and G(2) arrest. Mol Pharmacol 2001; 59(4):725-31.
5. Barouch, D. H., McKay, P. F., Sumida, S. M., Santra, S., Jackson, S. S., Gorgone, D. A., Lifton, M. A., Chakrabarti, B. K., Xu, L., Nabel, G. J., Letvin, N. L., 2003. Plasmid chemokines and colonystimulating factors enhance the immunogenicity of DNApriming-viral vector boosting human immunodeficiency virus type 1 vaccines. J. Virol. 77:8729-8735.
6. Berencsi, K., Gyulai, Z., Gonczol, E., Pincus, S., Cox, W. I., Michelson, S., Kari, L., Meric, C., Cadoz, M., Zahradnik, J., Starr, S., Plotkin, S., 2001. A canarypox vector-expressing cytomegalovirus (cmv) phosphoprotein 65 induces long-lasting cytotoxic t cell responses in human cmv-seronegative subjects. J. Infect. Dis. 183:1171-1179
7. Blanchard, T. J., Alcami, A., Andrea, P., Smith, G. L., 1998. Modified vaccinia virus Ankara undergoes limited replication in human cells and lacks several immunomodulatory proteins: implications for use as a human vaccine. J. Gen. Virol. 79 (Pt 5):1159-1167.
8. Britt, W. J., and D. Auger. 1985. Identification of a 65 000 dalton virion envelope protein of human cytomegalovirus. Virus Res 4:31-6.
9. Britt W J, Vugler L. Structural and immunological characterization of the intracellular forms of an abundant 68,000 Mr human cytomegalovirus protein. J Gen Virol 1987; 68(Pt 7):1897-907.
10. Boeckh, M., Nakamura, R., Cornelissen, J. J., Zaia, J. A., Forman, S. J., Gaal, K., Brooimans, R. A., Gratama, J. W., Gasior, G. H., Sullivan, L. A., 2006. Immune monitoring with iTAg™ MHC tetramers for prediction of recurrent or persistent cytomegalovirus (CMV) infection in allogeneic stem cell transplant (SCT) recipients: a prospective multicenter clinical trial. Biol. Blood Marrow Transplant. 12:79.
11. Butrapet S, Kinney R M, Huang C Y. Determining genetic stabilities of chimeric dengue vaccine candidates based on dengue 2 PDK-53 virus by sequencing and quantitative TaqMAMA. J Virol Methods 2006; 131(1): 1-9.
12. Carroll, M. W., Overwijk, W. W., Chamberlain, R. S., Rosenberg, S. A., Moss, B., Restifo, N. P., 1997a. Highly attenuated modified vaccinia virus Ankara (MVA) as an effective recombinant vector: a murine tumor model. Vaccine 15:387-394
13. Carroll, M. W., Moss, B., 1997b. Host range and cytopathogenicity of the highly attenuated MVA strain of vaccinia virus: propagation and generation of recombinant viruses in a nonhuman mammalian cell line. Virology 238:198-211.
14. Chakrabarti, S., J. R. Sisler, and B. Moss. 1997. Compact, synthetic, vaccinia virus early/late promoter for protein expression. Biotechniques 23:1094-7.
15. Cobbold, M., Khan, N., Pourgheysari, B., Tauro, S., McDonald, D., Osman, H., Assenmacher, M., Billingham, L., Steward, C., Crawley, C., Olavarria, E., Goldman, J., Chakraverty, R., Mahendra, P., Craddock, C., Moss, P. A., 2005. Adoptive transfer of cytomegalovirus-specific CTL to stem cell transplant patients after selection by HLA-peptide tetramers. J. Exp. Med. 202:379-386.
16. Cosma, A., R. Nagaraj, S. Buhler, J. Hinkula, D. H. Busch, G. Sutter, F. D. Goebel, and V. Erfle. 2003. Therapeutic vaccination with MVA-HIV-1 nef elicits Nef-specific T-helper cell responses in chronically HIV-1 infected individuals. Vaccine 22:21-9.
17. Cwynarski, K., Ainsworth, J., Cobbold, M., Wagner, S., Mahendra, P., Apperley, J., Goldman, J., Craddock, C., Moss, P. A., 2001. Direct visualization of cytomegalovirusspecific T-cell reconstitution after allogeneic stem cell transplantation. Blood 97:1232-1240
18. Daftarian, P., Sharan, R., Haq, W., Ali, S., Longmate, J., Termini, J., Diamond, D. J., 2005. Novel conjugates of epitope fusion peptides with CpG-ODN display enhanced immunogenicity and HIV recognition. Vaccine 23:3453-3468.
19. Dawson R M C, Elliott D C, Elliott W H, Jones K M. Data for biochemical research. Oxford University Press; 1986. p. 260-1.
20. de Haan, C. A., B. J. Haijema, D. Boss, F. W. Heuts, and P. J. Rottier. 2005. Coronaviruses as vectors: stability of foreign gene expression. J Virol 79:12742-51.
21. deWaal, L., Wyatt, L. S., Yuksel, S., van Amerongen, G., Moss, B., Niesters, H. G., Osterhaus, A. D., de Swart, R. L., 2004. Vaccination of infant macaques with a recombinant MVA expressing the RSV F and G genes does not predispose for immunopathology. Vaccine 22:923-926.
22. Diamond, D. J., J. York, J. Y. Sun, C. L. Wright, and S. J. Forman. 1997. Development of a candidate HLA A*0201 restricted peptide-based vaccine against human cytomegalovirus infection. Blood 90:1751-67.
23. Drexler, I., C. Staib, and G. Sutter. 2004. Modified vaccinia virus Ankara as antigen delivery system: how can we best use its potential? Curr Opin Biotechnol 15:506-12.
24. Earl, P. L., Americo, J. L., Wyatt, L. S., Eller, L. A., Montefiori, D. C., Byrum, R., Piatak, M., Lifson, J. D., Amara, R. R., Robinson, H. L., Huggins, J. W., Moss, B., 2007. Recombinant modified vaccinia virus Ankara provides durable protection against disease caused by an immunodeficiency virus as well as long-term immunity to an orthopoxvirus in a non-human primate. Virology 366: 84-97.
25. Earl P L, Cotter C, Moss B, Vancott T, Currier J, Eller L A, et al. Design and evaluation of multi-gene, multiclade HIV-1MVA vaccines. Vaccine 2009; 27(42):5885-95.
26. Einsele, H., Roosnek, E., Rufer, N., Sinzger, C., Riegler, S., Loffler, J., Grigoleit, U., Moris, A., Rammensee, H. G., Kanz, L., Kleihauer, A., Frank, F., Jahn, G., Hebart, H., 2002. Infusion of cytomegalovirus (CMV)-specific T cells for the treatment of CMV infection not responding to antiviral chemotherapy. Blood 99:3916-3922.
27. Erfle V, Goebel F D, Guzman C A, Le Grand R. Vaccines based on Nef and on Nef/DeltaV2 Env. Microbes Infect 2005; 7(14):1400-4.
28. Espenschied, J., J. Lamont, J. Longmate, S. Pendas, Z. Wang, D. J. Diamond, and J. D. Ellenhorn. 2003. CTLA-4 blockade enhances the therapeutic effect of an attenuated poxvirus vaccine targeting p53 in an established murine tumor model. J Immunol 170:3401-7.
29. Fayzulin R, Scholle F, Petrakova O, Frolov I, Mason P W. Evaluation of replicative capacity and genetic stability of West Nile virus replicons using highly efficient packaging cell lines. Virology 2006; 351(1):196-209.
30. Firat, H., Cochet, M., Rohrlich, P. S., Garcia-Pons, F., Darche, S., Danos, O., Lemonnier, F. A., Langlade-Demoyen, P., 2002. Comparative analysis of the CD8(+) T cell repertoires of H-2 class I wild-type/HLA-A2.1 and H-2 class I knockout/HLA-A2.1 transgenic mice. Int. Immunol. 14:925-934.
31. Gallez-Hawkins, G., Thao, L., Lacey, S. F., Martinez, J., Li, X., Franck, A. E., Lomeli, N. A., Longmate, J., Diamond, D. J., Spielberger, R., Forman, S. J., Zaia, J. A., 2005. Cytomegalovirusimmune reconstitution occurs in recipients of allogeneic hematopoietic celltransplants irrespective of detectable cytomegalovirus infection. Biol. Blood Marrow Transplant. 11:890-902.
32. Ghanekar, S. A., Nomura, L. E., Suni, M. A., Picker, L. J., Maecker, H. T., Maino, V. C., 2001. Gamma interferon expression in CD8(+) T cells is a marker for circulating cytotoxic T lymphocytes that recognize an HLA A2-restricted epitope of human cytomegalovirus phosphoprotein pp65. Clin. Diagn. Lab. Immunol. 8:628-631.
33. Gherardi, M. M., and M. Esteban. 2005. Recombinant poxviruses as mucosal vaccine vectors. J Gen Virol 86:2925-36.
34. Gilbert, M. J., Riddell, S. R., Li, C. R., Greenberg, P. D., 1993. Selective interference with class I major histocompatibility complex presentation of the major immediate-early protein following infection with human cytomegalovirus. J. Virol. 67:3461-3469.
35. Gilbert, M. J., Riddell, S. R., Plachter, B., Greenberg, P. D., 1996. Cytomegalovirus selectively blocks antigen processing and presentation of its immediate-early gene product. Nature 383:720-722.
36. Gilbert, S. C., V. S. Moorthy, L. Andrews, A. A. Pathan, S. J. McConkey, J. M. Vuola, S. M. Keating, T. Berthoud, D. Webster, H. McShane, and A. V. Hill. 2006. Synergistic DNA-MVA prime-boost vaccination regimes for malaria and tuberculosis. Vaccine 24:4554-61.
37. Gomez, C. E., Najera, J. L., Jimenez, E. P., Jimenez, V., Wagner, R., Graf, M., Frachette, M. J., Liljestrom, P., Pantaleo, G., Esteban, M., 2007. Head-to-head comparison on the immunogenicity of two HIV/AIDS vaccine candidates based on the attenuated poxvirus strains MVA and NYVAC co-expressing in a single locus the HIV-1BX08 gp120 and HIV-1(IIIB) Gag-Pol-Nef proteins of clade B. Vaccine 25:2863-2885.
38. Goonetilleke, N., Moore, S., Daily, L., Winstone, N., Cebere, I., Mahmoud, A., Pinheiro, S., Gillespie, G., Brown, D., Loach, V., Roberts, J., Guimaraes-Walker, A., Hayes, P., Loughran, K., Smith, C., De Bont, J., Verlinde, C., Vooijs, D., Schmidt, C., Boaz, M., Gilmour, J., Fast, P., Dorrell, L., Hanke, T., McMichael, A. J., 2006. Induction of multifunctional human immunodeficiency virus type 1 (HIV-1)-specific T cells capable of proliferation in healthy subjects by using a prime-boost regimen of DNA and modified vaccinia virus Ankara-vectored vaccines expressing HIV-1 gag coupled to CD8+ T-cell epitopes. J. Virol. 80:4717-4728
39. Gratama, J. W., van Esser, J. W., Lamers, C. H., Tournay, C., Lowenberg, B., Bolhuis, R. L., Cornelissen, J. J., 2001. Tetramer-based quantification of cytomegalovirus (CMV)-specific CD8+ T lymphocytes in T-cell-depleted stem cell grafts and after transplantation may identify patients at risk for progressive CMV infection. Blood 98:1358-1364.
40. Gyulai, Z., Endresz, V., Burian, K., Pincus, S., Toldy, J., Cox, W. I., Meri, C., Plotkin, S., Berencsi, K., 2000. Cytotoxic T lymphocyte (CTL) responses to human cytomegalovirus pp65, IE1-Exon4, gB, pp150, and pp28 in healthy individuals: reevaluation of prevalence of IE1-Specific CTLs. J. Infect. Dis. 181:1537-1546.
41. Hanke, T., McMichael, A. J., Dennis, M. J., Sharpe, S. A., Powell, L. A., Mcloughlin, L., Crome, S. J., 2005. Biodistribution and persistence of an MVA-vectored can- 42. Johnson, R. A., Yurochko, A. D., Poma, E. E., Zhu, L., Huang, E. S., 1999. Domain mapping of the human cytomegalovirus IE1-72 and cellular p107 protein-protein interaction and the possible functional consequences. J. Gen. Virol. 80(5):1293-1303.

43. Kern, F., Surel, I. P., Faulhaber, N., Frommel, C., Schneider-Mergener, J., Schonemann, C., Reinke, P., Volk, H. D., 1999. Target structures of the CD8(+)-T-cell response to human cytomegalovirus: the 72-kilodalton major immediate-early protein revisited. J. Virol. 73:8179-8184.

44. Khan, N., M. Cobbold, R. Keenan, and P. A. Moss. 2002. Comparative analysis of CD8+ T cell responses against human cytomegalovirus proteins pp65 and immediate early 1 shows similarities in precursor frequency, oligoclonality, and phenotype. J Infect Dis 185:1025-34.

45. Khan, N., Bruton, R., Taylor, G. S., Cobbold, M., Jones, T. R., Rickinson, A. B., Moss, P. A., 2005. Identification of cytomegalovirus-specific cytotoxic T lymphocytes in vitro is greatly enhanced by the use of recombinant virus lacking the US2 to US11 region or modified vaccinia virus Ankara expressing individual viral genes. J. Virol. 79:2869-2879.

46. Khan, N., Best, D., Bruton, R., Nayak, L., Rickinson, A. B., Moss, P. A., 2007. T cell recognition patterns of immunodominant cytomegalovirus antigens in primary and persistent infection. J. Immunol. 178:4455-4465.

47. Khanna, R., Diamond, D. J., 2006. Human cytomegalovirus vaccine: time to look for alternative options. Trends Mol. Med. 12:26-33

48. Kidokoro M, Tashiro M, Shida H. Genetically stable and fully effective smallpox vaccine strain constructed from highly attenuated vaccinia LC16m8. Proc Natl Acad Sci USA 2005; 102(11):4152-7.

49. Krishnan A, Wang Z, Srivastava T, Rawal R, Manchanda P, Diamond D J, et al. A novel approach to evaluate the immunogenicity of viral antigens of clinical importance in HLA transgenic murine models. Immunol Lett 2008; 120(1-2):108-16.

50. La Rosa, C., R. Krishnan, S. Markel, J. P. Schneck, R. Houghten, C. Pinilla, and D. J. Diamond. 2001. Enhanced immune activity of cytotoxic T-lymphocyte epitope analogs derived from positional scanning synthetic combinatorial libraries. Blood 97:1776-86.

51. La Rosa, C., Z. Wang, S. F. Lacey, M. M. Lalimarmo, A. Krishnan, J. Longmate, and D. J. Diamond. 2006. In vitro expansion of polyclonal T-cell subsets for adoptive immunotherapy by recombinant modified vaccinia Ankara. Exp Hematol 34:497-507.

52. La Rosa, C., Limaye, A. P., Krishnan, A., Longmate, J., Diamond, D. J., 2007. Longitudinal assessment of cytomegalovirus (CMV)-specific immune responses in liver transplant recipients at high risk for late CMV disease. J. Infect. Dis. 195:633-644.

53. La Rosa C, Wang Z, Brewer J C, Lacey S F, Villacres M C, Sharan R, et al. Preclinical development of an adjuvant-free peptide vaccine with activity against CMV pp65 in HLA transgenic mice. Blood 2002; 100(10):3681-9.

54. Lacey, S. F., La Rosa, C., Zhou, W., Sharma, M. C., Martinez, J., Krishnan, A., Gallez-Hawkins, G., Thao, L., Longmate, J., Spielberger, R., Forman, S. J., Limaye, A., Zaia, J. A., Diamond, D. J., 2006. Functional comparison of T cells recognizing cytomegalovirus pp65 and intermediate-early antigen polypeptides in hematopoietic stem-cell transplant and solid organ transplant recipients. J. Infect. Dis. 194:1410-1421

55. Lai, A. C., and Y. Chu. 1991. A rapid method for screening vaccinia virus recombinants. Biotechniques 10:564-5.

56. Lemonnier, F. A., 2002. The utility of H-2 class I knockout mice. Virus Res. 82:87-90.

57. Limaye, A. P., Bakthavatsalam, R., Kim, H. W., Randolph, S. E., Halldorson, J. B., Healey, P. J., Kuhr, C. S., Levy, A. E., Perkins, J. D., Reyes, J. D., Boeckh, M., 2006. Impact of cytomegalovirus in organ transplant recipients in the era of antiviral prophylaxis. Transplantation 81(12):1645-1652.

58. Ljungman, P., Perez-Bercoff, L., Jonsson, J., Avetisyan, G., Sparrelid, E., Aschan, J., Barkholt, L., Larsson, K., Winiarski, J., Yun, Z., Ringden, O., 2006. Risk factors for the development of cytomegalovirus disease after allogeneic stem cell transplantation. Haematologica 91:78-83.

59. Longmate, J., York, J., La Rosa, C., Krishnan, R., Zhang, M., Senitzer, D., Diamond, D. J., 2001. Population coverage by HLA class-I restricted cytotoxic T-lymphocyte epitopes. Immunogenetics 52:165-173.

60. Maecker, H. T., Moon, J., Bhatia, S., Ghanekar, S. A., Maino, V. C., Payne, J. K., Kuus-Reichel, K., Chang, J. C., Summers, A., Clay, T. M., Morse, M. A., Lyerly, H. K., DeLaRosa, C., Ankerst, D. P., Disis, M. L., 2005. Impact of cryopreservation on tetramer, cytokine flow cytometry, and ELISPOT. BMC Immunol. 6:17.

61. Mayr, A., Danner, K., 1978. Vaccination against pox diseases under immunosuppressive conditions. Dev. Biol. Stand. 41:225-34, 225-234.

62. Manley, T. J., Luy, L., Jones, T., Boeckh, M., Mutimer, H., Riddell, S. R., 2004. Immune evasion proteins of human cytomegalovirus do not prevent a diverse CD8+ cytotoxic T-cell response in natural infection. Blood 104: 1075-1082.

63. Meyer, H., Sutter, G., Mayr, A., 1991. Mapping of deletions in the genome of the highly attenuated vaccinia virusMVA and their influence on virulence. J. Gen. Virol. 72(5):1031-1038.

64. Moorthy, V. S., Pinder, M., Reece, W. H., Watkins, K., Atabani, S., Hannan, C., Bojang, K., McAdam, K. P., Schneider, J., Gilbert, S., Hill, A. V., 2003. Safety and immunogenicity of DNA/modified vaccinia virus ankara malaria vaccination in African adults. J. Infect. Dis. 188:1239-1244.

65. Morello, C. S., Cranmer, L. D., Spector, D. H., 2000. Suppression of murine cytomegalovirus (MCMV) replication with a DNA vaccine encoding MCMV M84 (a homolog of human cytomegalovirus pp65). J. Virol. 74:3696-3708.

66. Moss, B., M. W. Carroll, L. S. Wyatt, J. R. Bennink, V. M. Hirsch, S. Goldstein, W. R. Elkins, T. R. Fuerst, J. D. Lifson, M. Piatak, N. P. Restifo, W. Overwijk, R. Chamberlain, S. A. Rosenberg, and G. Sutter. 1996. Host range restricted, non-replicating vaccinia virus vectors as vaccine candidates. Adv Exp Med Biol 397:7-13.

67. Moss B. Genetically engineered poxviruses for recombinant gene expression, vaccination, and safety. Proc Natl Acad Sci USA 1996; 93(21):11341-8.

68. Pascolo, S., Bervas, N., Ure, J. M., Smith, A. G., Lemonnier, F. A., Perarnau, B., 1997. HLAA2.1-restricted education and cytolytic activity of CD8(+) T lymphocytes from beta2 microglobulin (beta2m) HLA-A2.1 monochain transgenic H-2Db beta2m double knockout mice. J. Exp. Med. 185:2043-2051.

69. Pass, R. F., Fowler, K. B., Boppana, S. B., Britt, W. J., Stagno, S., 2006. Congenital cytomegalovirus infection following first trimester maternal infection: symptoms at birth and outcome. J. Clin. Virol. 35:216-220
70. Peters, B. S., W. Jaoko, E. Vardas, G. Panayotakopoulos, P. Fast, C. Schmidt, J. Gilmour, M. Bogoshi, G. Omosa-Manyonyi, L. Dally, L. Klavinskis, B. Farah, T. Tarragona, P. A. Bart, A. Robinson, C. Pieterse, W. Stevens, R. Thomas, B. Barin, A. J. McMichael, J. A. McIntyre, G. Pantaleo, T. Hanke, and J. Bwayo. 2007. Studies of a prophylactic HIV-1 vaccine candidate based on modified vaccinia virus Ankara (MVA) with and without DNA priming: effects of dosage and route on safety and immunogenicity. Vaccine 25:2120-7.
71. Peters, B., Sette, A., 2007. Integrating epitope data into the emerging web of biomedical knowledge resources. Nat. Rev. Immunol. 7:485-490.
72. Plachter, B., W. Britt, R. Vornhagen, T. Stamminger, and G. Jahn. 1993. Analysis of proteins encoded by IE regions 1 and 2 of human cytomegalovirus using monoclonal antibodies generated against recombinant antigens. Virology 193:642-52.
73. Ramirez, J. C., M. M. Gherardi, and M. Esteban. 2000. Biology of attenuated modified vaccinia virus Ankara recombinant vector in mice: virus fate and activation of B- and T-cell immune responses in comparison with the Western Reserve strain and advantages as a vaccine. J Virol 74:923-33.
74. Reddehase, M. J., Mutter, W., Munch, K., Buhring, H. J., Koszinowski, U. H., 1987. CD8-positive T lymphocytes specific for murine cytomegalovirus immediate-early antigens mediate protective immunity. J. Virol. 61:3102-3108.
75. Rochlitz, C., R. Figlin, P. Squiban, M. Salzberg, M. Pless, R. Herrmann, E. Tartour, Y. Zhao, N. Bizouarne, M. Baudin, and B. Acres. 2003. Phase I immunotherapy with a modified vaccinia virus (MVA) expressing human MUC1 as antigen-specific immunotherapy in patients with MUC1-positive advanced cancer. J Gene Med 5:690-9.
76. Rohrlich, P. S., Cardinaud, S., Firat, H., Lamari, M., Briand, P., Escriou, N., Lemonnier, F. A., 2003. HLA-B☐0702 transgenic, H-2KbDb double-knockout mice: phenotypical and functional characterization in response to influenza virus. Int. Immunol. 15:765-772.
77. Sandstrom E, Nilsson C, Hejdeman B, Brave A, Bratt G, Robb M, et al. Broad immunogenicity of a multigene. Multiclade HIV-1 DNA vaccine boosted with heterologous HIV-1 recombinant modified vaccinia virus Ankara. J Infect Dis 2008; 198(10):1482-90.
78. Schleiss, M. R., Lacayo, J. C., Belkaid, Y., McGregor, A., Stroup, G., Rayner, J., Alterson, K., Chulay, J. D., Smith, J. F., 2007. Preconceptual administration of an alphavirus replicon UL83 (pp65 homolog) vaccine induces humoral and cellular immunity and improves pregnancy outcome in the guinea pig model of congenital cytomegalovirus infection. J. Infect. Dis. 195:789-798.
79. Schmelz M, Sodeik B, Ericsson M, Wolffe E J, Shida H, Hiller G, et al. Assembly of vaccinia virus: the second wrapping cisterna is derived from the trans Golgi network. J Virol 1994; 68(1):130-47.
80. Sinclair, E., Black, D., Epling, C. L., Carvidi, A., Josefowicz, S. Z., Bredt, B. M., Jacobson, M. A., 2004. CMV antigen-specific CD4+ and CD8+ T cell IFNgamma expression and proliferation responses in healthy CMV-seropositive individuals. Viral Immunol. 17:445-454
81. Sinclair, E., Tan, Q. X., Sharp, M., Girling, V., Poon, C., Natta, M. V., Jabs, D. A., Inokuma, M., Maecker, H. T., Bredt, B., Jacobson, M. A., 2006. Protective immunity to cytomegalovirus (CMV) retinitis in AIDS is associated with CMV-specific T cells that express interferon-gamma and interleukin-2 and have a CD8+ cell early maturational phenotype. J. Infect. Dis. 194:1537-1546.
82. Song G. Y., Gibson G., Haq W., Huang E. C., Srivasta T., Hollstein M., Daftarian P., Wang Z., Diamond D., Ellenhorn J. D. An MVA vaccine overcomes tolerance to human p53 in mice and humans. Canc. Immunol. Immunother. 56(8):1193-205, 2007.
83. Stickl, H., V. Hochstein-Mintzel, A. Mayr, H. C. Huber, H. Schafer, and A. Holzner. 1974. MVA vaccination against smallpox: clinical tests with an attenuated live vaccinia virus strain (MVA) (author's translation). Dtsch. Med. Wochenschr 99:2386-2392.
84. Stittelaar, K. J., T. Kuiken, R. L. de Swart, G. van Amerongen, H. W. Vos, H. G. Niesters, P. van Schalkwijk, T. van der Kwast, L. S. Wyatt, B. Moss, and A. D. Osterhaus. 2001. Safety of modified vaccinia virus Ankara (MVA) in immune-suppressed macaques. Vaccine 19:3700-9.
85. Stittelaar K J, Wyatt LS, de Swart R L, Vos H W, Groen J, van Amerongen G, et al. Protective immunity in macaques vaccinated with a modified vaccinia virus Ankara-based measles virus vaccine in the presence of passively acquired antibodies. J Virol 2000; 74(9):4236-43.
86. Sutter G, Staib C. Vaccinia vectors as candidate vaccines: the development of modified vaccinia virus Ankara for antigen delivery. Curr Drug Targets Infect Disord. 2003; 3(3):263-71.
87. Sylwester, A. W., Mitchell, B. L., Edgar, J. B., Taormina, C., Pelte, C., Ruchti, F., Sleath, P. R., Grabstein, K. H., Hosken, N. A., Kern, F., Nelson, J. A., Picker, L. J., 2005. Broadly targeted human cytomegalovirus-specific CD4+ and CD8+ T cells dominate the memorycompartments of exposed subjects. J. Exp. Med. 202:673-685.
88. Timm, A., C. Enzinger, E. Felder, and P. Chaplin. 2006. Genetic stability of recombinant MVA-BN. Vaccine 24:4618-21.
89. Tobery T W, Siliciano R F. Targeting of HIV-1 antigens for rapid intracellular degradation enhances cytotoxic T lymphocyte (CTL) recognition and the induction of de novo CTL responses in vivo after immunization. J Exp Med 1997; 185(5):909-20 .
90. Uhde-Holzem K, Fischer R, Commandeur U. Genetic stability of recombinant potato virus×virus vectors presenting foreign epitopes. Arch Virol 2007; 152(4):805-11.
91. Walter, E. A., Greenberg, P. D., Gilbert, M. J., Finch, R. J., Watanabe, K. S., Thomas, E. D., Riddell, S. R., 1995. Reconstitution of cellular immunity against cytomegalovirus in recipients of allogeneic bone marrow by transfer of T-cell clones from the donor. N. Engl. J. Med. 333: 1038-1044.
92. Wang, Z., C. La Rosa, S. F. Lacey, R. Maas, S. Mekhoubad, W. J. Britt, and D. J. Diamond. 2006. Attenuated poxvirus expressing three immunodominant CMV antigens as a vaccine strategy for CMV infection. J Clin Virol 35:324-31.
93. Wang, Z., C. La Rosa, R. Maas, H. Ly, J. Brewer, S. Mekhoubad, P. Daftarian, J. Longmate, W. J. Britt, and D. J. Diamond. 2004a. Recombinant modified vaccinia virus Ankara expressing a soluble form of glycoprotein B causes durable immunity and neutralizing antibodies against multiple strains of human cytomegalovirus. J Virol 78:3965-76.
94. Wang, Z., C. La Rosa, S. Mekhoubad, S. F. Lacey, M. C. Villacres, S. Markel, J. Longmate, J. D. Ellenhorn, R. F. Siliciano, C. Buck, W. J. Britt, and D. J. Diamond. 2004b. Attenuated Poxviruses Generate Clinically Relevant Frequencies of CMV-Specific T cells. Blood 104:847-856.
95. Wang, Z., C. L. Rosa, Z. Li, H. Ly, A. Krishnan, J. Martinez, W. J. Britt, and D. J. Diamond. 2007. Vaccine properties of a novel marker gene-free recombinant modified vaccinia Ankara expressing immunodominant CMV antigens pp65 and IE1. Vaccine 25:1132-41.
96. Wang, Z., W. Zhou, T. Srivastava, C. La Rosa, A. Mandarino, S. J. Forman, J. A. Zaia, W. J. Britt, and D. J. Diamond. 2008. A fusion protein of HCMV IE1 exon4 and IE2 exon5 stimulates potent cellular immunity in an MVA vaccine vector. Virology 377:379-390.
97. Werner, G. T., U. Jentzsch, E. Metzger, and J. Simon. 1980. Studies on poxvirus infections in irradiated animals. Arch Virol 64:247-56.
98. White, E. A., Del Rosario, C. J., Sanders, R. L., Spector, D. H., 2007. The IE2 60-kilodalton and 40-kilodalton proteins are dispensable for human cytomegalovirus replication but are required for efficient delayed early and late gene expression and production of infectious virus. J. Virol. 81:2573-2583.
99. Wills, M. R., Carmichael, A. J., Mynard, K., Jin, X., Weekes, M. P., Plachter, B., Sissons, J. G., 1996. The human CTL response to cytomegalovirus is dominated by structural protein pp65: frequency, specificity, and T cell receptor usage of pp65-specific CTL. J. Virol. 70:7569-7579.
100. Wyatt, L. S., I. M. Belyakov, P. L. Earl, J. A. Berzofsky, and B. Moss. 2008a. Enhanced cell surface expression, immunogenicity and genetic stability resulting from a spontaneous truncation of HIV Env expressed by a recombinant MVA. Virology 372(2):260-72 (Epub 2007 Nov. 28).
101. Wyatt, L. S., P. L. Earl, J. Vogt, L. A. Eller, D. Chandran, J. Liu, H. L. Robinson, and B. Moss. 2008b. Correlation of immunogenicities and in vitro expression levels of recombinant modified vaccinia virus Ankara HIV vaccines. Vaccine 26:486-93.
102. Wyatt, L. S., S. T. Shors, B. R. Murphy, and B. Moss. 1996. Development of a replication-deficient recombinant vaccinia virus vaccine effective against parainfluenza virus 3 infection in an animal model. Vaccine 14:1451-58.
103. Wyatt, L. S., Earl, P. L., Liu, J. Y., Smith, J. M., Montefiori, D. C., Robinson, H. L., Moss, B., 2004. Multiprotein HIV type 1 clade B DNA and MVA vaccines: construction, expression, and immunogenicity in rodents of the MVA component. AIDS Res. Hum. Retrovir. 20:645-653.
104. Wyatt L S, Earl P L, Xiao W, Americo J L, Cotter C A, Vogt J, et al. Elucidating and minimizing the loss by recombinant vaccinia virus of human immunodeficiency virus gene expression resulting from spontaneous mutations and positive selection. J Virol 2009; 83(14):7176-84.
105. Yue, Y., Kaur, A., Eberhardt, M. K., Kassis, N., Zhou, S. S., Tarantal, A. F., Barry, P. A., 2007. Immunogenicity and protective efficacy of DNA vaccines expressing rhesus cytomegalovirus glycoprotein B, phosphoprotein 65-2, and viral interleukin-10 in rhesus macaques. J. Virol. 81:1095-1109.
106. Yue, Y., Wang, Z., Abel, K., Li, J., Strelow, L., Mandarino, A., Eberhardt, M. K., Schmidt, K. A., Diamond, D. J., Barry, P. A., 2008. Evaluation of recombinant modified vaccinia Ankara virus-based rhesus cytomegalovirus vaccines in rhesus macaques. Med. Microbiol. Immunol. 197:117-123.
107. Zaia, J. A., Sissons, J. G., Riddell, S. R., and Diamond, D. J., 2001. Status of cytomegalovirus prevention and treatment in 2000. Hematology 2000:339-355.
108. Zaia, J. A., 2002. Prevention and management of CMV-related problems after hematopoietic stem cell transplantation. Bone Marrow Transplant. 29:633-638.
109. Zhang, X., Cassis-Ghavami, F., Eller, M., Currier, J., Slike, B. M., Chen, X., Tartaglia, J., Marovich, M., Spearman, P., 2007. Direct comparison of antigen production and induction of apoptosis by canarypox virus- and modified vaccinia virus Ankara human immunodeficiency virus vaccine vectors. J. Virol. 81:7022-7033.

What is claimed is:

1. A method of controlling or treating a cytomegalovirus (CMV) infection in a subject comprising:
   administering to a subject in need thereof, a composition comprising an immunologically effective amount of a recombinant modified vaccinia Ankara (rMVA) virus, wherein the rMVA virus comprises a fusion nucleotide sequence which comprises SEQ ID NO: 11, and which encodes an IEfusion CMV protein antigen, said fusion nucleotide sequence comprising a nucleotide sequence encoding an Immediate-Early Gene-1 (IE1) antigenic portion directly fused to a nucleotide sequence encoding an Immediate-Early Gene-2 (IE2) antigenic portion, wherein
   (i) the nucleotide sequence encoding the IE1 antigenic portion includes a nucleotide sequence encoding IE1 exon 4 (IE1/e4);
   (ii) the nucleotide sequence encoding the IE2 antigenic portion is a nucleotide sequence encoding IE2 exon 5 (IE2/e5); or
   (iii) both (i) and (ii), thereby controlling or treating the CMV infection in the subject.

2. The method of claim 1, wherein the composition further comprises a nucleotide sequence which encodes at least one CMV antigen or a combination of antigens selected from the group consisting of HCMV-pp65, and glycoprotein B (gB).

3. The method of claim 1, wherein the rMVA virus is genetically stable and maintains immunogenicity after serial passage, and wherein the DNA sequence of the IE1 or IE2 gene and the expression of the IE1 or IE2 gene is substantially unchanged over the time of serial passage.

4. A method of controlling or treating a cytomegalovirus (CMV) infection in a subject comprising:
   administering to a subject in need thereof, a composition comprising: an immunologically effective amount of a recombinant modified vaccinia Ankara (rMVA) virus, wherein the rMVA virus comprises a fusion nucleotide sequence, which comprises SEQ ID NO: 11, and which encodes an IEfusion CMV protein antigen, said fusion nucleotide sequence comprising a nucleotide sequence encoding an Immediate-Early Gene-1 (IE1) antigenic portion directly fused to a nucleotide sequence encoding an Immediate-Early Gene-2 (IE2) antigenic portion, wherein
   (i) the nucleotide sequence encoding the IE1 antigenic portion includes a nucleotide sequence encoding IE1 exon 4 (IE1/e4);
   (ii) the nucleotide sequence encoding the IE2 antigenic portion is a nucleotide sequence encoding IE2 exon 5 (IE2/e5); or
   (iii) both (i) and (ii), thereby controlling or treating the CMV infection in the subject,
   wherein the composition is produced by:
   a) constructing a transfer plasmid vector comprising a modified H5 (mH5) promoter operably linked to a DNA sequence encoding the IEfusion CMV protein antigen, wherein the expression of said DNA sequence is under the control of the mH5 promoter;
   b) generating the rMVA virus by transfecting one or more plasmid vectors obtained from step a) into cells infected with wild type MVA;
   c) identifying rMVA virus expressing one or more of the IEfusion CMV protein antigens using one or more selection methods for serial passage;
   d) conducting serial passage;
   e) expanding an rMVA virus strain identified by step d); and
   f) purifying the rMVA virus strain from step e) to form the composition.

5. The method of claim 4, wherein the identification of rMVA virus carrying the transfer vector is accomplished by one or more gene-in selection methods, one or more gene-out selection methods, or a combination of gene-in and gene-out selection methods.

6. The method of claim 4, wherein the serial passage is at least 10 passages.

7. The method of claim 4, wherein the transfer plasmid vector further comprises the nucleotide sequence of SEQ ID NO:10.

8. The method of claim 4, wherein the transfer plasmid comprises nucleotide sequences SEQ ID NO:9 and SEQ ID NO:10.

9. The method of claim 1, wherein an immune response in the subject is modified.

10. The method of claim 9, wherein the subject is a human.

11. The method of claim 9, wherein the subject is a human stem cell donor or a human solid organ transplant donor.

12. The method of claim 9, wherein the subject is a human with an immunodeficiency disease selected from the group consisting of HIV and a heritable immunodeficiency and the subject is susceptible to infection by human cytomegalovirus.

13. The method of claim 9, wherein the subject is a human subject who has received a stem cell transplant or a solid organ transplant from a healthy donor.

* * * * *

UNITED STATES PATENT AND TRADEMARK OFFICE
CERTIFICATE OF CORRECTION

| | | |
|---|---|---|
| PATENT NO. | : 10,603,375 B2 | Page 1 of 1 |
| APPLICATION NO. | : 15/589857 | |
| DATED | : March 31, 2020 | |
| INVENTOR(S) | : Diamond et al. | |

It is certified that error appears in the above-identified patent and that said Letters Patent is hereby corrected as shown below:

In the Specification

In the Statement Regarding Federally Sponsored Research section, Column 1, Lines 21-26, please delete:
"The invention was made with Government support under Grant No. CA030206 awarded by the Public Health Service, Grant Nos. CA077544 and CA114889 awarded by the National Cancer Institute and Grant No. AI062496 awarded by the National Institute of Allergy and Infectious Disease. The Government has certain rights in the invention."
And replace with:
--This invention was made with government support under R01 CA030206, R01 CA114889, R01 CA077544, and R01 AI062496 awarded by the National Institutes of Health. The government has certain rights in the invention.--

Signed and Sealed this
Fifth Day of September, 2023

Katherine Kelly Vidal
*Director of the United States Patent and Trademark Office*

SEQUENCE LISTING

```
<160> NUMBER OF SEQ ID NOS: 18

<210> SEQ ID NO 1
<211> LENGTH: 22
<212> TYPE: DNA
<213> ORGANISM: Artificial Sequence
<220> FEATURE:
<223> OTHER INFORMATION: pp65 forward primer

<400> SEQUENCE: 1
atcaaaccgg gcaagatctc gc                                            22

<210> SEQ ID NO 2
<211> LENGTH: 22
<212> TYPE: DNA
<213> ORGANISM: Artificial Sequence
<220> FEATURE:
<223> OTHER INFORMATION: pp65 reverse primer

<400> SEQUENCE: 2
atcgtactga cgcagttcca cg                                            22
```

<210> SEQ ID NO 3
<211> LENGTH: 20
<212> TYPE: DNA
<213> ORGANISM: Artificial Sequence
<220> FEATURE:
<223> OTHER INFORMATION: IE1 exon4 forward primer

<400> SEQUENCE: 3
ccatcgccga ggagtcagat                                          20

<210> SEQ ID NO 4
<211> LENGTH: 20
<212> TYPE: DNA
<213> ORGANISM: Artificial Sequence
<220> FEATURE:
<223> OTHER INFORMATION: IE1 exon4 reverse primer

<400> SEQUENCE: 4
agtgtcctcc cgctcctcct                                          20

<210> SEQ ID NO 5
<211> LENGTH: 20
<212> TYPE: DNA
<213> ORGANISM: Artificial Sequence
<220> FEATURE:
<223> OTHER INFORMATION: IEfusion forward primer

<400> SEQUENCE: 5
aagttgcccc agaggaagag                                          20

<210> SEQ ID NO 6
<211> LENGTH: 20
<212> TYPE: DNA
<213> ORGANISM: Artificial Sequence
<220> FEATURE:
<223> OTHER INFORMATION: IEfusion reverse primer

<400> SEQUENCE: 6
ctgctaacgc tgcaagagtg                                          20

<210> SEQ ID NO 7
<211> LENGTH: 21
<212> TYPE: DNA
<213> ORGANISM: Artificial Sequence
<220> FEATURE:
<223> OTHER INFORMATION: TK forward primer

<400> SEQUENCE: 7
tgtgagcgta tggcaaacga a                                        21

<210> SEQ ID NO 8
<211> LENGTH: 28
<212> TYPE: DNA
<213> ORGANISM: Artificial Sequence
<220> FEATURE:
<223> OTHER INFORMATION: TK reverse primer

<400> SEQUENCE: 8
tcgatgtaac actttctaca caccgatt                                 28

<210> SEQ ID NO 9
<211> LENGTH: 9388
<212> TYPE: DNA
<213> ORGANISM: Artificial Sequence
<220> FEATURE:
<223> OTHER INFORMATION: mH5-IEfusion-pZWIIA (GUS) plasmid DNA sequence

<400> SEQUENCE: 9

```
cctcctgaaa aactggaatt taatacacca tttgtgttca tcatcagaca tgatattact      60
ggatttatat tgtttatggg taaggtagaa tctccttaat atgggtacgg tgtaaggaat     120
cattatttta tttatattga tgggtacgtg aaatctgaat tttcttaata aatattattt     180
ttattaaatg tgtatatgtt gttttgcgat agccatgtat ctactaatca gatctattag     240
agatattatt aattctggtg caatatgaca aaaattatac actaattagc gtctcgtttc     300
agacatggat ctgtcacgaa ttaatacttg aagtctaag cagctgaaaa gctttctctc      360
tagcaaagat gcatttaagg cggatgtcca tggacatagt gccttgtatt atgcaatagc     420
tgataataac gtgcgtctag tatgtacgtt gttgaacgct ggagcattga aaaatcttct     480
agagaatgaa tttccattac atcaggcagc cacattggaa gataccaaaa tagtaaagat     540
tttggctatt cagtggactg atgattcga ggtaccgact attgttctat attatatatg      600
gttgttgatg gatctgtgat gcatgcaata gctgataata gaacttacgc aaatattagc     660
aaaaatatat tagacaatac tacaattaac gatgagtgta gatgctgtta ttttgaacca     720
cagattagga ttcttgatag agatgagatg ctcaatggat catcgtgtga tatgaacaga     780
cattgtatta tgatgaattt acctgatgta ggcgaatttg gatctagtat gttggggaaa     840
tatgaacctg acatgattaa gattgctctt tcggtggctg ggtaccaggc gcgcatttca     900
ttttgttttt ttctatgcta taaatggtac gtcctgtaga accccaacc cgtgaaatca      960
aaaaactcga cggcctgtgg gcattcagtc tggatcgcga aaactgtgga attgatcagc    1020
gttggtggga agcgcgtta caagaaagcc gggcaattgc tgtgccaggc agttttaacg    1080
atcagttcgc cgatgcagat attcgtaatt atgcgggcaa cgtctggtat cagcgcgaag    1140
tctttatacc gaaaggttgg gcaggccagc gtatcgtgct gcgtttcgat gcggtcactc    1200
attacggcaa agtgtgggtc aataatcagg aagtgatgga gcatcaggg ggctatacgc     1260
catttgaagc cgatgtcacg ccgtatgtta ttgccgggaa aagtgtacgt atcaccgttt    1320
gtgtgaacaa cgaactgaac tggcagacta tcccgccggg aatggtgatt ccgacgaaa     1380
acggcaagaa aaagcagtct tacttccatg atttctttaa ctatgccgga atccatcgca    1440
gcgtaatgct ctacaccacg ccgaacacct gggtggacga tatcaccgtg gtgacgcatg    1500
tcgcgcaaga ctgtaaccac gcgtctgttg actggcaggt ggtggccaat ggtgatgtca    1560
gcgttgaact gcgtgatgcg gatcaacagg tggttgcaac tggacaaggc actagcggga    1620
ctttgcaagt ggtgaatccg cacctctggc aaccgggtga aggttatctc tatgaactgt    1680
gcgtcacagc caaaagccag acagagtgtg atatctaccc gcttcgcgtc ggcatccggt    1740
cagtggcagt gaagggcgaa cagttcctga ttaaccacaa accgttctac tttactggct    1800
ttggtcgtca tgaagatgcg gacttgcgtg gcaaaggatt cgataacgtg ctgatggtgc    1860
acgaccacgc attaatggac tggattgggg ccaactccta ccgtacctcg cattacccct    1920
acgctgaaga gatgctcgac tgggcagatg aacatggcat cgtggtgatt gatgaaactg    1980
ctgctgtcgg ctttaacctc tctttaggca ttggtttcga agcgggcaac aagccgaaag    2040
aactgtacag cgaagaggca gtcaacgggg aaactcagca agcgcactta caggcgatta    2100
aagagctgat agcgcgtgac aaaaaccacc caagcgtggt gatgtggagt attgccaacg    2160
aaccggatac ccgtccgcaa ggtgcacggg aatatttcgc gccactggcg gaagcaacgc    2220
gtaaactcga cccgacgcgt ccgatcacct gcgtcaatgt aatgttctgc gacgctcaca    2280
```

```
ccgataccat cagcgatctc tttgatgtgc tgtgcctgaa ccgttattac ggatggtatg    2340
tccaaagcgg cgatttggaa acggcagaga aggtactgga aaaagaactt ctggcctggc    2400
aggagaaact gcatcagccg attatcatca ccgaatacgg cgtggatacg ttagccgggc    2460
tgcactcaat gtacaccgac atgtggagtg aagagtatca gtgtgcatgg ctggatatgt    2520
atcaccgcgt ctttgatcgc gtcagcgccg tcgtcggtga acaggtatgg aatttcgccg    2580
attttgcgac ctcgcaaggc atattgcgcg ttggcggtaa caagaaaggg atcttcactc    2640
gcgaccgcaa accgaagtcg gcggcttttc tgctgcaaaa acgctggact ggcatgaact    2700
tcggtgaaaa accgcagcag ggaggcaaac aatgagagct cggttgttga tggatctgtg    2760
atgcatgcaa tagctgataa tagaacttac gcaaatatta gcaaaaatat attagacaat    2820
actacaatta acgatgagtg tagatgctgt tattttgaac cacagattag gattcttgat    2880
agagatgaga tgctcaatgg atcatcgtgt gatatgaaca gacattgtat tatgatgaat    2940
ttacctgatg taggcgaatt tggatctagt atgttgggga aatatgaacc tgacatgatt    3000
aagattgctc tttcggtggc tggcggcccg ctcgagaaaa attgaaaata aatacaaagg    3060
ttcttgaggg ttgtgttaaa ttgaaagcga gaaataatca taaataagcc accaccgttt    3120
aaacgccacc acaatggtca aacagattaa ggttcgagtg gacatggtgc ggcatagaat    3180
caaggagcac atgctgaaaa aatatacccca gacggaagag aaattcactg gcgcctttaa    3240
tatgatggga ggatgtttgc agaatgcctt agatatctta gataaggttc atgagccttt    3300
cgaggagatg aagtgtattg ggctaactat gcagagcatg tatgagaact acattgtacc    3360
tgaggataag cgggagatgt ggatggcttg tattaaggag ctgcatgatg tgagcaaggg    3420
cgccgctaac aagttggggg gtgcactgca ggctaaggcc cgtgctaaaa aggatgaact    3480
taggagaaag atgatgtata tgtgctacag gaatatagag ttctttacca agaactcagc    3540
cttccctaag accaccaatg gctgcagtca ggccatggcg gcactgcaga acttgcctca    3600
gtgctcccct gatgagatta tggcttatgc ccagaaaata tttaagattt tggatgagga    3660
gagagacaag gtgctcacgc acattgatca catatttatg gatatcctca ctacatgtgt    3720
ggaaacaatg tgtaatgagt acaaggtcac tagtgacgct tgtatgatga ccatgtacgg    3780
gggcatctct ctcttaagtg agttctgtcg ggtgctgtgc tgctatgtct tagaggagac    3840
tagtgtgatg ctggccaagc ggcctctgat aaccaagcct gaggttatca gtgtaatgaa    3900
gcgccgcatt gaggagatct gcatgaaggt ctttgcccag tacattctgg gggccgatcc    3960
tctgagagtc tgctctccta gtgtggatga cctacgggcc atcgccgagg agtcagatga    4020
ggaagaggct attgtagcct acactttggc caccgctggt gtcagctcct ctgattctct    4080
ggtgtcaccc ccagagtccc ctgtaccccgc gactatccct ctgtcctcag taattgtggc    4140
tgagaacagt gatcaggaag aaagtgagca gagtgatgag gaagaggagg agggtgctca    4200
ggaggagcgg gaggacactg tgtctgtcaa gtctgagcca gtgtctgaga tagaggaagt    4260
tgccccagag gaagaggagg atggtgctga ggaacccacc gcctctggag caagagcac    4320 ccacccctatg gtgactagaa gcaaggctga ccagggtgac atcctcgccc aggctgtcaa    4380
tcatgccggt atcgattcca gtagcaccgg ccccacgctg acaacccact cttgcagcgt    4440
tagcagcgcc cctcttaaca agccgacccc caccagcgtc gcggttacta acactcctct    4500
ccccggggca tccgctactc ccgagctcag cccgcgtaag aaaccgcgca aaaccacgcg    4560 tccttttcaag gtgattatta aaccgcccgt gcctcccgcg cctatcatgc tgcccctcat    4620
caaacaggaa gacatcaagc ccgagcccga ctttaccatc cagtaccgca acaagattat    4680
```

```
cgataccgcc ggctgtatcg tgatctctga tagcgaggaa gaacagggtg aagaagtcga    4740
aacccgcggt gctaccgcgt cttcccttc caccggcagc ggcacgccgc gagtgacctc    4800
tcccacgcac ccgctctccc agatgaacca ccctcctctt cccgatccct tgggccggcc    4860
cgatgaagat agttcctctt cgtcttcctc ctcctgcagt tcggcttcgg actcggagag    4920
tgagtccgag gagatgaaat gcagcagtgg cggaggagca tccgtgacct cgagccacca    4980
tgggcgcggc ggttttggtg gcgcggcctc ctcctctctg ctgagctgcg gccatcagag    5040
cagcggcggg gcgagcaccg gaccccgcaa gaagaagagc aaacgcatct ccgagttgga    5100
caacgagaag gtgcgcaata tcatgaaaga taagaacacc cccttctgca cacccaacgt    5160
gcagactcgg cggggtcgcg tcaagattga cgaggtgagc cgcatgttcc gcaacaccaa    5220
tcgctctctt gagtacaaga acctgcccct cacgattccc agtatgcacc aggtgttaga    5280
tgaggccatc aaagcctgca aaaccatgca ggtgaacaac aagggcatcc agattatcta    5340
cacccgcaat catgaggtga agagtgaggt ggatgcggtg cggtgtcgcc tgggcaccat    5400
gtgcaacctg gccctctcca ctcccttcct catggagcac accatgcccg tgacacatcc    5460
acccgaagtg gcgcagcgca cagccgatgc ttgtaacgaa ggcgtcaagg ccgcgtggag    5520
cctcaaagaa ttgcacaccc accaattatg ccccgttcc tccgattacc gcaacatgat    5580
catccacgct gccaccccg tggacctgtt gggcgctctc aacctgtgcc tgccctgat    5640 gcaaaagtt cccaaacagg tcatggtgcg catcttctcc accaaccagg gtgggttcat    5700
gctgcctatc tacgagacgg ccgcgaaggc ctacgccgtg gggcagtttg agcagcccac    5760
cgagacccct cccgaagacc tggacaccct gagcctggcc atcgaggcag ccatccagga    5820
cctgaggaac aagtctcagt aaaataaagg cgcgccataa aaattttat actagtgtac    5880 cgcggtcgaa tcgatttaat taacgatgct agcattgtcg acggtggtgg gcggccgcc    5940 agtgtgatgg atatctgcag aattcggctt ggggggctgc aggtggatgc gatcatgacg    6000
tcctctgcaa tggataacaa tgaacctaaa gtactagaaa tggtatatga tgctacaatt    6060
ttacccgaag gtagtagcat ggattgtata acagacaca tcaatatgtg tatacaacgc    6120
acctatagtt ctagtataat tgccatattg gatagattcc taatgatgaa caaggatgaa    6180
ctaaataata cacagtgtca tataattaaa gaatttatga catacgaaca aatggcgatt    6240
gaccattatg gagaatatgt aaacgctatt ctatatcaaa ttcgtaaaag acctaatcaa    6300
catcacacca ttaatctgtt taaaaaaata aaagaaccc ggtatgacac ttttaaagtg    6360
gatcccgtag aattcgtaaa aaagttatc ggatttgtat ctatcttgaa caaatataaa    6420
ccggtttata gttacgtcct gtacgagaac gtcctgtacg atgagttcaa atgtttcatt    6480
gactacgtgg aaactaagta tttctaaaat taatgatgca ttaattttg tattgattct    6540 caatcctaaa aactaaaata tgaataagta ttaaacatag cggtgtacta attgatttaa    6600
cataaaaaat agttgttaac taatcatgag gactctactt attagatata ttctttggag    6660
aaatgacaac gatcaaaccg ggcatgcaag cttgtctccc tatagtgagt cgtattagag    6720
cttggcgtaa tcatggtcat agctgtttcc tgtgtgaaat tgttatccgc tcacaattcc    6780
acacaacata cgagccggaa gcataaagtg taaagcctgg ggtgcctaat gagtgagcta    6840
actcacatta attgcgttgc gctcactgcc cgctttcgag tcggaaaacc tgtcgtgcca    6900
gctgcattaa tgaatcggcc aacgcgcggg gagaggcggt ttgcgtattg ggcgctcttc    6960
cgcttcctcg ctcactgact cgctgcgctc ggtcgttcgg ctgcggcgag cggtatcagc    7020
```

```
tcactcaaag gcggtaatac ggttatccac agaatcaggg gataacgcag gaaagaacat    7080
gtgagcaaaa ggccagcaaa aggccaggaa ccgtaaaaag gccgcgttgc tggcgttttt    7140
cgataggctc cgcccccctg acgagcatca caaaaatcga cgctcaagtc agaggtggcg    7200
aaacccgaca ggactataaa gataccaggc gtttccccct ggaagctccc tcgtgcgctc    7260
tcctgttccg accctgccgc ttaccggata cctgtccgcc tttctccctt cgggaagcgt    7320
ggcgctttct catagctcac gctgtaggta tctcagttcg gtgtaggtcg ttcgctccaa    7380
gctgggctgt gtgcacgaac cccccgttca gcccgaccgc tgcgccttat ccggtaacta    7440
tcgtcttgag tccaacccgg taagacacga cttatcgcca ctggcagcag ccactggtaa    7500
caggattagc agagcgaggt atgtaggcgg tgctacagag ttcttgaagt ggtggcctaa    7560
ctacggctac actagaagga cagtatttgg tatctgcgct ctgctgaagc cagttacctt    7620
cggaaaaaga gttggtagct cttgatccgg caaacaaacc accgctggta gcggtggttt    7680
ttttgtttgc aagcagcaga ttacgcgcag aaaaaaagga tctcaagaag atcctttgat    7740
cttttctacg gggtctgacg ctcagtggaa cgaaaactca cgttaaggga ttttggtcat    7800
gagattatca aaaaggatct tcacctagat ccttttaaat taaaaatgaa gttttaaatc    7860
aatctaaagt atatatgagt aaacttggtc tgacagttac caatgcttaa tcagtgaggc    7920
acctatctca gcgatctgtc tatttcgttc atccatagtt gcctgactcc ccgtcgtgta    7980
gataactacg atacgggagg gcttaccatc tggccccagt gctgcaatga taccgcgaga    8040
cccacgctca ccggctccag atttatcagc aataaaccag ccagccggaa gggccgagcg    8100
cagaagtggt cctgcaactt tatccgcctc catccagtct attaattgtt gccgggaagc    8160
tagagtaagt agttcgccag ttaatagttt cgcaacgtt gttggcattg ctacaggcat    8220
cgtggtgtca cgctcgtcgt ttggtatggc ttcattcagc tccggttccc aacgatcaag    8280
gcgagttaca tgatccccca tgttgtgcaa aaaagcggtt agctccttcg gtcctccgat    8340
cgttgtcaga agtaagttgg ccgcagtgtt atcactcatg gttatggcag cactgcataa    8400
ttctcttact gtcatgccat ccgtaagatg cttttctgtg actggtgagt actcaaccaa    8460
gtcattctga gaatagtgta tgcggcgacc gagttgctct tgcccggcgt caatacggga    8520
taataccgcg ccacatagca gaactttaaa agtgctcatc attggaaaac gttcttcggg    8580
gcgaaaactc tcaaggatct taccgctgtt gagatccagt tcgatgtaac ccactcgtgc    8640
acccaactga tcttcagcat cttttacttt caccagcgtt tctgggtgag caaaaacagg    8700
aaggcaaaat gccgcaaaaa agggaataag ggcgacacgg aaatgttgaa tactcatact    8760
cttcctttt caatattatt gaagcattta tcagggttat tgtctcatga gcggatacat    8820
atttgaatgt atttagaaaa ataaacaaat aggggttccg cgcacatttc cccgaaaagt    8880
gccacctgac gtctaagaaa ccattattat catgacatta acctataaaa ataggcgtat    8940
cacgaggccc tttcgtctcg cgcgtttcgg tgatgacggt gaaaacctct gacacatgca    9000
gctcccggag acgtcacag cttgtctgta agcggatgcc gggagcagac aagcccgtca    9060
gggcgcgtca gcgggtgttg gcgggtgtcg ggctggctt aactatgcgg catcagagca    9120
gattgtactg agagtgcacc atatgcggtg tgaaataccg cacagatgcg taaggagaaa    9180
ataccgcatc aggcgccatt cgccattcag gctgcgcaac tgttgggaag ggcgatcggt    9240
gcgggcctct tcgctattac gccagctggc gaaaggggga tgtgctgcaa ggcgattaag    9300
ttgggtaacg ccagggtttt cccagtcacg acgttgtaaa acgacggcca gtgaattgga    9360
tttaggtgac actatagaat acgaattc                                        9388
```

<210> SEQ ID NO 10
<211> LENGTH: 8152
<212> TYPE: DNA
<213> ORGANISM: Artificial Sequence
<220> FEATURE:
<223> OTHER INFORMATION: mH5-pp65-GUS-pLW51(GUS) plasmid DNA sequence

<400> SEQUENCE: 10

```
gaattcgttg gtggtcgcca tgatggtgt tattgtatac tgtctaaacg cgttagtaaa      60
acatggcgag gaaataaatc atataaaaaa tgatttcatg attaaaccat gttgtgaaaa    120
agtcaagaac gttcacattg gcggacaatc taaaaacaat acagtgattg cagatttgcc    180
atatatggat aatgcggtat ccgatgtatg caattcactg tataaaaaga atgtatcaag    240
aatatccaga tttgctaatt tgataaagat agatgacgat gacaagactc ctactggtgt    300
atataattat tttaaaccta agatgccat tcctgttatt atatccatag aaaggatag     360
agatgtttgt gaactattaa tctcatctga taaagcgtgt gcgtgtatag agttaaattc    420
atataaagta gccattcttc ccatggatgt ttccttttt accaaaggaa atgcatcatt    480
gattattctc ctgttttgatt tctctatcga tgcggcacct ctcttaagaa gtgtaaccga    540
taataatgtt attatatcta gacaccagcg tctacatgac gagcttccga gttccaattg    600
gttcaagttt tacataagta taagtccga ctattgttct atattatata tggttgttga    660
tggatctgtg atgcatgcaa tagctgataa tagaacttac gcaaatatta gcaaaaatat    720
attagacaat actacaatta acgatgagtg tagatgctgt tattttgaac cacagattag    780
gattcttgat agagatgaga tgctcaatgg atcatcgtgt gatatgaaca gacattgtat    840
tatgatgaat ttacctgatg taggcgaatt tggatctagt atgttgggga aatatgaacc    900
tgacatgatt aagattgctc tttcggtggc tgggtaccag gcgcgcattt cattttgtt    960
ttttctatgc tataaatggt acgtcctgta gaaaccccaa cccgtgaaat caaaaaactc   1020
gacggcctgt gggcattcag tctggatcgc gaaaactgtg aattgatca gcgttggtgg   1080
gaaagcgcgt tacaagaaag ccgggcaatt gctgtgccag gcagttttaa cgatcagttc   1140
gccgatgcag atattcgtaa ttatgcgggc aacgtctggt atcagcgcga agtctttata   1200
ccgaaaggtt gggcaggcca gcgtatcgtc tgcgtttcg atgcggtcac tcattacggc   1260
aaagtgtggg tcaataatca ggaagtgatg gagcatcagg gcggctatac gccatttgaa   1320
gccgatgtca cgccgtatgt tattgccggg aaaagtgtac gtatcaccgt ttgtgtgaac   1380
aacgaactga actggcagac tatcccgccg ggaatggtga ttaccgacga aaacggcaag   1440
aaaaagcagt cttacttcca tgatttcttt aactatgccg gaatccatcg cagcgtaatg   1500
ctctacacca cgccgaacac ctgggtggac gatatcaccg tggtgacgca tgtcgcgcaa   1560
gactgtaacc acgcgtctgt tgactggcag gtggtggcca atggtgatgt cagcgttgaa   1620
ctgcgtgatg cggatcaaca ggtggttgca actggacaag cactagcgg actttgcaa    1680
gtggtgaatc cgcacctctg caaccgggt gaaggttatc tctatgaact gtgcgtcaca   1740
gccaaaagcc agacagagtg tgatatctac ccgcttcgcg tcggcatccg tcagtggca    1800
gtgaagggcg aacagttcct gattaaccac aaaccgttct actttactgg ctttggtcgt   1860
catgaagatg cggacttgcg tggcaaagga ttcgataacg tgctgatggt gcacgaccac   1920
gcattaatgg actggattgg ggccaactcc taccgtacct cgcattaccc ttacgctgaa   1980
gagatgctcg actgggcaga tgaacatggc atcgtggtga ttgatgaaac tgctgctgtc   2040
```

```
ggctttaacc tctctttagg cattggtttc gaagcgggca acaagccgaa agaactgtac   2100
agcgaagagg cagtcaacgg ggaaactcag caagcgcact tacaggcgat taaagagctg   2160
atagcgcgtg acaaaaacca cccaagcgtg gtgatgtgga gtattgccaa cgaaccggat   2220
acccgtccgc aaggtgcacg ggaatatttc gcgccactgg cggaagcaac gcgtaaactc   2280
gacccgacgc gtccgatcac ctgcgtcaat gtaatgttct gcgacgctca caccgatacc   2340
atcagcgatc tctttgatgt gctgtgcctg aaccgttatt acggatggta tgtccaaagc   2400
ggcgatttgg aaacggcaga aaggtactg gaaaagaac ttctggcctg gcaggagaaa   2460
ctgcatcagc cgattatcat caccgaatac ggcgtggata cgttagccgg gctgcactca   2520
atgtacaccg acatgtggag tgaagagtat cagtgtgcat ggctggatat gtatcaccgc   2580
gtctttgatc gcgtcagcgc cgtcgtcggt gaacaggtat ggaatttcgc cgattttgcg   2640
acctcgcaag gcatattgcg cgttggcggt aacaagaaag ggatcttcac tcgcgaccgc   2700
aaaccgaagt cggcggcttt tctgctgcaa aaacgctgga ctggcatgaa cttcggtgaa   2760
aaaccgcagc agggaggcaa acaatgagag ctcggttgtt gatggatctg tgatgcatgc   2820
aatagctgat aatagaactt acgcaaatat tagcaaaaat atattagaca atactacaat   2880
taacgatgag tgtagatgct gttatttga accacagatt aggattcttg atagagatga   2940
gatgctcaat ggatcatcgt gtgatatgaa cagacattgt attatgatga atttacctga   3000
tgtaggcgaa tttggatcta gtatgttggg gaaatatgaa cctgacatga ttaagattgc   3060
tctttcggtg gctggcggcc cgctcgagaa aaattgaaaa taaatacaaa ggttcttgag   3120
ggttgtgtta aattgaaagc gagaaataat cataaataag ccaccaccgt ttaaacagtc   3180
gacggtatcg ataagcttga tatcgaattc ctgcagcccg tacgcgcagg cagcatggag   3240
tcgcgcggtc gccgttgtcc cgaaatgata tccgtactgg gtcccatttc ggggcacgtg   3300
ctgaaagccg tgtttagtcg cggcgacacg ccggtgctgc cgcacgagac gcgactcctg   3360
cagacgggta tccacgtgcg cgtgagccag ccctcgctga tcctggtgtc gcagtacacg   3420
cccgactcga cgccatgcca ccgcggcgac aatcagctgc aggtgcagca cacgtacttt   3480
acgggcagcg aggtggagaa cgtgtcggtc aacgtgcaca accccacggg ccggagcatc   3540
tgccccagcc aagagcccat gtcgatctat gtgtacgcgc tgccgctcaa gatgctgaac   3600
atccccagca tcaacgtgca ccactacccg tcggcggccg agcgcaaaca ccgacacctg   3660
cccgtagctg acgctgtgat tcacgcgtcg ggcaagcaga tgtggcaggc gcgtctcacg   3720
gtctcgggac tggcctggac gcgtcagcag aaccagtgga agagcccga cgtctactac   3780 acgtcagcgt tcgtgtttcc caccaaggac gtggcactgc ggcacgtggt gtgcgcgcac   3840
gagctggttt gctccatgga gaacacgcgc gcaaccaaga tgcaggtgat aggtgaccag   3900
tacgtcaagg tgtacctgga gtccttctgc gaggacgtgc cctccggcaa gctctttatg   3960
cacgtcacgc tgggctctga cgtggaagag gacctgacga tgacccgcaa cccgcaaccc   4020
ttcatgcgcc cccacgagcg caacggcttt acggtgttgt gtcccaaaaa tatgataatc   4080
aaaccgggca agatctcgca catcatgctg gatgtggctt ttacctcaca cgagcatttt   4140
gggctgctgt gtcccaagag catcccgggc ctgagcatct caggtaacct attgatgaac   4200
gggcagcaga tcttcctgga ggtgcaagcg atacgcgaga ccgtggaact gcgtcagtac   4260
gatcccgtgg ctgcgctctt cttttttcgat atcgacttgc tgctgcagcg cgggcctcag   4320
tacagcgaac ccccaccctt caccagccag tatcgcatcc agggcaagct tgagtaccga   4380
cacacctggg accggcacga cgagggtgcc gcccagggcg acgacgacgt ctggaccagc   4440
```

```
ggatcggact ccgacgagga actcgtaacc accgagcgca agacgccccg cgttaccggc   4500
ggcggcgcca tggcgggcgc ctccacttcc gcgggccgca aacgcaaatc agcatcctcg   4560
gcgacggcgt gcacggcggg cgttatgaca cgcggccgcc ttaaggccga gtccaccgtc   4620
gcgcccgaag aggacaccga cgaggattcc gacaacgaaa tccacaatcc ggccgtgttc   4680
acctggccgc cctggcaggc cggcatcctg gcccgcaacc tggtgcccat ggtggctacg   4740
gttcagggtc agaatctgaa gtaccaggag ttcttctggg acgccaacga catctaccgc   4800
atcttcgccg aattggaagg cgtatggcag cccgctgcgc aacccaaacg tcgccgccac   4860
cggcaagacg ccttgcccgg gccatgcatc gcctcgacgc ccaaaaagca ccgaggttga   4920
tttttatggc gcgccctgca gggaaagttt tataggtagt tgatagaaca aaatacataa   4980
ttttgtaaaa ataaatcact ttttatacta atatgacacg attaccaata cttttgttac   5040
taatatcatt agtatacgct acacctttc ctcagacatc taaaaaaata ggtgatgatg   5100
caactttatc atgtaatcga aataatacaa atgactacgt tgttatgagt gcttggtata   5160
aggagcccaa ttccattatt cttttagctg ctaaaagcga cgtcttgtat tttgataatt   5220
ataccaagga taaatatct tacgactctc catacgatga tctagttaca actatcacaa   5280
ttaaatcatt gactgctaga gatgccggta cttatgtatg tgcattcttt atgacatcgc   5340
ctacaaatga cactgataaa gtagattatg aagaatactc cacagagttg attgtaaata   5400
cagatagtga atcgactata gacataatac tatctggatc tacacattca ccagaaacta   5460
gttaagcttg tctccctata gtgagtcgta ttagagcttg gcgtaatcat ggtcatagct   5520
gtttcctgtg tgaaattgtt atccgctcac aattccacac aacatacgag ccggaagcat   5580
aaagtgtaaa gcctggggtg cctaatgagt gagctaactc acattaattg cgttgcgctc   5640
actgcccgct ttcgagtcgg gaaacctgtc gtgccagctg cattaatgaa tcggccaacg   5700
cgcggggaga ggcggtttgc gtattgggcg ctcttccgct tcctcgctca ctgactcgct   5760
gcgctcggtc gttcggctgc ggcgagcggt atcagctcac tcaaaggcgg taatacggtt   5820
atccacagaa tcaggggata acgcaggaaa gaacatgtga gcaaaaggcc agcaaaaggc   5880
caggaaccgt aaaaaggccg cgttgctggc gtttttcgat aggctccgcc cccctgacga   5940
gcatcacaaa aatcgacgct caagtcagag gtggcgaaac ccgacaggac tataaagata   6000
ccaggcgttt ccccctggaa gctccctcgt gcgctctcct gttccgaccc tgccgcttac   6060
cggatacctg tccgcctttc tcccttcggg aagcgtggcg ctttctcata gctcacgctg   6120
taggtatctc agttcggtgt aggtcgttcg ctccaagctg ggctgtgtgc acgaaccccc   6180
cgttcagccc gaccgctgcg ccttatccgg taactatcgt cttgagtcca acccggtaag   6240
acacgactta tcgccactgg cagcagccac tggtaacagg attagcagag cgaggtatgt   6300
aggcggtgct acagagttct tgaagtggtg gcctaactac ggctacacta aggacagt   6360 atttggtatc tgcgctctgc tgaagccagt taccttcgga aaagagttg gtagctcttg   6420 atccggcaaa caaaccaccg ctggtagcgg tggttttttt gtttgcaagc agcagattac   6480
gcgcagaaaa aaaggatctc aagaagatcc tttgatcttt tctacggggt ctgacgctca   6540
gtggaacgaa aactcacgtt aagggatttt ggtcatgaga ttatcaaaaa ggatcttcac   6600
ctagatcctt ttaaattaaa aatgaagttt taaatcaatc taagtatat atgagtaaac   6660 ttggtctgac agttaccaat gcttaatcag tgaggcacct atctcagcga tctgtctatt   6720
tcgttcatcc atagttgcct gactccccgt cgtgtagata actacgatac gggagggctt   6780
```

| | |
|---|---|
| accatctggc cccagtgctg caatgatacc gcgagaccca cgctcaccgg ctccagattt | 6840 |
| atcagcaata aaccagccag ccggaagggc gagcgcaga agtggtcctg caactttatc | 6900 |
| cgcctccatc cagtctatta attgttgccg ggaagctaga gtaagtagtt cgccagttaa | 6960 |
| tagtttgcgc aacgttgttg gcattgctac aggcatcgtg gtgtcacgct cgtcgtttgg | 7020 |
| tatggcttca ttcagctccg gttcccaacg atcaaggcga gttacatgat cccccatgtt | 7080 |
| gtgcaaaaaa gcggttagct ccttcggtcc tccgatcgtt gtcagaagta agttggccgc | 7140 |
| agtgttatca ctcatggtta tggcagcact gcataattct cttactgtca tgccatccgt | 7200 |
| aagatgcttt tctgtgactg gtgagtactc aaccaagtca ttctgagaat agtgtatgcg | 7260 |
| gcgaccgagt tgctcttgcc cggcgtcaat acgggataat accgcgccac atagcagaac | 7320 |
| tttaaaagtg ctcatcattg gaaaacgttc ttcggggcga aaactctcaa ggatcttacc | 7380 |
| gctgttgaga tccagttcga tgtaacccac tcgtgcaccc aactgatctt cagcatcttt | 7440 |
| tactttcacc agcgtttctg ggtgagcaaa aacaggaagg caaaatgccg caaaaaaggg | 7500 |
| aataagggcg acacggaaat gttgaatact catactcttc ctttttcaat attattgaag | 7560 |
| catttatcag ggttattgtc tcatgagcgg atacatattt gaatgtattt agaaaaataa | 7620 |
| acaaataggg gttccgcgca catttccccg aaaagtgcca cctgacgtct aagaaaccat | 7680 |
| tattatcatg acattaacct ataaaaatag gcgtatcacg aggccctttc gtctcgcgcg | 7740 |
| tttcggtgat gacggtgaaa acctctgaca catgcagctc ccggagacgg tcacagcttg | 7800 |
| tctgtaagcg gatgccggga gcagacaagc ccgtcagggc gcgtcagcgg gtgttggcgg | 7860 |
| gtgtcggggc tggcttaact atgcggcatc agagcagatt gtactgagag tgcaccatat | 7920 |
| gcggtgtgaa ataccgcaca gatgcgtaag gagaaaatac cgcatcaggc gccattcgcc | 7980 |
| attcaggctg cgcaactgtt gggaagggcg atcggtgcgg gcctcttcgc tattacgcca | 8040 |
| gctggcgaaa gggggatgtg ctgcaaggcg attaagttgg gtaacgccag ggttttccca | 8100 |
| gtcacgacgt tgtaaaacga cggccagtga attggattta ggtgacacta ta | 8152 |

<210> SEQ ID NO 11
<211> LENGTH: 2709
<212> TYPE: DNA
<213> ORGANISM: Artificial Sequence
<220> FEATURE:
<223> OTHER INFORMATION: HCMV IEfusion gene

<400> SEQUENCE: 11

| | |
|---|---|
| atggtcaaac agattaaggt tcgagtggac atggtgcggc atagaatcaa ggagcacatg | 60 |
| ctgaaaaaat atacccagac ggaagagaaa ttcactggcg cctttaatat gatgggagga | 120 |
| tgtttgcaga atgccttaga tatcttagat aaggttcatg agcctttcga ggagatgaag | 180 |
| tgtattgggc taactatgca gagcatgtat gagaactaca ttgtacctga ggataagcgg | 240 |
| gagatgtgga tggcttgtat taaggagctg catgatgtga gcaagggcgc cgctaacaag | 300 |
| ttgggggggtg cactgcaggc taaggcccgt gctaaaaagg atgaacttag agaaagatg | 360 |
| atgtatatgt gctacaggaa tatagagttc tttaccaaga actcagcctt ccctaagacc | 420 |
| accaatggct gcagtcaggc catggcggca ctgcagaact gcctcagtg ctcccctgat | 480 |
| gagattatgg cttatgccca gaaatatttt aagattttgg atgaggagag agacaaggtg | 540 |
| ctcacgcaca ttgatcacat atttatggat atcctcacta catgtgtgga aacaatgtgt | 600 |
| aatgagtaca aggtcactag tgacgcttgt atgatgacca tgtacggggg catctctctc | 660 |
| ttaagtgagt tctgtcgggt gctgtgctgc tatgtcttag aggagactag tgtgatgctg | 720 |

```
gccaagcggc tctctgataac caagcctgag gttatcagtg taatgaagcg ccgcattgag    780
gagatctgca tgaaggtctt tgcccagtac attctggggg ccgatcctct gagagtctgc    840
tctcctagtg tggatgacct acgggccatc gccgaggagt cagatgagga agaggctatt    900
gtagcctaca ctttggccac cgctggtgtc agctcctctg attctctggt gtcacccca     960 gagtccctg tacccgcgac tatccctctg tcctcagtaa ttgtggctga aacagtgat    1020 caggaagaaa gtgagcagag tgatgaggaa gaggaggagg tgctcagga ggagcgggag   1080 gacactgtgt ctgtcaagtc tgagccagtg tctgagatag aggaagttgc cccagaggaa   1140
gaggaggatg tgctgagga acccaccgcc tctggaggca agagcaccca ccctatggtg   1200
actagaagca aggctgacca gggtgacatc ctcgcccagg ctgtcaatca tgccggtatc   1260
gattccagta gcaccggccc cacgctgaca acccactctt gcagcgttag cagcgcccct   1320
cttaacaagc cgaccccac cagcgtcgcg gttactaaca ctcctctccc cggggcatcc    1380
gctactcccg agctcagccc gcgtaagaaa ccgcgcaaaa ccacgcgtcc tttcaaggtg   1440
attattaaac cgcccgtgcc tcccgcgcct atcatgctgc ccctcatcaa acaggaagac   1500
atcaagcccg agcccgactt taccatccag taccgcaaca agattatcga taccgccggc   1560
tgtatcgtga tctctgatag cgaggaagaa cagggtgaag aagtcgaaac ccgcggtgct   1620
accgcgtctt cccctcccac cggcagcggc acgccgcgag tgacctctcc cacgcacccg   1680
ctctcccaga tgaaccaccc tcctcttccc gatcccttgg gccggcccga tgaagatagt   1740
tcctcttcgt cttcctcctc ctgcagttcg gcttcggact cggagagtga gtccgaggag   1800
atgaaatgca gcagtggcgg aggagcatcc gtgacctcga gccaccatgg gcgcggcggt   1860
tttggtggcg cggcctcctc ctctctgctg agctgcggcc atcagagcag cggcggggcg   1920
agcaccggac cccgcaagaa gaagagcaaa cgcatctccg agttggacaa cgagaaggtg   1980
cgcaatatca tgaaagataa gaacacccc ttctgcacac ccaacgtgca gactcggcgg   2040
ggtcgcgtca agattgacga ggtgagccgc atgttccgca acaccaatcg ctctcttgag   2100
tacaagaacc tgcccttcac gattcccagt atgcaccagg tgttagatga ggccatcaaa   2160
gcctgcaaaa ccatgcaggt gaacaacaag ggcatccaga ttatctacac ccgcaatcat   2220
gaggtgaaga gtgaggtgga tgcggtgcgg tgtcgcctgg gcaccatgtg caacctggcc   2280
ctctccactc ccttcctcat ggagcacacc atgcccgtga catccacc cgaagtggcg   2340 cagcgcacag ccgatgcttg taacgaaggc gtcaaggccg cgtggagcct caaagaattg   2400
cacacccacc aattatgccc ccgttcctcc gattaccgca acatgatcat ccacgctgcc   2460
acccccgtgg acctgttggg cgctctcaac ctgtgcctgc ccctgatgca aaagtttccc   2520
aaacaggtca tggtgcgcat cttctccacc aaccaggtg ggttcatgct gcctatctac   2580
gagacggccg cgaaggccta cgccgtgggg cagtttgagc agcccaccga accctccc   2640 gaagacctgg acaccctgag cctggccatc gaggcagcca tccaggacct gaggaacaag   2700
tctcagtaa                                                            2709
```

<210> SEQ ID NO 12
<211> LENGTH: 46
<212> TYPE: DNA
<213> ORGANISM: Artificial Sequence
<220> FEATURE:
<223> OTHER INFORMATION: Primer "a" for construction of the IEfusion
    gene

<400> SEQUENCE: 12
agctttgttt aaacgccacc accatggtca aacagattaa ggttcg                    46

<210> SEQ ID NO 13
<211> LENGTH: 60
<212> TYPE: DNA
<213> ORGANISM: Artificial Sequence
<220> FEATURE:
<223> OTHER INFORMATION: Primer "b" for construction of the IEfusion
      gene

<400> SEQUENCE: 13
ggcatgattg acagcctggg cgaggatgtc accctggtca gccttgcttc tagtcaccat    60

<210> SEQ ID NO 14
<211> LENGTH: 69
<212> TYPE: DNA
<213> ORGANISM: Artificial Sequence
<220> FEATURE:
<223> OTHER INFORMATION: Primer "c" for construction of the IEfusion
      gene

<400> SEQUENCE: 14
tgttagcgtg ggcccggtgc tactggaatc gataccggca tgattgacag cctgggcgag    60
gatgtcacc                                                            69

<210> SEQ ID NO 15
<211> LENGTH: 28
<212> TYPE: DNA
<213> ORGANISM: Artificial Sequence
<220> FEATURE:
<223> OTHER INFORMATION: Primer "d" for construction of the IEfusion
      gene

<400> SEQUENCE: 15
tagcaccggg cccacgctaa caacccac                                       28

<210> SEQ ID NO 16
<211> LENGTH: 39
<212> TYPE: DNA
<213> ORGANISM: Artificial Sequence
<220> FEATURE:
<223> OTHER INFORMATION: Primer "e" for construction of the IEfusion
      gene

<400> SEQUENCE: 16
ttggcgcgcc tttattttac tgagacttgt tcctcaggt                           39

<210> SEQ ID NO 17
<211> LENGTH: 9
<212> TYPE: PRT
<213> ORGANISM: Artificial Sequence
<220> FEATURE:
<223> OTHER INFORMATION: carboxyl terminus of the 580 amino acid primary
      sequence of the IE2 protein [Swiss Prot #P19893]

<400> SEQUENCE: 17

Gly Pro Glu Asp Gln Asn Thr Ser Cys
1               5

<210> SEQ ID NO 18
<211> LENGTH: 17
<212> TYPE: PRT
<213> ORGANISM: Artificial Sequence
<220> FEATURE:
<223> OTHER INFORMATION: IE1/e4-IE2/e5 (IEfusion) gene

```
<400> SEQUENCE: 18

Met Val Thr Arg Ser Lys Ala Asp Gln Gly Asp Ile Leu Ala Gln Ala Val
1               5                   10                  15
```